US007304139B2

(12) United States Patent
Alleman et al.

(10) Patent No.: US 7,304,139 B2
(45) Date of Patent: Dec. 4, 2007

(54) **POLYNUCLEOTIDES AND POLYPEPTIDES OF *ANAPLASMA PHAGOCYTOPHILUM* AND METHODS OF USING THE SAME**

(75) Inventors: Arthur Rick Alleman, Alachua, FL (US); Anthony F. Barbet, Archer, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 536 days.

(21) Appl. No.: 10/696,019

(22) Filed: Oct. 28, 2003

(65) Prior Publication Data

US 2005/0142557 A1 Jun. 30, 2005

(51) Int. Cl.
*A61K 39/00* (2006.01)
*A61K 39/02* (2006.01)
*C07K 1/00* (2006.01)
*C07K 2/00* (2006.01)

(52) U.S. Cl. .................. 530/350; 530/300; 424/185.1; 424/190.1; 424/234.1

(58) Field of Classification Search ................ 530/300, 530/350; 424/185.1, 190.1, 234.1
See application file for complete search history.

(56) References Cited

U.S. PATENT DOCUMENTS

| | | | |
|---|---|---|---|
| 4,654,419 A * | 3/1987 | Vaughan et al. ............ 530/326 |
| 4,738,846 A | 4/1988 | Yoshida et al. |
| 4,816,567 A | 3/1989 | Cabilly et al. |
| 5,183,740 A | 2/1993 | Ligler et al. |
| 5,549,898 A | 8/1996 | McGuire et al. |
| 5,565,335 A | 10/1996 | Capon et al. |
| 5,643,570 A | 7/1997 | Theofan et al. |
| 5,712,170 A | 1/1998 | Kouvonen et al. |
| 5,726,010 A | 3/1998 | Clark |
| 5,750,352 A | 5/1998 | Vogelstein et al. |
| 5,798,219 A | 8/1998 | Knowles et al. |
| 5,843,464 A | 12/1998 | Bakaletz et al. |
| 5,955,089 A * | 9/1999 | Briles et al. ............. 424/244.1 |
| 5,990,275 A | 11/1999 | Whitlow et al. |
| 6,025,338 A | 2/2000 | Barbet et al. |
| 6,121,424 A | 9/2000 | Whitlow et al. |
| 6,251,872 B1 | 6/2001 | Barbet et al. |
| 6,277,375 B1 | 8/2001 | Ward |
| 6,319,691 B1 | 11/2001 | Pang |
| 6,342,362 B1 | 1/2002 | Mytelka |
| 6,417,337 B1 | 7/2002 | Anderson et al. |
| 6,419,931 B1 | 7/2002 | Vitiello et al. |
| 6,524,825 B1 | 2/2003 | Mizzen et al. |
| 6,593,147 B1 | 7/2003 | Barbet et al. |
| 6,653,128 B2 | 11/2003 | Barbet et al. |
| 2003/0044422 A1 | 3/2003 | Barbet et al. |
| 2004/0126871 A1 | 7/2004 | Barbet et al. |

FOREIGN PATENT DOCUMENTS

| EP | 0 404 097 B1 | 6/1990 |
|---|---|---|
| WO | WO 93/11161 | 6/1993 |
| WO | WO 98/16554 | 4/1998 |
| WO | WO 00/65063 | 11/2000 |

OTHER PUBLICATIONS

Plotkin et al (Vaccines WB Saunders Company p. 571, 1988).*
Visser, E.S. et al. (1992) "The *Anaplasma marginale* msp5 gene encodes a 19-kilodalton protein conserved in all recognized *Anaplasma* species" *Infect. Immun.* 60(12):5139-5144.
Bowie, M.V. et al. (1999) "Potential value of major antigenic protein 2 for serological diagnosis of heartwater and related Erlichial infections" *Clin. Diagn. Lab Immunol.* 6(2):209-215.
Mahan, S.M. et al. (1994) "Molecular cloning of a gene encoding the immunogenic 21 kDa protein of *Cowdria ruminantium*" *Microbiology* 140(Pt 8):2135-2142.
Hass, B.J. et al. (2002) "Full-length messenger RNA sequences greatly improve genome annotation" *Genome Biol.* 3(6):RESEARCH29.
Genbank Database Accession No. AA092930, Oct. 24, 1996.
Genbank Database Accession No. AAL17671, Oct. 27, 2001.
Genbank Database Accession No. CAE43991, May 6, 2004.
Genbank Database Accession No. CAE39512, May 6, 2004.
Genbank Database Accession No. CAE35184, May 6, 2004.
Genbank Database Accession No. NP_568068, Feb. 19, 2004.
Genbank Database Accession No. ZP_00024197, Sep. 26, 2003.
Altendorf et al. (1999) "Structure and function of the $F_o$ complex of the ATP synthase from *Escherichia coli*" *J. Exp. Biol.* 203:19-28.
Altschul et al. (1990) "Basic local alignment search tool" *J. Mol. Biol.* 215(3):403-410.
Alwine, et al. (1977) "Method for detection of specific RNAs in agarose gels by transfer to diazobenzyloxymethyl-paper and hybridization with DNA probes" *Proc. Natl. Acad. Sci.* 74:5350-5354.
Benoist and Chambon. (1981) "In vivo sequence requirements of the SV40 early promoter region" *Nature* 290:304-310.

(Continued)

*Primary Examiner*—Mark Navarro
(74) *Attorney, Agent, or Firm*—Saliwanchik, Lloyd & Saliwanchik

(57) ABSTRACT

We have successfully sequenced and cloned the gene expressing the Major Surface Protein 5 (MSP5) of *A. phagocytophilum*. The recombinant MSP5 (rMSP5) protein has been tested using sera from humans and dogs infected with *A. phacytophilum*. The polypeptide has been found to be immunogenic and useful as a diagnostic test antigen. The polypeptide antigen of the subject invention can provide the basis of a diagnostic assay that would allow the rapid, in-house, laboratory diagnosis of infection with *A. phagocytophilum* using a sample (e.g., serum, plasma, or whole blood) from an infected human or animal. Additionally, the subject invention provides methods of detecting the presence of *A. phagocytophilum* in biological or environmental samples utilizing antibodies provided by the subject invention. Furthermore, the use of the single antigen in the diagnosis of this important disease offers many advantages including enhanced test specificity, ease of testing and consistency of results using synthetically produced test antigens instead of cultured, whole organisms.

47 Claims, 2 Drawing Sheets

OTHER PUBLICATIONS

Berchtold, et al., (1989) "A simple method for direct cloning and sequencing cDNA by the use of a single specific oligonucleotide and oligo (dT) in a polymerase chain reaction (PCR)" *Nuc. Acids. Res.* 17(1):453.

Bianchi et al. (1997) "Biosensor technology and surface plasmon resonance for real-time detection of HIV-1 genomic sequences amplified by polymerase chain reaction" *Clin. Diagn. Virol.*, 8:199-208.

Brinster et al. (1982) "Regulation of metallothionein-thymidine kinase fusion plasmids injected into mouse eggs" *Nature* 296:39-42.

Clackson et al. (1991) "Making antibody fragments using phage display libraries" *Nature* 352:624-628.

De Boer, et al. (1983) "The *tac* promoter: A functional hybrid derived from the *trp* and *lac* promoters" *Proc. Natl. Acad. Sci. U.S.A.* 80:21-25.

Einhauer et al. (2001) "The FLAG™ peptide, a versatile fusion tag for the purification of recombinant proteins" *J. Biochem Biophys Methods* 49:455-465.

Gardner, et al. (1981) "The complete nucleotide sequence of an infectious clone of cauliflower mosaic virus by M13mp7 shotgun sequencing" *Nucl. Acids Res.* 9:2871-2888.

Gish and States (1993) "Identification of protein coding regions by database similarity search" *Nature Genetics* 3:266-272.

Herrera-Estrella et al. (1983) "Expression of chimaeric genes transferred into plant cells using a Ti-plasmid-derived vector" *Nature* 303:209-213.

Herrera-Estrella et al. (1984) "Light-inducible and chloroplast-associated expression of a chimaeric gene introduced into *Nicotiana tabacum* using a Ti plasmid vector" *Nature* 310:115-120.

Holliger et al. (1993) ""Diabodies" Small bivalent and bispecific antobody fragments" *Proc. Natl. Acad. Sci. USA* 90:6444-6448.

Jones et al. (1995) "Current trends in molecular recognition and bioseparation" *J. Chromatog. A.* 707:3-22.

Kohler and Milstein (1975) "Continuous cultures of fused cells secreting antibody of predefined specificity" *Nature* 256:495-497.

Kusterbeck et al. (1990) "A continuous flow immunoassay for rapid and sensitive detection of small molecules" *J. Immunol. Methods* 135:191-197.

Margolin (2000) "Green fluorescent protein as a reporter for macromolecular localization in bacterial cells" *Methods* 20:62-72.

Marks et al. (1991) "By-passing immunization. Human antibodies from V-gene libraries displayed on phage" *J. Mol. Biol.* 222:581-597.

Melton, et al. (1984) "Efficient in vitro synthesis of biologically active RNA and RNA hybridization probes from plasmids containing a bacteriophage SP6 promoter" *Nuc. Acids Res.* 12:7035-7056.

Morrison et al. (1984) "Chimeric human antibody molecules: Mouse antigen-binding domains with human constant region domains" *Proc. Natl. Acad Sci. USA* 81: 6851-6855.

Pearson and Lipman (1988) "Improved tools for biological sequence comparison" *Proc. Natl. Acad. Sci. USA* 85(8):2444-2448.

Puig et al. (2001) "The tandem affinity purification (TAP) method: A general procedure of protein complex purification" *Methods* 24:218-29.

Sambrook et al. (1989) "Analysis and Cloning of Eukaryotic Genomic DNA" IN: *Molecular Cloning. A Laboratory Manual, Second Edition*, Cold Spring Harbor Press, New York, NY, pp. 9.47-9.57.

Schena et al. (1995) "Quantitative monitoring of gene expression patterns with a complementary DNA microarray" *Science* 270:467-470.

Schena et al. (1996) "Genome analysis with gene expression microarrays" *BioEssays* 18:427-431.

Schena et al. (1996) "Parallel human genome analysis: Microarray-based expression monitoring of 1000 genes" *Proc. Natl. Acad. Sci. U.S.A.* 93:10614-10619.

Skerra et al (1999)] "Applications of a peptide ligand for streptavidin: The *Strep*-tag" *Biomolecular Engineering* 16:79-86.

Sutter et al. (1994) "A recombinant vector derived from the host range-restricted and highly attenuated MVA strain of vaccinia virus stimulates protective immunity in mice to influenza virus" *Vaccine* 12(11):1032-1040.

Thompson et al. (1994) "Clustal W: Improving the sensitivity of progressive multiple sequence alignment through sequence weighing, position-specific gap penalties and weight matrix choice" *Nucleic Acids Res.* 22(2):4673-4680.

Villa-Kamaroff et al. (1978) "A bacterial clone synthesizing proinsulin" *Proc. Natl. Acad. Sci. U.S.A.* 75:3727-3731.

Wagner et al. (1981) " Nucleotide sequence of the thymidine kinase gene of herpes simplex virus type 1" *Proc. Natl. Acad. Sci. U.S.A.* 78:1441-1445.

Wei et al. (1983) "Isolation and comparison of two molecular species of the BAL 31 nuclease from *Alteromonas espejiana* with distinct kinetic properties" *J. Biol. Chem.* 258:13506-13512.

Yamamoto et al. (1980) "Identification of a functional promoter in the long terminal repeat of Rous sarcoma virus" *Cell* 22:787-797.

Zapata et al. (1995) "Engineering linear F(ab')$_2$ fragments for efficient production in *Escherichia coli* and enhanced antiproliferative activity" *Protein Eng.* 8(10):1057-1062.

Sassenfeld (1990) "Engineering proteins for purification" *TibTech* 8:88-93.

Smith (1998) "Cookbook for eukaryotic protein expression: Yeast, insect, and plant expression systems" *The Scientist* 12(22):20.

Unger (1997) "Show me the money: Prokaryotic expression vectors and purification systems" *The Scientist* 11(17):20.

Kusterbeck et al. (1990) "Antibody-Based Biosensor for Continuous Monitoring" IN: *Biosensor Technology, Fundamentals and Applications*, R. P. Buck et al., eds., Marcel Dekker, New York, NY, pp. 345-350.

Ligler et al. (1992) "Drug Detection Using the Flow Immunosensor" IN: *Biosensor Design and Application*, J. Findley et al., eds., American Chemical Society Press, Washington, D.C., pp. 73-80.

Ogert et al. (1992) "Detection of cocaine using the flow immunosensor" *Analytical Letters* 25:1999-2019.

*Monoclonal Antibodies: Principles and Practice, Production and Application of Monoclonal Antibodies in Cell Biology, Biochemistry and Immunology* (1983), J.W. Goding ed., Academic Press, New York, NY.

*Monoclonal Hybridoma Antibodies: Techniques and Applications* (1982), J.G.R. Hurrell, ed., CRC Press, Boca Raton, FL.

*Selected Methods in Cellular Immunology* (1980), B.B. Mishell et al., eds., W.H. Freeman and Company, San Francisco, CA.

*Immunological Methods, vol. II* (1981), I. Lefkovits and B. Pernis, eds., Academic Press, Inc., New York, NY.

*Practical Immunology, Second Edition* (1980), L. Hudson and F.C. Hay, eds., Blackwell Scientific Publications, London.

Pietu et al. (1996) "Novel gene transcripts preferentially expressed in human muscles revealed by quantitative hybridization of a high density cDNA array" *Genome Research* 6:492-503.

Baneyx, F. (1999) "Recombinant protein expression in *Escherichia coli*" *Curr. Opin. Biotechnol.* 10:411-421.

\* cited by examiner

POLYNUCLEOTIDES AND POLYPEPTIDES OF *ANAPLASMA PHAGOCYTOPHILUM* AND METHODS OF USING THE SAME

*Anaplasma phagocytophilum* is a rickettsial agent that infects multiple species of mammals including humans, dogs, horses, cows and small ruminants. The current method of serological diagnosis relies on using whole, cultured organisms in an immunofluorescent antibody assay that is labor intensive, subjective in evaluation and nonspecific in reactivity. There remains a great need for an immunoassay system that simplifies the diagnosis and/or identification of *Anaplasma phagocytophilum* infections in individuals.

The currently existing methods for serological diagnosis of infection with *A. phagocytophilum* is the immunofluorescent antibody assay. This assay requires the use of whole, cultivated organisms to serve as diagnostic antigens. The production of these organisms is costly and labor intensive and there is no way to control antigen preparations of different lots to provide consistent immunoassay results.

The immunofluorescent assay itself is labor intensive and requires specialized equipment that is only available in commercial or research laboratories. Additionally, the assay requires highly skilled personnel to accurately interpret results. The rMSP5 could be synthetically produced as a peptide product, which would result in consistency in the test antigens. The synthetic peptide is adaptable to a format that would allow technicians in virtually any clinical setting to test subjects for antibodies to the organism. A positive result would be recognized by a visible color change on the test pad that could be interpreted by anyone with minimal training and skills.

BRIEF SUMMARY OF THE INVENTION

We have successfully sequenced and cloned the gene expressing the Major Surface Protein 5 (MSP5) of *A. phagocytophilum*. The recombinant MSP5 (rMSP5) protein has been tested using sera from humans and dogs infected with *A. phacytophilum*. The polypeptide has been found to be immunogenic and useful as a diagnostic test antigen. The polypeptide antigen of the subject invention can provide the basis of a diagnostic assay that would allow the rapid, in-house, laboratory diagnosis of infection with *A. phagocytophilum* using a sample (e.g., serum, plasma, or whole blood) from an infected human or animal. Additionally, the subject invention provides methods of detecting the presence of *A. phagocytophilum* in biological or environmental samples utilizing antibodies provided by the subject invention. Furthermore, the use of the single antigen in the diagnosis of this important disease offers many advantages including enhanced test specificity, ease of testing and consistency of results using synthetically produced test antigens instead of cultured, whole organisms.

BRIEF DESCRIPTION OF THE TABLES

Figure 1:
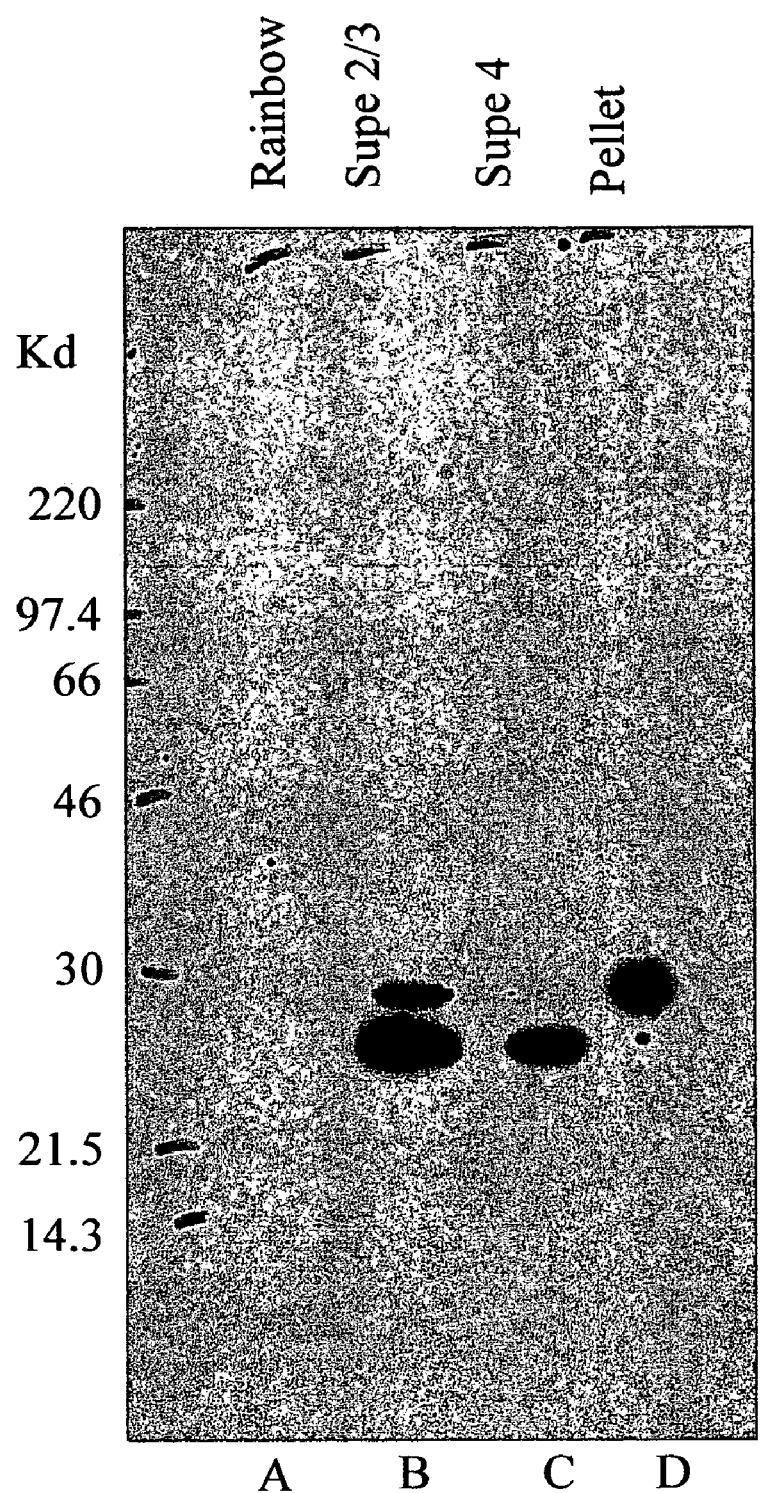
FIG. 1—Coumassie Blue-stained gel of purified recombinant MSP5 (rMSP5) from *A. phagocytophilum*. Lane A contains molecular weight standards; Lanes B and C contain fractions of soluble rMSP5 in the supernatant of the eluted material; Lane D contains rMSP5 from a pelleted insoluble fraction.
Figure 2:
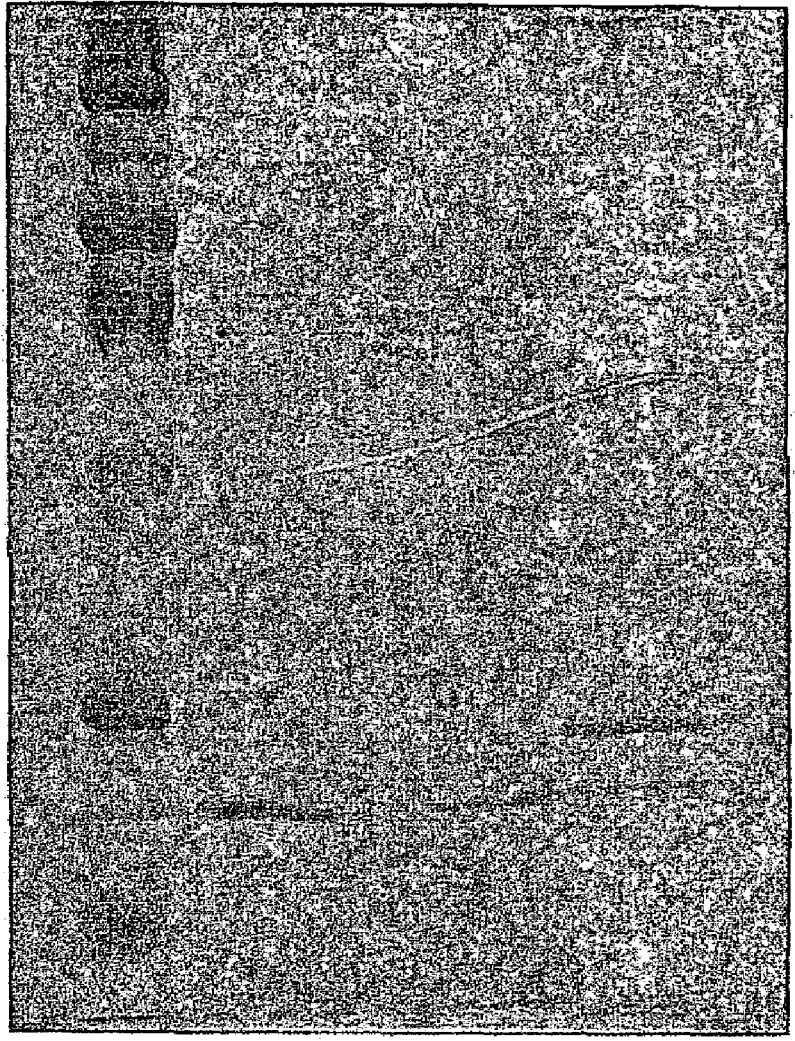
FIG. 2—Western immunoblot using rMSP5 and peroxidase labeled ant-histidine antibody to identify the recombinant protein with the histidine tag. Lanes B,and C contain rMSP5 from soluble fractions and Lane D contains rMSP5 from the insoluble pellet. Horseradish peroxidase labeled anti-His antibodies were as the expressed rMSP5 contained a polyhistidine tag.

Tables 1-3 provides exemplary polypeptide fragments of the polypeptides of the subject invention (e.g., the polypeptides of SEQ ID NO: 2, 3, and 4).

Tables 4-5 illustrate the results of enzyme linked immunosorbent (ELISA) assays using recombinant rMSP5 to detect antibodies in the serum of infected and non-infected humans (Table 4) and dogs (Table 5). Samples from non-infected humans were used to establish cutoff values for positive reactors. An optical density (OD) reading based upon the mean from the normal samples (at each dilution) plus three standard deviations (SD) was used as the upper limit of normal. Any samples with OD readings greater than the mean+3SD (of the normal samples at the same dilutions) were considered positive reactors. Human samples were tested at dilutions of 1/100, 1/300, and 1/1000. Canine samples were tested at dilutions of 1/100and 1/300.

In Table 4, serum samples from non-infected humans (Normals 1-5) were compared to samples obtained from humans that were PCR positive for *A. phagocytophilum*. As illustrated in the table, all samples were serologically positive except for the sample obtained from 99-01291 (this sample was PCR positive but serologically negative when tested by a different assay).

In Table 5, ELISA tests using serum samples from non-infected dogs (Molly, CN76AC, CN115A, CN125C, CN35B, Dixie, CN54B, CN105C, Presley, and CN74H) and samples obtained from a commercial source (IDEXX Laboratories, Inc., Westbrook, Me.). Samples from IDEXX were blinded as 10 of the samples were positive for antibodies to *A. phagocytophilum* (samples 4, 6, 11, 12, 13, 15, 16, 17, 18, and 20). Samples with OD readings greater than the mean+3SD (of the normal samples at the same dilutions) were considered positive reactors.

BRIEF DESCRIPTION OF THE SEQUENCES

SEQ ID NO: 1 provides a polynucleotide sequence encoding a MSP5 polypeptide of the subject invention.

SEQ ID NO: 2 depicts a processed form (lacking a signal peptide) of a MSP5 polypeptide of the subject invention.

SEQ ID NO: 3 illustrates an unprocessed form of a MSP5 polypeptide of the subject invention (e.g., containing a signal peptide).

SEQ ID NO: 4 is a signal peptide of the subject invention.

DETAILED DESCRIPTION OF THE INVENTION

The subject invention provides:

a) one or more:

1) isolated, purified, and/or recombinant polypeptides comprising SEQ ID NO: 2, 3, or 4;
2) variant polypeptides having at least about 20% to 99.99% identity, preferably at least 60 to 99.99% identity to the polypeptide of SEQ ID NO: 2, 3, or 4 and which has at least one of the activities associated with the polypeptide of SEQ ID NO: 2, 3, or 4;
3) a fragment of the polypeptide of SEQ ID NO: 2, 3, or 4, or a variant polypeptide, wherein said polypeptide fragment or fragment of said variant polypeptide has substantially the same activity as the polypeptide of SEQ ID NO: 2, 3, or 4;

4) a multimeric polypeptide construct comprising a series of repeating elements that are, optionally, joined together by linker elements, wherein said repeating elements are selected from one, or more, of the following polypeptides: a) SEQ ID NO: 2; b) SEQ ID NO: 3; c) SEQ ID NO: 4; d) fragments of SEQ ID NO: 2; e) fragments of SEQ ID NO: 3; or f) fragments of SEQ ID NO: 4;

5) an epitope of a polypeptide selected from the group consisting of SEQ ID NO: 2, SEQ ID NO: 3, and SEQ ID NO: 4;

6) a multi-epitope construct comprising at least one epitope as set forth herein; or 7) a polypeptide according to embodiments a(1), a(2), a(3), a(4), a(5), or a(6) that further comprises a heterologous polypeptide sequence;

b) a composition comprising a carrier and a polypeptide as set forth in a(1), a(2), a(3), a(4), a(5), a(6), or a(7), wherein said carrier is an adjuvant or a pharmaceutically acceptable excipient;

c) methods of detecting the presence of antibodies in an individual infected with *A. phagocytophilum* comprising contacting a biological sample with a polypeptide or polypeptides as set forth in a(1), a(2), a(3), a(4), a(5), a(6), or a(7) and detecting the presence of an antigen/antibody complex;

d) an improvement in methods of diagnosing or detecting an *A. phagocytophilum* infection in an individual, wherein the improvement comprises the use of an isolated, purified, and/or recombinant polypeptide as set forth in a(1), a(2), a(3), a(4), a(5), a(6), or a(7) in an immunoassay for the detection or diagnosis of an *A. phagocytophilum* infection;

In the context of the instant invention, the terms "oligopeptide", "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells, or by chemical synthesis). Polypeptides according to the instant invention may also contain non-natural amino acids, as will be described below. The terms "oligopeptide", "polypeptide", "peptide" and "protein" are also used, in the instant specification, to designate a series of residues, typically L-amino acids, connected one to the other, typically by peptide bonds between the α-amino and carboxyl groups of adjacent amino acids. Linker elements can be joined to the polypeptides of the subject invention through peptide, bonds or via chemical bonds (e.g., heterobifunctional chemical linker elements) as set forth below. Additionally, the terms "amino acid(s)" and "residue(s)" can be used interchangeably.

Thus, the subject invention provides polypeptides comprising SEQ ID NOs: 2, 3 or 4 and/or polypeptide fragments of SEQ ID NOs: 2, 3 or 4. In some embodiments of the subject invention, polypeptide fragments of the subject invention are epitopes that are bound by antibodies or T-cell receptors are designated "epitopes"; in the context of the subject invention, "epitopes" are considered to be a subset of the invention designated as "fragments of SEQ ID NOs: 2, 3 or 4". In yet another aspect of the invention, a "fragment" within the context of the subject invention comprises the signal peptide (signal sequence) of SEQ ID NO: 4.

Polypeptide fragments (and/or epitopes) according to the subject invention, usually comprise a contiguous span of or at least 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, 35, 36, 37, 38, 39, 40, 41, 42, 43, 44, 45, 46,47, 48, 49, 50, 51, 52, 53, 54, 55, 56, 57, 58, 59, 60, 61, 62, 63, 64, 65, 66, 67, 68, 69, 70, 71, 72, or 73 amino acids of SEQ ID NO:2; in one embodiment, a fragment of SEQ ID No: 2 comprises, consists essentially of, or consists of amino acids 17-74 of SEQ ID NO:2. In other embodiments, the subject invention provides fragments of SEQ ID No: 3 that are, or that are at least, 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 consecutive amino acids.

Polypeptide fragments of the subject invention can be any integer in length from at least 3, preferably 4, and more preferably 5 consecutive amino acids to 1 amino acid less than a full length polypeptide of SEQ ID NO: 2, 3 or 4. Thus, for SEQ ID No: 2, a polypeptide fragment can be any integer of consecutive amino acids from 3 to 73 amino acids; for SEQ ID No: 3, a fragment can be any integer of consecutive amino acids from 5 to 57 consecutive amino acids, for example. The term "integer" is used herein in its mathematical sense and thus representative integers include: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42,43, 44, 45,46, 47, 48, 49, 50, 51, 52, 53, 54, 55, 56, 57, 58, 59, 60, 61, 62, 63, 64, 65, 66, 67, 68, 69, 70, 71, 72, 73, and/or 74.

Each polypeptide fragment of the subject invention can also be described in terms of its N-terminal and C-terminal positions. For example, combinations of N-terminal to C-terminal fragments of 6 contiguous amino acids to 1 amino acid less than the full length polypeptide of SEQ ID No: 2 are included in the present invention. Thus, a 6 consecutive amino acid fragment could occupy positions selected from the group consisting of 1-6, 2-7, 3-8, 4-9, 5-10, 6-11, 7-12, 8-13, 9-14, 10-15, 11-16, 12-17, 13-18, 14-19, 15-20, 16-21, 17-22, 18-23, 19-24, 20-25, 21-26, 22-27, 23-28, 24-29, 25-30, 26-31, 27-32, 28-33, 29-34, 30-35, 31-36, 32-37, 33-38, 34-39, 35-40, 36-41, 37-42, 38-43, 39-44, 40-45, 41-46, 42-47, 43-48, 44-49, 45-50, 46-51, 47-52, 48-53, 49-54, 50-55, 51-56, 52-57, 53-58, 54-59, 55-60, 56-61, 57-62, 58-63, 59-64, 60-65, 61-66, 62-67, 63-68, 64-69, 65-70, 66-71, 67-72, 68-73, and 69-74. A 70 consecutive amino acid fragment could occupy positions selected from the group consisting of 1-70, 2-71, 3-72, 4-73, and 5-74 of SEQ ID NO: 2.

Exemplary polypeptide fragments of SEQ ID NOs: 2, 3 or 4 are also set forth in Tables 1, 2, and 3 of the subject specification. As is indicated in the tables appended hereto, polypeptide fragments have an N-terminal amino acid residue that corresponds to an amino acid position of the SEQ ID NO: indicated in the table and a C-terminal amino acid residue that, likewise, corresponds to an amino acid position of the SEQ ID NO: indicated in the table. Any polypeptide fragment listed in the appended tables may be included or specifically excluded from the subject invention.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector according to the invention. The transformed host cells contain a nucleic acid, allowing the expression of these fragments, under the control of appropriate elements for regulation and/or expression of the polypeptide fragments. Various polypeptide fragments encompassed within the scope of the subject invention are provided in Table 3. The cleavage point indicated in the table is at the carboxy group of the amino acid indicated in the table; the numerical value indicated in Table 3 corresponds to the amino acid at the identical position in SEQ ID NO: 2.

In certain preferred embodiments, fragments of the polypeptides disclosed herein retain at least one property or activity of the full-length polypeptide from which the fragments are derived. Thus, fragments of the polypeptide of SEQ ID NOs: 2, 3 or 4 have one or more of the following properties or activities: a) the ability to: 1) specifically bind to antibodies specific for SEQ ID NO: 2, 3, 4; and/or 2) specifically bind antibodies found in an animal or human infected with *A. phagocytophilum*; b) the ability to bind to, and activate T-cell receptors (CTL (cytptoxic T-lymphocyte) and/or HTL (helper T-lymphocyte receptors)) in the context of MHC Class I or Class II antigen that are isolated or derived from an animal or human infected with *A. phagocytophilum*; 3) the ability to induce an immune response in an animal or human; 4) the ability to induce a protective immune response in an animal or human against *A. phagocytophilum*; and/or 5) the ability to direct the extracellular secretion of a polypeptide (e.g., a signal peptide such as SEQ ID NO: 4).

The polypeptides, and fragments thereof, may further comprise linker elements (L) that facilitate the attachment of the fragments to other molecules, amino acids, or polypeptide sequences. The linkers can also be used to attach the polypeptides, or fragments thereof, to solid support matrices for use in affinity purification protocols. Non-limiting examples of "linkers" suitable for the practice of the invention include chemical linkers (such as those sold by Pierce, Rockford, Ill.), or peptides that allow for the connection combinations of polypeptides (see, for example, linkers such as those disclosed in U.S. Pat. Nos. 6,121,424, 5,843,464, 5,750,352, and 5,990,275, hereby incorporated by reference in their entirety).

In other embodiments, the linker element (L) can amino acid sequences. In other embodiments, the peptide linker has one or more of the following characteristics: a) it allows for the free rotation of the polypeptides that it links (relative to each other); b) it is resistant or susceptible to digestion (cleavage) by proteases; and c) it does not interact with the polypeptides it joins together. In various embodiments, a multimeric construct according to the subject invention includes a peptide linker and the peptide linker is 5 to 60 amino acids in length. More preferably, the peptide linker is 10 to 30, amino acids in length; even more preferably, the peptide linker is 10 to 20 amino acids in length. In some embodiments, the peptide linker is 17 amino acids in length.

Peptide linkers suitable for use in the subject invention are made up of amino acids selected from the group consisting of Gly, Ser, Asn, Thr and Ala. Preferably, the peptide linker includes a Gly-Ser element. In a preferred embodiment, the peptide linker comprises (Ser-Gly-Gly-Gly-Gly)$_y$, wherein y is 1, 2, 3, 4, 5, 6, 7, or 8. Other embodiments provide for a peptide linker comprising ((Ser-Gly-Gly-Gly-Gly)$_y$-Ser-Pro). In certain preferred embodiments, y is a value of 3, 4, or 5. In other preferred embodiment, the peptide linker comprises (Ser-Ser-Ser-Ser-Gly)$_y$ or ((Ser-Ser-Ser-Ser-Gly)$_y$-Ser-Pro), wherein y is 1, 2, 3, 4, 5, 6, 7, or 8. In certain preferred embodiments, y is a value of 3, 4, or 5. Where cleavable linker elements are desired, one or more cleavable linker sequences such as Factor Xa or enterokinase (Invitrogen, San Diego Calif.) can be used alone or in combination with the aforementioned linkers Multimeric constructs of the subject invention typically comprise a series of repeating elements, optionally interspersed with other elements. As would be appreciated by one skilled in the art, the order in which the repeating elements occur in the multimeric polypeptide is not critical and any arrangement of the repeating elements as set forth herein can be provided by the subject invention. Thus, a "multimeric construct" according to the subject invention can provide a multimeric polypeptide comprising a series of polypeptides, polypeptide fragments, or epitopes that are, optionally, joined together by linker elements (either chemical linker elements or amino acid linker elements).

Non-limiting examples of multimeric polypeptide constructs according to the subject invention comprise: a) (SEQ ID NO: 2)$_{2x}$, (SEQ ID NO: 3)$_{2x}$, or (SEQ ID NO: 4)$_{2x}$; or b) [L$_d$-(SEQ ID NO:2)]$_{2x}$, [L$_d$-(SEQ ID NO:3)]$_{2x}$, [L$_d$-(SEQ ID NO:4)]$_{2x}$, [(SEQ ID NO: 2)$_a$-L$_d$-(SEQ ID NO:3)$_b$]$_x$, [(SEQ ID NO: 2)$_a$-L$_d$-(SEQ ID NO:4)$_b$]$_x$, [(SEQ ID NO: 3)$_a$-L$_d$-(SEQ ID NO:4)$_b$]$_x$ or [(SEQ ID NO: 2)$_a$-L$_d$-(SEQ ID NO:3)$_b$-L$_e$-(SEQ ID NO:4)$_c$]$_x$, wherein: 1) L is a linker element joined to the polypeptides of SEQ ID NO: 2, 3 or 4, or fragments of SEQ ID NO: 2 and/or 3; 2) x is an integer from 1 to 100; 3) a, b, and c can be the same, or different, and are an integer from 1 to 100; and 4) d and e can be the same, or different and are an integer from 0 to 100, preferably 0 to 10, and more preferably 0, 1, 2, 3, 4, 5, 6, 7, or 8, and even more preferably 3, 4, or 5. Some embodiments provide for multimeric constructs of SEQ ID NO: 2 or SEQ ID NO: 3 wherein no linker elements are provided (e.g., a multimeric construct represented by the formula (SEQ ID NO: 2)$_x$ or (SEQ ID NO: 3)$_x$, wherein x is an integer value from 2 to 200). The order and arrangement of SEQ ID NO: 2, 3, 4 and/or fragments thereof can be altered in any fashion and it is not necessary that the sequences alternate, and in the context of this aspect of the invention, "SEQ ID NO: 2", "SEQ ID NO: 3", and "SEQ ID NO: 4" can be interchanged with fragments of the given SEQ ID NO:.

A "variant polypeptide" (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among these homologous variant polypeptides, are those comprising amino acid sequences exhibiting between at least (or at least about) 20.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant polypeptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In a preferred embodiment, a variant or modified polypeptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to SEQ ID NOS: 2, 3 or 4. Typically, the percent identity is calculated with reference to the full-length, native, and/or naturally occurring polypeptide (e.g. those polypeptides set forth in SEQ ID NO: 2, SEQ ID NO: 3 or SEQ ID NO: 4). In all instances, variant polypeptides retain at least one of the activities associated with the polypeptide set forth in SEQ ID NOs: 2, 3 or 4. In some embodiments, variant polypeptides retain at least 2, and preferably all of the activities associated with the polypeptide.

Variant polypeptides can also comprise one or more heterologous polypeptide sequences (e.g., tags that facilitate purification of the polypeptides of the invention (see, for example, U.S. Pat. No. 6,342,362, hereby incorporated by reference in its entirety; Altendorf et al [1999-WWW, 2000] "Structure and Function of the $F_o$ Complex of the ATP Synthase from *Escherichia Coli*," *J. of Experimental Biology* 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A*. 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B. V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

In other embodiments, polypeptides of the subject invention (e.g., SEQ ID NOs: 2, 3, and/or 4 or fragments thereof) can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety). As indicated supra, the signal peptide of SEQ ID NO: 4 can be used to direct the extracellular secretion of any protein to which they are operably linked. Signal peptides find application in simplifying protein purification techniques. In such applications, the extracellular secretion of the desired protein greatly facilitates purification by reducing the number of undesired proteins from which the desired protein must be selected. Thus, a signal peptide of the subject invention can be operably linked to a heterologous polypeptide to direct the secretion of said polypeptide from a transformed host cell.

Also included within the scope of the subject invention are at least one or more polypeptide fragments of SEQ ID NO: 2, 3, or 4 that are an "epitope". In the context of the subject invention, an the term "epitope" is used to designate a series of residues, typically L-amino acids, connected one to the other, typically by peptide bonds between the α-amino and carboxyl groups of adjacent amino acids. The preferred CTL (or $CD8^+$ T cell)-inducing peptides of the invention are 13 residues or less in length and usually consist of between about 8 and about 11 residues (e.g., 8, 9, 10 or 11 residues), preferably 9 or 10 residues. The preferred HTL (or $CD4^+$ T cell)-inducing peptides are less than about 50 residues in length and usually consist of between about 6 and about 30 residues, more usually between about 12 and 25 (e.g., 12, 13, 14, 15, 16, 17, 18, 19, 20, 21, 22, 23, 24 or 25), and often between about 15 and 20 residues (e.g., 15, 16, 17, 18, 19 or 20).

The nomenclature used to describe peptide compounds follows the conventional practice wherein the amino group is presented to the left (the N-terminus) and the carboxyl group to the right (the C-terminus) of each amino acid residue. The L-form of an amino acid residue is represented by a capital single letter or a capital first letter of a three-letter symbol, and the D-form, for those amino acids having D-forms, is represented by a lower case single letter or a lower case three letter symbol. Glycine has no asymmetric carbon atom and is simply referred to as "Gly" or G. Symbols for the amino acids are as follows: (Single Letter Symbol; Three Letter Symbol Amino Acid) A; Ala; Alanine: C; Cys; Cysteine: D; Asp; Aspartic Acid: E; Glu; Glutamic Acid: F; Phe; Phenylalanine: G; Gly; Glycine: H; His; Histidine: I; Ile; Isoleucine: K; Lys; Lysine: L; Leu; Leucine: M; Met; Methionine: N; Asn; Asparagine: P; Pro; Proline: Q; Gln; Glutamine: R; Arg; Arginine: S; Ser; Serine: T; Thr; Threonine: V; Val; Valine: W; Trp; Tryptophan: Y; Tyr; Tyrosine. Amino acid "chemical characteristics" are defined as: Aromatic (F, W, Y); Aliphatic-hydrophobic (L, I, V, M); Small polar (S, T, C); Large polar (Q, N); Acidic (D, E); Basic (R, H, K); Non-polar: (P, A, G) Proline; Alanine; and Glycine. By way of example, amino acid substitutions can be carried out without resulting in a substantial modification of the associated activity (or activities) of the corresponding modified polypeptides; for example, the replacement of leucine with valine or isoleucine, of aspartic acid with glutamic acid, of glutamine with asparagine, of arginine with lysine, and the like, the reverse substitutions can be performed without substantial modification of the biological activity of the polypeptides.

In order to extend the life of the polypeptides according to the invention, it may be advantageous to use non-natural amino acids, for example in the D-form, or alternatively amino acid analogs, for example sulfur-containing forms of amino acids in the production of "variant polypeptides". Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. Nos. 6,319, 691, 6,277,375, or 5,643,570, each of which is incorporated by reference in its entirety, including all references cited within each respective patent. Alternatively, the polynucleotides and genes of the instant invention can be recombinantly fused to elements, well known to the skilled artisan, that are useful in the preparation of immunogenic constructs for the purposes of vaccine formulation.

The subject invention also provides biologically active fragments (epitopes) of a polypeptide according to the invention and includes those peptides capable of eliciting an immune response directed against *A. phagocytophilum*, said immune response providing components (B-cells, antibodies, and/or or components of the cellular immune response (e.g., helper, cytotoxic, and/or suppressor T-cells)) reactive with the fragment of said polypeptide; the intact, full length, unmodified polypeptide disclosed herein; or both a fragment of a polypeptide and the intact, full length, unmodified polypeptides disclosed herein.

The subject application also provides a composition comprising at least one isolated, recombinant, or purified polypeptide as set forth herein and at least one additional component. In various aspects of the invention, the additional component is a solid support (for example, microtiter wells, magnetic beads, non-magnetic beads, agarose beads, glass, cellulose, plastics, polyethylene, polypropylene, polyester, nitrocellulose, nylon, or polysulfone) and/or a pharmaceutically acceptable excipient or adjuvant known to those skilled in the art. In some aspects of the invention, the solid support provides an array of polypeptides of the subject invention or an array of polypeptides comprising combinations of various polypeptides of the subject invention. Compositions of the subject invention can also comprise additional antigens of interest (e.g., *Anaplasma marginale, Anaplasma centrale, Ehrlichia canis, Ehrlichia chaffeensis*, or *Cowdria ruminantium*, and/or *Borrelia burgdorferi*).

In one embodiment, the subject invention provides methods for eliciting an immune response in an individual comprising the administration of compositions comprising polypeptides according to the subject invention to an individual in amounts sufficient to induce an immune response in the individual. In some embodiments, a "protective" or "therapeutic immune response" is induced in the individual. A "protective immune response" or "therapeutic immune response" refers to a CTL (or $CD8^+$ T cell) and/or an HTL (or $CD4^+$ T cell), and/or an antibody response to an antigen derived from an infectious agent or a tumor antigen, which in some way prevents or at least partially arrests disease symptoms, side effects or progression. The protective immune response may also include an antibody response that has been facilitated by the stimulation of helper T cells (or $CD4^+$ T cells). Additional methods of inducing an immune response in an individual are taught in U.S. Pat. No. 6,419,931, hereby incorporated by reference in its entirety. The term CTL can be used interchangeably with $CD8^+$ T-cell(s) and the term HTL can be used interchangeably with $CD4^+$ T-cell(s) throughout the subject application.

The term "individual" includes mammals which include, and are not limited to, apes, chimpanzees, orangutans, humans, monkeys or domesticated animals (pets) such as dogs, cats, guinea pigs, hamsters, Vietnamese pot-bellied pigs, rabbits, ferrets, cows, horses, goats and sheep. In a preferred embodiment, the methods of inducing an immune response contemplated herein are practiced on humans.

The composition administered to the individual may, optionally, contain an adjuvant and may be delivered in any manner known in the art for the delivery of immunogen to a subject. Compositions may also be formulated in any carriers, including for example, pharmaceutically acceptable carriers such as those described in E. W. Martin's *Remington's Pharmaceutical Science*, Mack Publishing Company, Easton, Pa. In preferred embodiments, compositions may be formulated in incomplete Freund's adjuvant, complete Freund's adjuvant, or alum.

In other embodiments, the subject invention provides for diagnostic assays based upon Western blot formats or standard immunoassays known to the skilled artisan. For example, antibody-based assays such as enzyme linked immunosorbent assays (ELISAs), radioimmunoassays (RIAs); lateral flow assays, reversible flow chromatographic binding assay (see, for example, U.S. Pat. No. 5,726,010, which is hereby incorporated by reference in its entirety), immunochromatographic strip assays, automated flow assays, and assays utilizing peptide- or antibody-containing biosensors may be employed for the detection of: 1) the polypeptides, and fragments thereof, provided by the subject invention; or 2) antibodies that bind to the polypeptides or fragments thereof, provided by the subject invention; The assays and methods for conducting the assays are well-known in the art and the methods may test biological samples (e.g., serum, plasma, or blood) qualitatively (presence or absence of polypeptide) or quantitatively (comparison of a sample against a standard curve prepared using a polypeptide of the subject invention) for the presence of: a) one or more polypeptide of the subject invention, or 2) antibodies that bind to polypeptides of the subject invention.

Thus, the subject invention provides a method of detecting an *A. phagocytophilum* polypeptide, variant, or fragment of said polypeptide or variant, comprising contacting a sample with an antibody that specifically binds to: 1) a polypeptide, or fragment thereof, or 2) a variant, or a fragment thereof, and detecting the presence of an antibody-antigen complex. Alternatively, the subject invention provides a method of detecting antibodies to *A. phagocytophilum* comprising contacting a sample from an individual with: 1) a polypeptide of the subject invention, or fragment thereof, or 2) a variant of the subject invention, or a fragment thereof, and detecting the presence of an antibody-antigen complex. A sample can comprise a blood, serum, or tissue sample from an individual infected by *A. phagocytophilum*. Alternatively, a sample can comprise culture medium in which polypeptides of the subject invention (or fragments thereof) are expressed or transformed host cells (lysed or intact cells) expressing polypeptides (or fragments thereof) that are provided by the subject invention.

The antibody-based assays can be considered to be of four types: direct binding assays, sandwich assays, competition assays, and displacement assays. In a direct binding assay, either the antibody or antigen is labeled, and there is a means of measuring the number of complexes formed. In a sandwich assay, the formation of a complex of at least three components (e.g., antibody-antigen-antibody) is measured. In a competition assay, labeled antigen and unlabelled antigen compete for binding to the antibody, and either the bound or the free component is measured. In a displacement assay, the labeled antigen is pre-bound to the antibody, and a change in signal is measured as the unlabelled antigen displaces the bound, labeled antigen from the receptor.

Lateral flow assays can be conducted according to the teachings of U.S. Pat. No. 5,712,170 and the references cited therein. U.S. Pat. No. 5,712,170 and the references cited therein are hereby incorporated by reference in their entireties. Displacement assays and flow immunosensors useful for carrying out displacement assays are described in: (1) Kusterbeck et al., "Antibody-Based Biosensor for Continuous Monitoring", in Biosensor Technology, R. P. Buck et al., eds., Marcel Dekker, N.Y. pp. 345-350 (1990); Kusterbeck et al., "A Continuous Flow Immunoassay for Rapid and Sensitive Detection of Small Molecules", Journal of Immunological Methods, vol. 135, pp. 191-197 (1990); Ligler et al., "Drug Detection Using the Flow Immunosensor", in Biosensor Design and Application, J. Findley et al., eds., American Chemical Society Press, pp. 73-80 (1992); and Ogert et al., "Detection of Cocaine Using the Flow Immunosensor", Analytical Letters, vol. 25, pp. 1999-2019 (1992), all of which are incorporated herein by reference in their entireties. Displacement assays and flow immunosensors are also described in U.S. Pat. No. 5,183,740, which is also incorporated herein by reference in its entirety. The displacement immunoassay, unlike most of the competitive immunoassays used to detect small molecules, can generate a positive signal with increasing antigen concentration. One aspect of the invention allows for the exclusion of Western blots as a diagnostic assay, particularly where the Western blot is a screen of whole cell lysates of *A. phagocytophilum*, or related organisms, against immune serum of infected individuals. In another aspect of the invention, peptide, or polypeptide, based diagnostic assays utilize *A. phagocytophilum* peptides or polypeptides that have been produced either by chemical peptide synthesis or by recombinant methodologies.

The subject invention also provides methods of binding an antibody to a polypeptide of the subject invention comprising contacting a sample containing an antibody with a polypeptide under conditions that allow for the formation of an antibody-antigen complex. These methods can further comprise the step of detecting the formation of said antibody-antigen complex. In various aspects of this method, an immunoassay is conducted for the detection of *Anaplasma phagocytophilum*. Non-limiting examples of such immunoassays include enzyme linked immunosorbent assays (ELISAs), radioimmunoassays (RIAs), lateral flow assays, immunochromatographic strip assays, automated flow assays, Western blots, immunoprecipitation assays, reversible flow chromatographic binding assays, agglutination assays, and biosensors. Additional aspects of the invention provide for the use of an array of polypeptides when conducted the aforementioned methods of detection (the array can comprise polypeptides of the same or different sequence as well as polypeptides from one or more other organisms (e.g., *Anaplasma marginale*, *Anaplasma centrale*, *Ehrlichia canis*, *Ehrlichia chaffeensis*, or *Cowdria ruminantium*, and/or *Borrelia burgdorferi*).

The subject invention also concerns antibodies that bind to polypeptides of the invention. Antibodies that are immunospecific for the polypeptides as set forth herein are specifically contemplated. In various embodiments, antibodies that do not cross-react with other proteins (such as *A. marginale* MSP5) are also specifically contemplated. The antibodies of the subject invention can be prepared using standard materials and methods known in the art (see, for example, *Monoclonal Antibodies: Principles and Practice*, 1983; *Monoclonal Hybridoma Antibodies: Techniques and Applications*, 1982; *Selected Methods in Cellular Immunology*, 1980, *Immunological Methods, Vol. II*, 1981; *Practical Immunology*, and Kohler et al. [1975] *Nature* 256:495). These antibodies can further comprise one or more additional components, such as a solid support, a carrier or pharmaceutically acceptable excipient, or a label. In certain aspects of the invention, the antibodies of the invention does not cross-react with an antigen of *Anaplasma marginale*, *Anaplasma centrale*, *Ehrlichia canis*, *Ehrlichia chaffeensis*, or *Cowdria ruminantium*.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity, particularly neutralizing activity. AAntibody fragments≅ comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multi-specific antibodies formed from antibody fragments.

The term Amonoclonal antibody≅ as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier Amonoclonal≅ indicates the character of the antibody as being obtained from a substantially homogeneous population of antibodies, and is not to be construed as requiring production of the antibody by any particular, method. For example, the monoclonal antibodies to be used in accordance with the present invention may be made by the hybridoma method first described by Kohler et al. [1975] *Nature* 256: 495, or may be made by recombinant. DNA methods (see, e.g., U.S. Pat. No. 4,816,567). The Amonoclonal antibodies≅ may also be isolated from phage antibody libraries using the techniques described in Clackson et al. [1991] *Nature* 352: 624-628 and Marks et al. [1991] *J. Mol. Biol.* 222: 581-597, for example.

The monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. [1984] *Proc. Natl. Acad Sci. USA* 81: 6851-6855). Also included are humanized antibodies, such as those taught in U.S. Pat. Nos. 6,407,213 or 6,417,337 which are hereby incorporated by reference in their entirety.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see, Pluckthun in The Pharmacology of Monoclonal Antibodies [1994] Vol. 113:269-315, Rosenburg and Moore eds. Springer-Verlag, New York.

The term Adiabodies≅ refers to small antibody fragments with two antigen-binding sites, which fragments comprise a heavy chain variable domain (V$_H$) connected to a light chain variable domain (V$_L$) in the same polypeptide chain (V$_H$-V$_L$). Diabodies are described more fully in, for example, EP 404,097; WO 93/11161; and Hollinger et al. [1993] *Proc. Natl. Acad. Sci. USA* 90: 6444-6448. The term Alinear antibodies≙ refers to the antibodies described in Zapata et al. [1995] *Protein Eng.* 8(10):1057-1062.

An Aisolated≙ antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment. "Link" or "join" refers to any method known in the art for functionally connecting peptides, including, without limitation, recombinant fusion, covalent bonding, disulfide bonding, ionic bonding, hydrogen bonding, and electrostatic bonding.

The subject invention also provides isolated, recombinant, and/or purified polynucleotide sequences comprising:
a) a polynucleotide sequence encoding a polypeptide as set forth in paragraph 13(a);
b) a polynucleotide sequence having at least about 20% to 99.99% identity to a polynucleotide sequence encoding a polypeptide SEQ ID NOs: 2, 3, or 4, wherein said polynucleotide encodes a polypeptide having at least one of the activities of SEQ ID NOs: 2, 3, or 4;
c) a polynucleotide sequence comprising SEQ ID NO: 1;
d) a polynucleotide sequence having at least about 20% to 99;99% identity to the polynucleotide sequence of SEQ ID NO: 1;
e) a polynucleotide that is complementary to the polynucleotides set forth in (a), (b), (c), or (d);
f) a genetic construct comprising a polynucleotide sequence as set forth in (a), (b), (c), (d), or (e);
g) a vector comprising a polynucleotide or genetic construct as set forth in (a), (b), (c), (d), (e), or (f);
h) a host cell comprising a vector as set forth in (g);
m) a polynucleotide that hybridizes under low, intermediate or high stringency with a polynucleotide sequence as set forth in (a), (b), (c), (d), (e), (f), or (g); or
n) a probe comprising a polynucleotide according to (a), (b), (c), (d), (e), (f), or (g) and, optionally, a label or marker;

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

A homologous polynucleotide or polypeptide sequence, for the purposes of the present invention, encompasses a sequence having a percentage identity with the polynucleotide or polypeptide sequences, set forth herein, of between at least (or at least about) 20.00% to 99.99% (inclusive). The aforementioned range of percent identity is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide. The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266: 383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

Sequence homology and sequence identity can also be determined by hybridization studies under high stringency, intermediate stringency, and/or low stringency. Various degrees of stringency of hybridization can be employed. The more severe the conditions the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] *DNA Probes*, Stockton Press, New York, N.Y., pp. 169-170.

For example, hybridization of immobilized DNA on Southern blots with $^{32}$P-labeled gene-specific probes can be performed by standard methods (Maniatis et al. [1982] *Molecular Cloning. A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5× Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

Tm=81.5° C.+16.6 Log[Na$^+$]+0.41(% G+C)−0.61(% formamide)−600/length of duplex in base pairs.

Washes are typically carried out as follows:

(1) twice at room temperature for 15 minutes in 1×SSPE, 0.1% SDS (low stringency wash);

(2) once at $T_m$−20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5× Denhardt's solution, 0.1% SDS, 0.1 mg/mil denatured DNA. $T_m$ for oligonucleotide probes can be determined by the following formula:

$T_m$(° C.)=2(number T/A base pairs)+4(number G/C base pairs) (Suggs et al. [1981] *ICN-UCLA. Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt,and/or temperature can be altered to change stringency. With a labeled DNA fragment>70 or so bases in length, the following conditions can be used:

| | |
|---|---|
| Low: | 1 or 2× SSPE, room temperature |
| Low: | 1 or 2× SSPE, 42° C. |
| Intermediate: | 0.2× or 1× SSPE, 65° C. |
| High: | 0.1× SSPE, 65° C. |

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512.

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for such fragments, is the total number of nucleotides found in the full-length sequence encoding a particular polypeptide (e.g., a polypeptide such as that of SEQ ID NO: 2). The term "successive" can be interchanged with the term "consecutive" or the phrase "contiguous span". Thus, in some embodiments, a polynucleotide fragment may be referred to as "a contiguous span of at least X nucleotides, wherein X is any integer value beginning with 5; the upper limit for such fragments is one nucleotide less than the total number of nucleotides found in the full-length sequence encoding a particular polypeptide (e.g., a polypeptide comprising SEQ ID NO: 2).

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

The subject invention provides, in one embodiment, methods for the identification of the presence of nucleic acids according to the subject invention in transformed host cells or in cells isolated from an individual suspected of being infected by *A. phagocytophilum*. In these varied embodiments, the invention provides for the detection of nucleic acids in a sample (obtained from the individual or from a cell culture) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system. Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine, et al., *Proc. Natl. Acad. Sci.* 74:5350), 4) magnetic particle separation, 5) nucleic acid or DNA chips, 6) reverse Northern blot assay, 7) dot blot assay, 8) in situ hybridization, 9) RNase protection assay (Melton, et al., *Nuc. Acids Res.* 12.:7035 and as described in the 1998 catalog of Ambion, Inc., Austin, Tex.), 10) ligase chain reaction, 11) polymerase chain reaction (PCR), 12) reverse transcriptase (RT)-PCR (Berchtold, et al., *Nuc. Acids. Res.* 17:453), 13) differential display RT-PCR (DDRT-PCR) or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels, including those set forth below. These methodologies and labels are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a detection, probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of full length polynucleotides or polynucleotides of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (*Science* 270:467-470, 1995; *Proc. Natl. Acad. Sci. U.S.A.* 93:10614-10619, 1996). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

mRNA is isolated from a biological sample and probes are prepared by a single round of reverse transcription. Probes are hybridized to 1 cm² microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the polynucleotides present in a biological sample can also be performed in complementary DNA arrays as described by Pietu et al. (Genome Research 6:492-503, 1996). The polynucleotides of the invention, or fragments thereof, are PCR amplified and spotted on membranes. Then, mRNAs originating from biological samples derived from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, the polynucleotide sequences of to the invention may also be used in analytical systems, such as DNA chips. DNA chips and their uses are well known in the art and (see for example, U.S. Pat. Nos. 5,561,071; 5,753,439; 6,214,545; Schena et al., *BioEssays,* 1996, 18:427-431; Bianchi et al., *Clin. Diagn. Virol.,* 1997, 8:199-208; each of which is hereby incorporated by reference in their entireties) and/or are provided by commercial vendors such as Affymetrix, Inc. (Santa Clara, Calif.). In addition, the nucleic acid sequences of the subject invention can be used as molecular weight markers in nucleic acid analysis procedures.

The subject invention also provides for modified nucleotide sequences. Modified nucleic acid sequences will be understood to mean any nucleotide sequence that has been modified, according to techniques well known to persons skilled in the art, and exhibiting modifications in relation to the native, naturally occurring nucleotide sequences.

The subject invention also provides genetic constructs comprising: a) a polynucleotide sequence encoding a polypeptide comprising SEQ ID No: 2, 3, 4, or a fragment thereof; b) a polynucleotide sequence having at least about 20% to 99.99% identity to a polynucleotide sequence encoding a polypeptide comprising SEQ IDNo: 2, 3, 4, or a fragment of SEQ ID NOs: 2, 3, or 4, wherein said polynucleotide encodes a polypeptide having at least one of the activities or a polypeptide comprising SEQ ID No:2, 3, 4, or a fragment of SEQ ID NOs: 2, 3, or 4; c) a polynucleotide sequence encoding a fragment of a polypeptide comprising SEQ ID No: 2, 3, or 4, wherein said fragment has at least one of the activities of the polypeptide of SEQ ID No: 2, 3, or 4; d) a polynucleotide sequence comprising SEQ ID NO: 1; e) a polynucleotide sequence having at least about 20% to 99.99% identity to the polynucleotide sequence of SEQ ID NO: 1) a polynucleotide sequence encoding variant (e.g., a variant polypeptide) of the polypeptide of SEQ ID No: 2, 3, or 4, wherein said variant has at least one of the activities associated with the polypeptide of SEQ ID NO: 2, 3, or 4; f) a polynucleotide sequence encoding a fragment of a variant polypeptide as set forth in (e); g) a polynucleotide sequence encoding multimeric construct; or h) a polynucleotide that is complementary to the polynucleotides set forth in (a), (b), (c), (d), (e), (f), or (g). Genetic constructs of the subject invention can also contain additional regulatory elements such as promoters and enhancers and, optionally, selectable markers. In one aspect of the subject invention, the genetic construct comprises a promoter operably linked to a polynucleotide sequence encoding the signal peptide identified in SEQ ID NO: 5 which is operably linked to a polynucleotide sequence encoding a heterologous polypeptide.

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and a transcriptional and translational termination regions. The transcriptional initiation region, the promoter, may be native or analogous, or foreign or heterologous, to the host cell. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention, including vaccine vectors, can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide, peptide, fragment, or variant encoded by a polynucleotide sequence disclosed herein comprising the culture of a host cell transformed with a polynucleotide of the subject invention under conditions that allow for the expression of the polypeptide and, optionally, recovering the expressed polypeptide.

The disclosed polynucleotide sequences can also be regulated by a second nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV-IE promoter, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes simplex thymidine kinase promoter (Wagner et:al., 1981, Proc. Natl. Acad. Sci. U.S.A. 78:1441-1445), the regulatory sequences of the metallothionein gene" (Brinster et al., 1982, Nature 296:39-42); prokaryotic vectors containing promoters such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., 1983, Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The vectors according to the invention are, for example, vectors of plasmid or viral origin. In a specific embodiment, a vector is used that comprises a promoter operably linked to a protein or peptide-encoding nucleic acid sequence contained within the disclosed polynucleotide sequences, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the polypeptides of the invention include the pET-type plasmid vectors (Promega) or pBAD plasmid vectors (Invitrogen) or those provided in the examples below. Furthermore, the vectors according to the invention are useful for transforming host cells so as to clone or express the polynucleotide sequences of the invention.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277,375, 5,643,570, or 5,565,335, each of which is incorporated by reference in its entirety, including all references cited within each respective patent.

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

The subject invention also concerns novel compositions that can be employed to elicit an immune response or a protective immune response. In this aspect of the invention, an amount of a composition comprising recombinant DNA or mRNA encoding a polynucleotide of the subject invention sufficient to elicit an immune response or protective immune response is administered to an individual. Signal sequences may be deleted from the nucleic acid encoding an antigen, of interest and the individual may be monitored for the induction of an immune response according to methods known in the art. A "protective immune response" or "therapeutic immune response" refers to a CTL (or CD8$^+$ T cell) and/or an HTL (or CD4$^+$ T cell) response to an antigen that, in some way, prevents or at least partially arrests disease symptoms, side effects or progression. The immune response may also include an antibody response that has been facilitated by the stimulation of helper T cells.

In another embodiment, the subject invention further comprises the administration of polynucleotide vaccines in conjunction with a polypeptide antigen, or composition thereof, of the invention. In a preferred embodiment, the antigen is the polypeptide that is encoded by the polynucleotide administered as the polynucleotide vaccine. As a particularly preferred embodiment, the polypeptide antigen is administered as a booster subsequent to the initial administration of the polynucleotide vaccine.

A further embodiment of the subject invention provides for the induction of an immune response to the novel *A. phagocytophilum* antigens disclosed herein (see, for example, the antigens and peptides set forth in the Tables and Sequence Listing attached hereto) using a "prime-boost" vaccination regimen known to those skilled in the art. In this aspect of the invention, a DNA vaccine or polypeptide antigen of the subject invention is administered to an individual in an amount sufficient to "prime" the immune response of the individual. The immune response of the individual is then "boosted" via the administration of: 1) one or a combination of: a peptide, polypeptide, and/or full length polypeptide antigen of the subject invention (optionally in conjunction with a immunostimulatory molecule and/or an adjuvant); or 2) a viral vector that contains nucleic acid encoding one, or more, of the same or, optionally, different, antigens, multi-epitope constructs, and/or peptide antigens set forth herein. In some alternative embodiments of the, invention, a gene encoding an immunostimulatory molecule may be incorporated into the viral vector used to "boost the immune response of the individual. Exemplary immunostimulatory molecules include, and are not limited to, IL-1, IL-2, IL-3, IL-4, IL-5, IL-6, IL-7, IL-8, IL-9, IL-10, IL-11, IL-15, Il-16, Il-18, IL-23, IL-24, erythropoietin, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); vascular endothelial growth factor (VEGF); interferons (e.g., IFN-γ, IFN-α, IFN-β); leukemia inhibitory factor (LIF); ciliary neurotrophic factor (CNTF); oncostatin M; stem cell factor (SCF); transforming growth factors (e.g., TGF-α, TGF-β1, TGF-β1, TGF-β1), or chemokines (such as, but not limited to, BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROβ, MIP-3α/Exodus/LARC, MIP-3β/Exodus-3/ELC, MIP-4/PARC/DC-CK1, PF-4, RANTES, SDF1α, TARC, or TECK). Genes encoding these immunostimulatory molecules are known to those skilled in the art and coding sequences may be obtained from a variety of sources, including various patents databases, publicly available databases (such as the nucleic acid and protein databases found at the National Library of Medicine or the European Molecular Biology Laboratory), the scientific literature, or scientific literature cited in catalogs produced by companies such as Genzyme, Inc., R&D Systems, Inc, or InvivoGen, Inc. [see, for example, the 1995 Cytokine Research Products catalog, Genzyme Diagnostics, Genzyme Corporation, Cambridge Mass.; 2002 or 1995 Catalog of R&D Systems, Inc (Minneapolis, Minn.); or 2002 Catalog of InvivoGen, Inc (San Diego, Calif.) each of which is incorporated by reference in its entirety, including all references cited therein].

Methods of introducing DNA vaccines into individuals are well-known to the skilled artisan. For example, DNA can be injected into skeletal muscle or other somatic tissues (e.g., intramuscular injection). Cationic liposomes or biolistic devices, such as a gene gun, can be used to deliver DNA vaccines. Alternatively, iontophoresis and other means for transdermal transmission can be used for the introduction of DNA vaccines into an individual.

Viral vectors for use in the subject invention can have a portion of the viral genome is deleted to introduce new genes without destroying infectivity of the virus. The viral vector of the present invention is, typically, a non-pathogenic virus. At the option of the practitioner, the viral vector can be selected so as to infect a specific cell type, such as professional antigen presenting cells (e.g., macrophage or dendritic cells). Alternatively, a viral vector can be selected that is able to infect any cell in the individual. Exemplary viral vectors suitable for use in the present invention include, but are not limited to poxvirus such as vaccinia virus, avipox virus, fowlpox virus, a highly attenuated vaccinia virus (such as Ankara or MVA [Modified Vaccinia Ankara]), retrovirus, adenovirus baculovirus and the like. In a preferred embodiment, the viral vector is Ankara or MVA.

General strategies for construction of vaccinia virus expression vectors are known in the art (see, for example, Smith and Moss Bio Techniques November/December, 306-312, 1984; U.S. Pat. No. 4,738,846 (hereby incorporated by reference in its entirety). Sutter and Moss (Proc. Nat'l. Acad. Sci U.S.A. 89:10847-10851, 1992) and Sutter et al. (Vaccine, 12(11):1032-40, 1994) disclose the construction and use as a vector, a non-replicating recombinant Ankara virus (MVA) which can be used as a viral vector in the present invention.

Compositions comprising the subject polynucleotides can include appropriate nucleic acid vaccine vectors (plasmids), which are commercially available (e.g., Vical, San Diego, Calif.) or other nucleic acid vectors (plasmids), which are also commercially available (e.g., Valenti, Burlingame, Calif.). Alternatively, compositions comprising viral vectors and polynucleotides according to the subject invention are provided by the subject invention. In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science*, Mack Publishing Company, Easton, Pa.

The subject invention also provides an assay that comprises the use of polynucleotides, as set forth herein, for the detection of *Anaplasma phagocytophilum*. In certain preferred embodiments, the polynucleotides used in the assay methods does not hybridize with a polynucleotide sequence from *Anaplasma marginale, Anaplasma centrale, Ehrlichia canis, Ehrlichia chaffeensis*, or *Cowdria ruminantium*. Some aspects of the invention provide for a method that comprises contacting a sample comprising a population of polynucleotides with a second population of polynucleotides under conditions that allow for the formation of an hybridization complex, wherein said second population of polynucleotides comprises polynucleotides that encode at least one polypeptide that is selected from the group consisting of: a) SEQ ID NO 2; b) SEQ ID NO: 3; c) SEQ ID NO: 4; d) fragments of SEQ ID NOs: 2, 3, or 4; e) a polypeptide as set forth in Tables 1 or 2 or 3; f) a variant polypeptide of SEQ ID NO: 2, 3, or 4, wherein said variant polypeptide specifically binds to an antibody that specifically binds to a polypeptide of SEQ ID NO: 2, 3, or 4; g) a variant polypeptide fragment of SEQ ID NO: 2, 3, or 4, wherein said variant polypeptide fragment specifically binds to an antibody that specifically binds to a polypeptide of SEQ ID NO: 2, 3, or 4 or a fragment of SEQ ID NO: 2, 3, or 4; h) a variant of a polypeptide as set forth in Tables 1-3, wherein said variant polypeptide specifically binds to an antibody that specifically binds to a polypeptide of SEQ ID NO: 2, 3, or 4 or a polypeptide as set forth in Table 1, 2 or 3; i) a heterologous polypeptide fused, in frame, to a polypeptide comprising: 1) SEQ ID NO: 2, 3, or 4; 2) fragments of SEQ ID NO: 2, 3, or 4; or 3) a polypeptide as set forth in Tables 1, 2 or 3; and j) mixtures of polypeptides as set forth in a), b), c), d), e), f), g), h), or i). The method can further comprise the step of detecting the hybridization complex and the second population of polynucleotides can be an array of polynucleotides or the same or different sequence if desired. Some aspects of the invention provide for the use of polynucleotides that do not hybridize with a polynucleotide sequence from *Anaplasma marginale, Anaplasma centrale, Ehrlichia canis, Ehrlichia chaffeensis*, or *Cowdria ruminantium*.

TABLE 1

| N-terminal amino acid position | C-terminal amino acid position |
|---|---|
| 5-mer peptides of SEQ ID NO:2 | |
| 1 | 5 |
| 2 | 6 |
| 3 | 7 |
| 4 | 8 |
| 5 | 9 |
| 6 | 10 |
| 7 | 11 |
| 8 | 12 |
| 9 | 13 |
| 10 | 14 |
| 11 | 15 |
| 12 | 16 |
| 13 | 17 |
| 14 | 18 |
| 15 | 19 |
| 16 | 20 |
| 17 | 21 |
| 18 | 22 |
| 19 | 23 |
| 20 | 24 |
| 21 | 25 |
| 22 | 26 |
| 23 | 27 |
| 24 | 28 |
| 25 | 29 |
| 26 | 30 |
| 27 | 31 |
| 28 | 32 |
| 29 | 33 |
| 30 | 34 |
| 31 | 35 |
| 32 | 36 |
| 33 | 37 |
| 34 | 38 |
| 35 | 39 |
| 36 | 40 |
| 37 | 41 |
| 38 | 42 |
| 39 | 43 |
| 40 | 44 |
| 41 | 45 |
| 42 | 46 |
| 43 | 47 |
| 44 | 48 |
| 45 | 49 |
| 46 | 50 |
| 47 | 51 |
| 48 | 52 |
| 49 | 53 |
| 50 | 54 |
| 51 | 55 |
| 52 | 56 |
| 53 | 57 |
| 54 | 58 |
| 55 | 59 |
| 56 | 60 |
| 57 | 61 |
| 58 | 62 |
| 59 | 63 |
| 60 | 64 |
| 61 | 65 |
| 62 | 66 |
| 63 | 67 |
| 64 | 68 |
| 65 | 69 |
| 66 | 70 |
| 67 | 71 |
| 68 | 72 |
| 69 | 73 |
| 70 | 74 |

TABLE 1-continued

| N-terminal amino acid position | C-terminal amino acid position |
|---|---|
| 6-mer peptides of SEQ ID NO:2 | |
| 1 | 6 |
| 2 | 7 |
| 3 | 8 |
| 4 | 9 |
| 5 | 10 |
| 6 | 11 |
| 7 | 12 |
| 8 | 13 |
| 9 | 14 |
| 10 | 15 |
| 11 | 16 |
| 12 | 17 |
| 13 | 18 |
| 14 | 19 |
| 15 | 20 |
| 16 | 21 |
| 17 | 22 |
| 18 | 23 |
| 19 | 24 |
| 20 | 25 |
| 21 | 26 |
| 22 | 27 |
| 23 | 28 |
| 24 | 29 |
| 25 | 30 |
| 26 | 31 |
| 27 | 32 |
| 28 | 33 |
| 29 | 34 |
| 30 | 35 |
| 31 | 36 |
| 32 | 37 |
| 33 | 38 |
| 34 | 39 |
| 35 | 40 |
| 36 | 41 |
| 37 | 42 |
| 38 | 43 |
| 39 | 44 |
| 40 | 45 |
| 41 | 46 |
| 42 | 47 |
| 43 | 48 |
| 44 | 49 |
| 45 | 50 |
| 46 | 51 |
| 47 | 52 |
| 48 | 53 |
| 49 | 54 |
| 50 | 55 |
| 51 | 56 |
| 52 | 57 |
| 53 | 58 |
| 54 | 59 |
| 55 | 60 |
| 56 | 61 |
| 57 | 62 |
| 58 | 63 |
| 59 | 64 |
| 60 | 65 |
| 61 | 66 |
| 62 | 67 |
| 63 | 68 |
| 64 | 69 |
| 65 | 70 |
| 66 | 71 |
| 67 | 72 |
| 68 | 73 |
| 69 | 74 |
| 7-mer peptides of SEQ ID NO:2 | |
| 1 | 7 |
| 2 | 8 |
| 3 | 9 |
| 4 | 10 |
| 5 | 11 |
| 6 | 12 |
| 7 | 13 |
| 8 | 14 |
| 9 | 15 |
| 10 | 16 |
| 11 | 17 |
| 12 | 18 |
| 13 | 19 |
| 14 | 20 |
| 15 | 21 |
| 16 | 22 |
| 17 | 23 |
| 18 | 24 |
| 19 | 25 |
| 20 | 26 |
| 21 | 27 |
| 22 | 28 |
| 23 | 29 |
| 24 | 30 |
| 25 | 31 |
| 26 | 32 |
| 27 | 33 |
| 28 | 34 |
| 29 | 35 |
| 30 | 36 |
| 31 | 37 |
| 32 | 38 |
| 33 | 39 |
| 34 | 40 |
| 35 | 41 |
| 36 | 42 |
| 37 | 43 |
| 38 | 44 |
| 39 | 45 |
| 40 | 46 |
| 41 | 47 |
| 42 | 48 |
| 43 | 49 |
| 44 | 50 |
| 45 | 51 |
| 46 | 52 |
| 47 | 53 |
| 48 | 54 |
| 49 | 55 |
| 50 | 56 |
| 51 | 57 |
| 52 | 58 |
| 53 | 59 |
| 54 | 60 |
| 55 | 61 |
| 56 | 62 |
| 57 | 63 |
| 58 | 64 |
| 59 | 65 |
| 60 | 66 |
| 61 | 67 |
| 62 | 68 |
| 63 | 69 |
| 64 | 70 |
| 65 | 71 |
| 66 | 72 |
| 67 | 73 |
| 68 | 74 |
| 8-mer peptides of SEQ ID NO:2 | |
| 1 | 8 |
| 2 | 9 |
| 3 | 10 |
| 4 | 11 |
| 5 | 12 |
| 6 | 13 |
| 7 | 14 |
| 8 | 15 |
| 9 | 16 |

TABLE 1-continued

| N-terminal amino acid position | C-terminal amino acid position |
|---|---|
| 10 | 17 |
| 11 | 18 |
| 12 | 19 |
| 13 | 20 |
| 14 | 21 |
| 15 | 22 |
| 16 | 23 |
| 17 | 24 |
| 18 | 25 |
| 19 | 26 |
| 20 | 27 |
| 21 | 28 |
| 22 | 29 |
| 23 | 30 |
| 24 | 31 |
| 25 | 32 |
| 26 | 33 |
| 27 | 34 |
| 28 | 35 |
| 29 | 36 |
| 30 | 37 |
| 31 | 38 |
| 32 | 39 |
| 33 | 40 |
| 34 | 41 |
| 35 | 42 |
| 36 | 43 |
| 37 | 44 |
| 38 | 45 |
| 39 | 46 |
| 40 | 47 |
| 41 | 48 |
| 42 | 49 |
| 43 | 50 |
| 44 | 51 |
| 45 | 52 |
| 46 | 53 |
| 47 | 54 |
| 48 | 55 |
| 49 | 56 |
| 50 | 57 |
| 51 | 58 |
| 52 | 59 |
| 53 | 60 |
| 54 | 61 |
| 55 | 62 |
| 56 | 63 |
| 57 | 64 |
| 58 | 65 |
| 59 | 66 |
| 60 | 67 |
| 61 | 68 |
| 62 | 69 |
| 63 | 70 |
| 64 | 71 |
| 65 | 72 |
| 66 | 73 |
| 67 | 74 |

9-mer peptides of SEQ ID NO:2

| N-terminal amino acid position | C-terminal amino acid position |
|---|---|
| 1 | 9 |
| 2 | 10 |
| 3 | 11 |
| 4 | 12 |
| 5 | 13 |
| 6 | 14 |
| 7 | 15 |
| 8 | 16 |
| 9 | 17 |
| 10 | 18 |
| 11 | 19 |
| 12 | 20 |
| 13 | 21 |
| 14 | 22 |
| 15 | 23 |
| 16 | 24 |
| 17 | 25 |
| 18 | 26 |
| 19 | 27 |
| 20 | 28 |
| 21 | 29 |
| 22 | 30 |
| 23 | 31 |
| 24 | 32 |
| 25 | 33 |
| 26 | 34 |
| 27 | 35 |
| 28 | 36 |
| 29 | 37 |
| 30 | 38 |
| 31 | 39 |
| 32 | 40 |
| 33 | 41 |
| 34 | 42 |
| 35 | 43 |
| 36 | 44 |
| 37 | 45 |
| 38 | 46 |
| 39 | 47 |
| 40 | 48 |
| 41 | 49 |
| 42 | 50 |
| 43 | 51 |
| 44 | 52 |
| 45 | 53 |
| 46 | 54 |
| 47 | 55 |
| 48 | 56 |
| 49 | 57 |
| 50 | 58 |
| 51 | 59 |
| 52 | 60 |
| 53 | 61 |
| 54 | 62 |
| 55 | 63 |
| 56 | 64 |
| 57 | 65 |
| 58 | 66 |
| 59 | 67 |
| 60 | 68 |
| 61 | 69 |
| 62 | 70 |
| 63 | 71 |
| 64 | 72 |
| 65 | 73 |
| 66 | 74 |

10-mer peptides of SEQ ID NO:2

| N-terminal amino acid position | C-terminal amino acid position |
|---|---|
| 1 | 10 |
| 2 | 11 |
| 3 | 12 |
| 4 | 13 |
| 5 | 14 |
| 6 | 15 |
| 7 | 16 |
| 8 | 17 |
| 9 | 18 |
| 10 | 19 |
| 11 | 20 |
| 12 | 21 |
| 13 | 22 |
| 14 | 23 |
| 15 | 24 |
| 16 | 25 |
| 17 | 26 |
| 18 | 27 |
| 19 | 28 |
| 20 | 29 |
| 21 | 30 |
| 22 | 31 |
| 23 | 32 |
| 24 | 33 |

TABLE 1-continued

| N-terminal amino acid position | C-terminal amino acid position |
|---|---|
| 25 | 34 |
| 26 | 35 |
| 27 | 36 |
| 28 | 37 |
| 29 | 38 |
| 30 | 39 |
| 31 | 40 |
| 32 | 41 |
| 33 | 42 |
| 34 | 43 |
| 35 | 44 |
| 36 | 45 |
| 37 | 46 |
| 38 | 47 |
| 39 | 48 |
| 40 | 49 |
| 41 | 50 |
| 42 | 51 |
| 43 | 52 |
| 44 | 53 |
| 45 | 54 |
| 46 | 55 |
| 47 | 56 |
| 48 | 57 |
| 49 | 58 |
| 50 | 59 |
| 51 | 60 |
| 52 | 61 |
| 53 | 62 |
| 54 | 63 |
| 55 | 64 |
| 56 | 65 |
| 57 | 66 |
| 58 | 67 |
| 59 | 68 |
| 60 | 69 |
| 61 | 70 |
| 62 | 71 |
| 63 | 72 |
| 64 | 73 |
| 65 | 74 |
| 11-mer peptides of SEQ ID NO:2 | |
| 1 | 11 |
| 2 | 12 |
| 3 | 13 |
| 4 | 14 |
| 5 | 15 |
| 6 | 16 |
| 7 | 17 |
| 8 | 18 |
| 9 | 19 |
| 10 | 20 |
| 11 | 21 |
| 12 | 22 |
| 13 | 23 |
| 14 | 24 |
| 15 | 25 |
| 16 | 26 |
| 17 | 27 |
| 18 | 28 |
| 19 | 29 |
| 20 | 30 |
| 21 | 31 |
| 22 | 32 |
| 23 | 33 |
| 24 | 34 |
| 25 | 35 |
| 26 | 36 |
| 27 | 37 |
| 28 | 38 |
| 29 | 39 |
| 30 | 40 |
| 31 | 41 |
| 32 | 42 |
| 33 | 43 |
| 34 | 44 |
| 35 | 45 |
| 36 | 46 |
| 37 | 47 |
| 38 | 48 |
| 39 | 49 |
| 40 | 50 |
| 41 | 51 |
| 42 | 52 |
| 43 | 53 |
| 44 | 54 |
| 45 | 55 |
| 46 | 56 |
| 47 | 57 |
| 48 | 58 |
| 49 | 59 |
| 50 | 60 |
| 51 | 61 |
| 52 | 62 |
| 53 | 63 |
| 54 | 64 |
| 55 | 65 |
| 56 | 66 |
| 57 | 67 |
| 58 | 68 |
| 59 | 69 |
| 60 | 70 |
| 61 | 71 |
| 62 | 72 |
| 63 | 73 |
| 64 | 74 |
| 12-mer peptides of SEQ ID NO:2 | |
| 1 | 12 |
| 2 | 13 |
| 3 | 14 |
| 4 | 15 |
| 5 | 16 |
| 6 | 17 |
| 7 | 18 |
| 8 | 19 |
| 9 | 20 |
| 10 | 21 |
| 11 | 22 |
| 12 | 23 |
| 13 | 24 |
| 14 | 25 |
| 15 | 26 |
| 16 | 27 |
| 17 | 28 |
| 18 | 29 |
| 19 | 30 |
| 20 | 31 |
| 21 | 32 |
| 22 | 33 |
| 23 | 34 |
| 24 | 35 |
| 25 | 36 |
| 26 | 37 |
| 27 | 38 |
| 28 | 39 |
| 29 | 40 |
| 30 | 41 |
| 31 | 42 |
| 32 | 43 |
| 33 | 44 |
| 34 | 45 |
| 35 | 46 |
| 36 | 47 |
| 37 | 48 |
| 38 | 49 |
| 39 | 50 |
| 40 | 51 |
| 41 | 52 |
| 42 | 53 |
| 43 | 54 |

TABLE 1-continued

| N-terminal amino acid position | C-terminal amino acid position |
|---|---|
| 44 | 55 |
| 45 | 56 |
| 46 | 57 |
| 47 | 58 |
| 48 | 59 |
| 49 | 60 |
| 50 | 61 |
| 51 | 62 |
| 52 | 63 |
| 53 | 64 |
| 54 | 65 |
| 55 | 66 |
| 56 | 67 |
| 57 | 68 |
| 58 | 69 |
| 59 | 70 |
| 60 | 71 |
| 61 | 72 |
| 62 | 73 |
| 63 | 74 |
| 13-mer peptides of SEQ ID NO:2 | |
| 1 | 13 |
| 2 | 14 |
| 3 | 15 |
| 4 | 16 |
| 5 | 17 |
| 6 | 18 |
| 7 | 19 |
| 8 | 20 |
| 9 | 21 |
| 10 | 22 |
| 11 | 23 |
| 12 | 24 |
| 13 | 25 |
| 14 | 26 |
| 15 | 27 |
| 16 | 28 |
| 17 | 29 |
| 18 | 30 |
| 19 | 31 |
| 20 | 32 |
| 21 | 33 |
| 22 | 34 |
| 23 | 35 |
| 24 | 36 |
| 25 | 37 |
| 26 | 38 |
| 27 | 39 |
| 28 | 40 |
| 29 | 41 |
| 30 | 42 |
| 31 | 43 |
| 32 | 44 |
| 33 | 45 |
| 34 | 46 |
| 35 | 47 |
| 36 | 48 |
| 37 | 49 |
| 38 | 50 |
| 39 | 51 |
| 40 | 52 |
| 41 | 53 |
| 42 | 54 |
| 43 | 55 |
| 44 | 56 |
| 45 | 57 |
| 46 | 58 |
| 47 | 59 |
| 48 | 60 |
| 49 | 61 |
| 50 | 62 |
| 51 | 63 |
| 52 | 64 |
| 53 | 65 |
| 54 | 66 |
| 55 | 67 |
| 56 | 68 |
| 57 | 69 |
| 58 | 70 |
| 59 | 71 |
| 60 | 72 |
| 61 | 73 |
| 62 | 74 |
| 14-mer peptides of SEQ ID NO:2 | |
| 1 | 14 |
| 2 | 15 |
| 3 | 16 |
| 4 | 17 |
| 5 | 18 |
| 6 | 19 |
| 7 | 20 |
| 8 | 21 |
| 9 | 22 |
| 10 | 23 |
| 11 | 24 |
| 12 | 25 |
| 13 | 26 |
| 14 | 27 |
| 15 | 28 |
| 16 | 29 |
| 17 | 30 |
| 18 | 31 |
| 19 | 32 |
| 20 | 33 |
| 21 | 34 |
| 22 | 35 |
| 23 | 36 |
| 24 | 37 |
| 25 | 38 |
| 26 | 39 |
| 27 | 40 |
| 28 | 41 |
| 29 | 42 |
| 30 | 43 |
| 31 | 44 |
| 32 | 45 |
| 33 | 46 |
| 34 | 47 |
| 35 | 48 |
| 36 | 49 |
| 37 | 50 |
| 38 | 51 |
| 39 | 52 |
| 40 | 53 |
| 41 | 54 |
| 42 | 55 |
| 43 | 56 |
| 44 | 57 |
| 45 | 58 |
| 46 | 59 |
| 47 | 60 |
| 48 | 61 |
| 49 | 62 |
| 50 | 63 |
| 51 | 64 |
| 52 | 65 |
| 53 | 66 |
| 54 | 67 |
| 55 | 68 |
| 56 | 69 |
| 57 | 70 |
| 58 | 71 |
| 59 | 72 |
| 60 | 73 |
| 61 | 74 |
| 15-mer peptides of SEQ ID NO:2 | |
| 1 | 15 |
| 2 | 16 |
| 3 | 17 |

TABLE 1-continued

| N-terminal amino acid position | C-terminal amino acid position |
|---|---|
| 4 | 18 |
| 5 | 19 |
| 6 | 20 |
| 7 | 21 |
| 8 | 22 |
| 9 | 23 |
| 10 | 24 |
| 11 | 25 |
| 12 | 26 |
| 13 | 27 |
| 14 | 28 |
| 15 | 29 |
| 16 | 30 |
| 17 | 31 |
| 18 | 32 |
| 19 | 33 |
| 20 | 34 |
| 21 | 35 |
| 22 | 36 |
| 23 | 37 |
| 24 | 38 |
| 25 | 39 |
| 26 | 40 |
| 27 | 41 |
| 28 | 42 |
| 29 | 43 |
| 30 | 44 |
| 31 | 45 |
| 32 | 46 |
| 33 | 47 |
| 34 | 48 |
| 35 | 49 |
| 36 | 50 |
| 37 | 51 |
| 38 | 52 |
| 39 | 53 |
| 40 | 54 |
| 41 | 55 |
| 42 | 56 |
| 43 | 57 |
| 44 | 58 |
| 45 | 59 |
| 46 | 60 |
| 47 | 61 |
| 48 | 62 |
| 49 | 63 |
| 50 | 64 |
| 51 | 65 |
| 52 | 66 |
| 53 | 67 |
| 54 | 68 |
| 55 | 69 |
| 56 | 70 |
| 57 | 71 |
| 58 | 72 |
| 59 | 73 |
| 60 | 74 |
| 16-mer peptides of SEQ ID NO:2 | |
| 1 | 16 |
| 2 | 17 |
| 3 | 18 |
| 4 | 19 |
| 5 | 20 |
| 6 | 21 |
| 7 | 22 |
| 8 | 23 |
| 9 | 24 |
| 10 | 25 |
| 11 | 26 |
| 12 | 27 |
| 13 | 28 |
| 14 | 29 |
| 15 | 30 |
| 16 | 31 |
| 17 | 32 |

TABLE 1-continued

| N-terminal amino acid position | C-terminal amino acid position |
|---|---|
| 18 | 33 |
| 19 | 34 |
| 20 | 35 |
| 21 | 36 |
| 22 | 37 |
| 23 | 38 |
| 24 | 39 |
| 25 | 40 |
| 26 | 41 |
| 27 | 42 |
| 28 | 43 |
| 29 | 44 |
| 30 | 45 |
| 31 | 46 |
| 32 | 47 |
| 33 | 48 |
| 34 | 49 |
| 35 | 50 |
| 36 | 51 |
| 37 | 52 |
| 38 | 53 |
| 39 | 54 |
| 40 | 55 |
| 41 | 56 |
| 42 | 57 |
| 43 | 58 |
| 44 | 59 |
| 45 | 60 |
| 46 | 61 |
| 47 | 62 |
| 48 | 63 |
| 49 | 64 |
| 50 | 65 |
| 51 | 66 |
| 52 | 67 |
| 53 | 68 |
| 54 | 69 |
| 55 | 70 |
| 56 | 71 |
| 57 | 72 |
| 58 | 73 |
| 59 | 74 |
| 17-mer peptides of SEQ ID NO:2 | |
| 1 | 17 |
| 2 | 18 |
| 3 | 19 |
| 4 | 20 |
| 5 | 21 |
| 6 | 22 |
| 7 | 23 |
| 8 | 24 |
| 9 | 25 |
| 10 | 26 |
| 11 | 27 |
| 12 | 28 |
| 13 | 29 |
| 14 | 30 |
| 15 | 31 |
| 16 | 32 |
| 17 | 33 |
| 18 | 34 |
| 19 | 35 |
| 20 | 36 |
| 21 | 37 |
| 22 | 38 |
| 23 | 39 |
| 24 | 40 |
| 25 | 41 |
| 26 | 42 |
| 27 | 43 |
| 28 | 44 |
| 29 | 45 |
| 30 | 46 |
| 31 | 47 |
| 32 | 48 |

TABLE 1-continued

| N-terminal amino acid position | C-terminal amino acid position |
|---|---|
| 33 | 49 |
| 34 | 50 |
| 35 | 51 |
| 36 | 52 |
| 37 | 53 |
| 38 | 54 |
| 39 | 55 |
| 40 | 56 |
| 41 | 57 |
| 42 | 58 |
| 43 | 59 |
| 44 | 60 |
| 45 | 61 |
| 46 | 62 |
| 47 | 63 |
| 48 | 64 |
| 49 | 65 |
| 50 | 66 |
| 51 | 67 |
| 52 | 68 |
| 53 | 69 |
| 54 | 70 |
| 55 | 71 |
| 56 | 72 |
| 57 | 73 |
| 58 | 74 |

18-mer peptides of SEQ ID NO:2

| N-terminal amino acid position | C-terminal amino acid position |
|---|---|
| 1 | 18 |
| 2 | 19 |
| 3 | 20 |
| 4 | 21 |
| 5 | 22 |
| 6 | 23 |
| 7 | 24 |
| 8 | 25 |
| 9 | 26 |
| 10 | 27 |
| 11 | 28 |
| 12 | 29 |
| 13 | 30 |
| 14 | 31 |
| 15 | 32 |
| 16 | 33 |
| 17 | 34 |
| 18 | 35 |
| 19 | 36 |
| 20 | 37 |
| 21 | 38 |
| 22 | 39 |
| 23 | 40 |
| 24 | 41 |
| 25 | 42 |
| 26 | 43 |
| 27 | 44 |
| 28 | 45 |
| 29 | 46 |
| 30 | 47 |
| 31 | 48 |
| 32 | 49 |
| 33 | 50 |
| 34 | 51 |
| 35 | 52 |
| 36 | 53 |
| 37 | 54 |
| 38 | 55 |
| 39 | 56 |
| 40 | 57 |
| 41 | 58 |
| 42 | 59 |
| 43 | 60 |
| 44 | 61 |
| 45 | 62 |
| 46 | 63 |
| 47 | 64 |
| 48 | 65 |
| 49 | 66 |
| 50 | 67 |
| 51 | 68 |
| 52 | 69 |
| 53 | 70 |
| 54 | 71 |
| 55 | 72 |
| 56 | 73 |
| 57 | 74 |

19-mer peptides of SEQ ID NO:2

| N-terminal amino acid position | C-terminal amino acid position |
|---|---|
| 1 | 19 |
| 2 | 20 |
| 3 | 21 |
| 4 | 22 |
| 5 | 23 |
| 6 | 24 |
| 7 | 25 |
| 8 | 26 |
| 9 | 27 |
| 10 | 28 |
| 11 | 29 |
| 12 | 30 |
| 13 | 31 |
| 14 | 32 |
| 15 | 33 |
| 16 | 34 |
| 17 | 35 |
| 18 | 36 |
| 19 | 37 |
| 20 | 38 |
| 21 | 39 |
| 22 | 40 |
| 23 | 41 |
| 24 | 42 |
| 25 | 43 |
| 26 | 44 |
| 27 | 45 |
| 28 | 46 |
| 29 | 47 |
| 30 | 48 |
| 31 | 49 |
| 32 | 50 |
| 33 | 51 |
| 34 | 52 |
| 35 | 53 |
| 36 | 54 |
| 37 | 55 |
| 38 | 56 |
| 39 | 57 |
| 40 | 58 |
| 41 | 59 |
| 42 | 60 |
| 43 | 61 |
| 44 | 62 |
| 45 | 63 |
| 46 | 64 |
| 47 | 65 |
| 48 | 66 |
| 49 | 67 |
| 50 | 68 |
| 51 | 69 |
| 52 | 70 |
| 53 | 71 |
| 54 | 72 |
| 55 | 73 |
| 56 | 74 |

20-mer peptides of SEQ ID NO:2

| N-terminal amino acid position | C-terminal amino acid position |
|---|---|
| 1 | 20 |
| 2 | 21 |
| 3 | 22 |
| 4 | 23 |
| 5 | 24 |
| 6 | 25 |
| 7 | 26 |

TABLE 1-continued

| N-terminal amino acid position | C-terminal amino acid position |
|---|---|
| 8 | 27 |
| 9 | 28 |
| 10 | 29 |
| 11 | 30 |
| 12 | 31 |
| 13 | 32 |
| 14 | 33 |
| 15 | 34 |
| 16 | 35 |
| 17 | 36 |
| 18 | 37 |
| 19 | 38 |
| 20 | 39 |
| 21 | 40 |
| 22 | 41 |
| 23 | 42 |
| 24 | 43 |
| 25 | 44 |
| 26 | 45 |
| 27 | 46 |
| 28 | 47 |
| 29 | 48 |
| 30 | 49 |
| 31 | 50 |
| 32 | 51 |
| 33 | 52 |
| 34 | 53 |
| 35 | 54 |
| 36 | 55 |
| 37 | 56 |
| 38 | 57 |
| 39 | 58 |
| 40 | 59 |
| 41 | 60 |
| 42 | 61 |
| 43 | 62 |
| 44 | 63 |
| 45 | 64 |
| 46 | 65 |
| 47 | 66 |
| 48 | 67 |
| 49 | 68 |
| 50 | 69 |
| 51 | 70 |
| 52 | 71 |
| 53 | 72 |
| 54 | 73 |
| 55 | 74 |
| 21-mer peptides of SEQ ID NO:2 | |
| 1 | 21 |
| 2 | 22 |
| 3 | 23 |
| 4 | 24 |
| 5 | 25 |
| 6 | 26 |
| 7 | 27 |
| 8 | 28 |
| 9 | 29 |
| 10 | 30 |
| 11 | 31 |
| 12 | 32 |
| 13 | 33 |
| 14 | 34 |
| 15 | 35 |
| 16 | 36 |
| 17 | 37 |
| 18 | 38 |
| 19 | 39 |
| 20 | 40 |
| 21 | 41 |
| 22 | 42 |
| 23 | 43 |
| 24 | 44 |
| 25 | 45 |
| 26 | 46 |
| 27 | 47 |
| 28 | 48 |
| 29 | 49 |
| 30 | 50 |
| 31 | 51 |
| 32 | 52 |
| 33 | 53 |
| 34 | 54 |
| 35 | 55 |
| 36 | 56 |
| 37 | 57 |
| 38 | 58 |
| 39 | 59 |
| 40 | 60 |
| 41 | 61 |
| 42 | 62 |
| 43 | 63 |
| 44 | 64 |
| 45 | 65 |
| 46 | 66 |
| 47 | 67 |
| 48 | 68 |
| 49 | 69 |
| 50 | 70 |
| 51 | 71 |
| 52 | 72 |
| 53 | 73 |
| 54 | 74 |
| 22-mer peptides of SEQ ID NO:2 | |
| 1 | 22 |
| 2 | 23 |
| 3 | 24 |
| 4 | 25 |
| 5 | 26 |
| 6 | 27 |
| 7 | 28 |
| 8 | 29 |
| 9 | 30 |
| 10 | 31 |
| 11 | 32 |
| 12 | 33 |
| 13 | 34 |
| 14 | 35 |
| 15 | 36 |
| 16 | 37 |
| 17 | 38 |
| 18 | 39 |
| 19 | 40 |
| 20 | 41 |
| 21 | 42 |
| 22 | 43 |
| 23 | 44 |
| 24 | 45 |
| 25 | 46 |
| 26 | 47 |
| 27 | 48 |
| 28 | 49 |
| 29 | 50 |
| 30 | 51 |
| 31 | 52 |
| 32 | 53 |
| 33 | 54 |
| 34 | 55 |
| 35 | 56 |
| 36 | 57 |
| 37 | 58 |
| 38 | 59 |
| 39 | 60 |
| 40 | 61 |
| 41 | 62 |
| 42 | 63 |
| 43 | 64 |
| 44 | 65 |
| 45 | 66 |
| 46 | 67 |

TABLE 1-continued

| N-terminal amino acid position | C-terminal amino acid position |
|---|---|
| 47 | 68 |
| 48 | 69 |
| 49 | 70 |
| 50 | 71 |
| 51 | 72 |
| 52 | 73 |
| 53 | 74 |
| 23-mer peptides of SEQ ID NO:2 | |
| 1 | 23 |
| 2 | 24 |
| 3 | 25 |
| 4 | 26 |
| 5 | 27 |
| 6 | 28 |
| 7 | 29 |
| 8 | 30 |
| 9 | 31 |
| 10 | 32 |
| 11 | 33 |
| 12 | 34 |
| 13 | 35 |
| 14 | 36 |
| 15 | 37 |
| 16 | 38 |
| 17 | 39 |
| 18 | 40 |
| 19 | 41 |
| 20 | 42 |
| 21 | 43 |
| 22 | 44 |
| 23 | 45 |
| 24 | 46 |
| 25 | 47 |
| 26 | 48 |
| 27 | 49 |
| 28 | 50 |
| 29 | 51 |
| 30 | 52 |
| 31 | 53 |
| 32 | 54 |
| 33 | 55 |
| 34 | 56 |
| 35 | 57 |
| 36 | 58 |
| 37 | 59 |
| 38 | 60 |
| 39 | 61 |
| 40 | 62 |
| 41 | 63 |
| 42 | 64 |
| 43 | 65 |
| 44 | 66 |
| 45 | 67 |
| 46 | 68 |
| 47 | 69 |
| 48 | 70 |
| 49 | 71 |
| 50 | 72 |
| 51 | 73 |
| 52 | 74 |
| 24-mer peptides of SEQ ID NO:2 | |
| 1 | 24 |
| 2 | 25 |
| 3 | 26 |
| 4 | 27 |
| 5 | 28 |
| 6 | 29 |
| 7 | 30 |
| 8 | 31 |
| 9 | 32 |
| 10 | 33 |
| 11 | 34 |
| 12 | 35 |
| 13 | 36 |
| 14 | 37 |
| 15 | 38 |
| 16 | 39 |
| 17 | 40 |
| 18 | 41 |
| 19 | 42 |
| 20 | 43 |
| 21 | 44 |
| 22 | 45 |
| 23 | 46 |
| 24 | 47 |
| 25 | 48 |
| 26 | 49 |
| 27 | 50 |
| 28 | 51 |
| 29 | 52 |
| 30 | 53 |
| 31 | 54 |
| 32 | 55 |
| 33 | 56 |
| 34 | 57 |
| 35 | 58 |
| 36 | 59 |
| 37 | 60 |
| 38 | 61 |
| 39 | 62 |
| 40 | 63 |
| 41 | 64 |
| 42 | 65 |
| 43 | 66 |
| 44 | 67 |
| 45 | 68 |
| 46 | 69 |
| 47 | 70 |
| 48 | 71 |
| 49 | 72 |
| 50 | 73 |
| 51 | 74 |
| 25-mer peptides of SEQ ID NO:2 | |
| 1 | 25 |
| 2 | 26 |
| 3 | 27 |
| 4 | 28 |
| 5 | 29 |
| 6 | 30 |
| 7 | 31 |
| 8 | 32 |
| 9 | 33 |
| 10 | 34 |
| 11 | 35 |
| 12 | 36 |
| 13 | 37 |
| 14 | 38 |
| 15 | 39 |
| 16 | 40 |
| 17 | 41 |
| 18 | 42 |
| 19 | 43 |
| 20 | 44 |
| 21 | 45 |
| 22 | 46 |
| 23 | 47 |
| 24 | 48 |
| 25 | 49 |
| 26 | 50 |
| 27 | 51 |
| 28 | 52 |
| 29 | 53 |
| 30 | 54 |
| 31 | 55 |
| 32 | 56 |
| 33 | 57 |
| 34 | 58 |
| 35 | 59 |
| 36 | 60 |

TABLE 1-continued

| N-terminal amino acid position | C-terminal amino acid position |
|---|---|
| 37 | 61 |
| 38 | 62 |
| 39 | 63 |
| 40 | 64 |
| 41 | 65 |
| 42 | 66 |
| 43 | 67 |
| 44 | 68 |
| 45 | 69 |
| 46 | 70 |
| 47 | 71 |
| 48 | 72 |
| 49 | 73 |
| 50 | 74 |
| 26-mer peptides of SEQ ID NO:2 | |
| 1 | 26 |
| 2 | 27 |
| 3 | 28 |
| 4 | 29 |
| 5 | 30 |
| 6 | 31 |
| 7 | 32 |
| 8 | 33 |
| 9 | 34 |
| 10 | 35 |
| 11 | 36 |
| 12 | 37 |
| 13 | 38 |
| 14 | 39 |
| 15 | 40 |
| 16 | 41 |
| 17 | 42 |
| 18 | 43 |
| 19 | 44 |
| 20 | 45 |
| 21 | 46 |
| 22 | 47 |
| 23 | 48 |
| 24 | 49 |
| 25 | 50 |
| 26 | 51 |
| 27 | 52 |
| 28 | 53 |
| 29 | 54 |
| 30 | 55 |
| 31 | 56 |
| 32 | 57 |
| 33 | 58 |
| 34 | 59 |
| 35 | 60 |
| 36 | 61 |
| 37 | 62 |
| 38 | 63 |
| 39 | 64 |
| 40 | 65 |
| 41 | 66 |
| 42 | 67 |
| 43 | 68 |
| 44 | 69 |
| 45 | 70 |
| 46 | 71 |
| 47 | 72 |
| 48 | 73 |
| 49 | 74 |
| 27-mer peptides of SEQ ID NO:2 | |
| 1 | 27 |
| 2 | 28 |
| 3 | 29 |
| 4 | 30 |
| 5 | 31 |
| 6 | 32 |
| 7 | 33 |
| 8 | 34 |
| 9 | 35 |

TABLE 1-continued

| N-terminal amino acid position | C-terminal amino acid position |
|---|---|
| 10 | 36 |
| 11 | 37 |
| 12 | 38 |
| 13 | 39 |
| 14 | 40 |
| 15 | 41 |
| 16 | 42 |
| 17 | 43 |
| 18 | 44 |
| 19 | 45 |
| 20 | 46 |
| 21 | 47 |
| 22 | 48 |
| 23 | 49 |
| 24 | 50 |
| 25 | 51 |
| 26 | 52 |
| 27 | 53 |
| 28 | 54 |
| 29 | 55 |
| 30 | 56 |
| 31 | 57 |
| 32 | 58 |
| 33 | 59 |
| 34 | 60 |
| 35 | 61 |
| 36 | 62 |
| 37 | 63 |
| 38 | 64 |
| 39 | 65 |
| 40 | 66 |
| 41 | 67 |
| 42 | 68 |
| 43 | 69 |
| 44 | 70 |
| 45 | 71 |
| 46 | 72 |
| 47 | 73 |
| 48 | 74 |
| 28-mer peptides of SEQ ID NO:2 | |
| 1 | 28 |
| 2 | 29 |
| 3 | 30 |
| 4 | 31 |
| 5 | 32 |
| 6 | 33 |
| 7 | 34 |
| 8 | 35 |
| 9 | 36 |
| 10 | 37 |
| 11 | 38 |
| 12 | 39 |
| 13 | 40 |
| 14 | 41 |
| 15 | 42 |
| 16 | 43 |
| 17 | 44 |
| 18 | 45 |
| 19 | 46 |
| 20 | 47 |
| 21 | 48 |
| 22 | 49 |
| 23 | 50 |
| 24 | 51 |
| 25 | 52 |
| 26 | 53 |
| 27 | 54 |
| 28 | 55 |
| 29 | 56 |
| 30 | 57 |
| 31 | 58 |
| 32 | 59 |
| 33 | 60 |
| 34 | 61 |
| 35 | 62 |

TABLE 1-continued

| N-terminal amino acid position | C-terminal amino acid position |
|---|---|
| 36 | 63 |
| 37 | 64 |
| 38 | 65 |
| 39 | 66 |
| 40 | 67 |
| 41 | 68 |
| 42 | 69 |
| 43 | 70 |
| 44 | 71 |
| 45 | 72 |
| 46 | 73 |
| 47 | 74 |
| 29-mer peptides of SEQ ID NO:2 | |
| 1 | 29 |
| 2 | 30 |
| 3 | 31 |
| 4 | 32 |
| 5 | 33 |
| 6 | 34 |
| 7 | 35 |
| 8 | 36 |
| 9 | 37 |
| 10 | 38 |
| 11 | 39 |
| 12 | 40 |
| 13 | 41 |
| 14 | 42 |
| 15 | 43 |
| 16 | 44 |
| 17 | 45 |
| 18 | 46 |
| 19 | 47 |
| 20 | 48 |
| 21 | 49 |
| 22 | 50 |
| 23 | 51 |
| 24 | 52 |
| 25 | 53 |
| 26 | 54 |
| 27 | 55 |
| 28 | 56 |
| 29 | 57 |
| 30 | 58 |
| 31 | 59 |
| 32 | 60 |
| 33 | 61 |
| 34 | 62 |
| 35 | 63 |
| 36 | 64 |
| 37 | 65 |
| 38 | 66 |
| 39 | 67 |
| 40 | 68 |
| 41 | 69 |
| 42 | 70 |
| 43 | 71 |
| 44 | 72 |
| 45 | 73 |
| 46 | 74 |
| 30-mer peptides of SEQ ID NO:2 | |
| 1 | 30 |
| 2 | 31 |
| 3 | 32 |
| 4 | 33 |
| 5 | 34 |
| 6 | 35 |
| 7 | 36 |
| 8 | 37 |
| 9 | 38 |
| 10 | 39 |
| 11 | 40 |
| 12 | 41 |
| 13 | 42 |
| 14 | 43 |

TABLE 1-continued

| N-terminal amino acid position | C-terminal amino acid position |
|---|---|
| 15 | 44 |
| 16 | 45 |
| 17 | 46 |
| 18 | 47 |
| 19 | 48 |
| 20 | 49 |
| 21 | 50 |
| 22 | 51 |
| 23 | 52 |
| 24 | 53 |
| 25 | 54 |
| 26 | 55 |
| 27 | 56 |
| 28 | 57 |
| 29 | 58 |
| 30 | 59 |
| 31 | 60 |
| 32 | 61 |
| 33 | 62 |
| 34 | 63 |
| 35 | 64 |
| 36 | 65 |
| 37 | 66 |
| 38 | 67 |
| 39 | 68 |
| 40 | 69 |
| 41 | 70 |
| 42 | 71 |
| 43 | 72 |
| 44 | 73 |
| 45 | 74 |
| 31-mer peptides of SEQ ID NO:2 | |
| 1 | 31 |
| 2 | 32 |
| 3 | 33 |
| 4 | 34 |
| 5 | 35 |
| 6 | 36 |
| 7 | 37 |
| 8 | 38 |
| 9 | 39 |
| 10 | 40 |
| 11 | 41 |
| 12 | 42 |
| 13 | 43 |
| 14 | 44 |
| 15 | 45 |
| 16 | 46 |
| 17 | 47 |
| 18 | 48 |
| 19 | 49 |
| 20 | 50 |
| 21 | 51 |
| 22 | 52 |
| 23 | 53 |
| 24 | 54 |
| 25 | 55 |
| 26 | 56 |
| 27 | 57 |
| 28 | 58 |
| 29 | 59 |
| 30 | 60 |
| 31 | 61 |
| 32 | 62 |
| 33 | 63 |
| 34 | 64 |
| 35 | 65 |
| 36 | 66 |
| 37 | 67 |
| 38 | 68 |
| 39 | 69 |
| 40 | 70 |
| 41 | 71 |
| 42 | 72 |
| 43 | 73 |

TABLE 1-continued

| N-terminal amino acid position | C-terminal amino acid position |
|---|---|
| 44 | 74 |
| 32-mer peptides of SEQ ID NO:2 | |
| 1 | 32 |
| 2 | 33 |
| 3 | 34 |
| 4 | 35 |
| 5 | 36 |
| 6 | 37 |
| 7 | 38 |
| 8 | 39 |
| 9 | 40 |
| 10 | 41 |
| 11 | 42 |
| 12 | 43 |
| 13 | 44 |
| 14 | 45 |
| 15 | 46 |
| 16 | 47 |
| 17 | 48 |
| 18 | 49 |
| 19 | 50 |
| 20 | 51 |
| 21 | 52 |
| 22 | 53 |
| 23 | 54 |
| 24 | 55 |
| 25 | 56 |
| 26 | 57 |
| 27 | 58 |
| 28 | 59 |
| 29 | 60 |
| 30 | 61 |
| 31 | 62 |
| 32 | 63 |
| 33 | 64 |
| 34 | 65 |
| 35 | 66 |
| 36 | 67 |
| 37 | 68 |
| 38 | 69 |
| 39 | 70 |
| 40 | 71 |
| 41 | 72 |
| 42 | 73 |
| 43 | 74 |
| 33-mer peptides of SEQ ID NO:2 | |
| 1 | 33 |
| 2 | 34 |
| 3 | 35 |
| 4 | 36 |
| 5 | 37 |
| 6 | 38 |
| 7 | 39 |
| 8 | 40 |
| 9 | 41 |
| 10 | 42 |
| 11 | 43 |
| 12 | 44 |
| 13 | 45 |
| 14 | 46 |
| 15 | 47 |
| 16 | 48 |
| 17 | 49 |
| 18 | 50 |
| 19 | 51 |
| 20 | 52 |
| 21 | 53 |
| 22 | 54 |
| 23 | 55 |
| 24 | 56 |
| 25 | 57 |
| 26 | 58 |
| 27 | 59 |
| 28 | 60 |
| 29 | 61 |
| 30 | 62 |
| 31 | 63 |
| 32 | 64 |
| 33 | 65 |
| 34 | 66 |
| 35 | 67 |
| 36 | 68 |
| 37 | 69 |
| 38 | 70 |
| 39 | 71 |
| 40 | 72 |
| 41 | 73 |
| 42 | 74 |
| 34-mer peptides of SEQ ID NO:2 | |
| 1 | 34 |
| 2 | 35 |
| 3 | 36 |
| 4 | 37 |
| 5 | 38 |
| 6 | 39 |
| 7 | 40 |
| 8 | 41 |
| 9 | 42 |
| 10 | 43 |
| 11 | 44 |
| 12 | 45 |
| 13 | 46 |
| 14 | 47 |
| 15 | 48 |
| 16 | 49 |
| 17 | 50 |
| 18 | 51 |
| 19 | 52 |
| 20 | 53 |
| 21 | 54 |
| 22 | 55 |
| 23 | 56 |
| 24 | 57 |
| 25 | 58 |
| 26 | 59 |
| 27 | 60 |
| 28 | 61 |
| 29 | 62 |
| 30 | 63 |
| 31 | 64 |
| 32 | 65 |
| 33 | 66 |
| 34 | 67 |
| 35 | 68 |
| 36 | 69 |
| 37 | 70 |
| 38 | 71 |
| 39 | 72 |
| 40 | 73 |
| 41 | 74 |
| 35-mer peptides of SEQ ID NO:2 | |
| 1 | 35 |
| 2 | 36 |
| 3 | 37 |
| 4 | 38 |
| 5 | 39 |
| 6 | 40 |
| 7 | 41 |
| 8 | 42 |
| 9 | 43 |
| 10 | 44 |
| 11 | 45 |
| 12 | 46 |
| 13 | 47 |
| 14 | 48 |
| 15 | 49 |
| 16 | 50 |
| 17 | 51 |

TABLE 1-continued

| N-terminal amino acid position | C-terminal amino acid position |
|---|---|
| 18 | 52 |
| 19 | 53 |
| 20 | 54 |
| 21 | 55 |
| 22 | 56 |
| 23 | 57 |
| 24 | 58 |
| 25 | 59 |
| 26 | 60 |
| 27 | 61 |
| 28 | 62 |
| 29 | 63 |
| 30 | 64 |
| 31 | 65 |
| 32 | 66 |
| 33 | 67 |
| 34 | 68 |
| 35 | 69 |
| 36 | 70 |
| 37 | 71 |
| 38 | 72 |
| 39 | 73 |
| 40 | 74 |
| 36-mer peptides of SEQ ID NO:2 | |
| 1 | 36 |
| 2 | 37 |
| 3 | 38 |
| 4 | 39 |
| 5 | 40 |
| 6 | 41 |
| 7 | 42 |
| 8 | 43 |
| 9 | 44 |
| 10 | 45 |
| 11 | 46 |
| 12 | 47 |
| 13 | 48 |
| 14 | 49 |
| 15 | 50 |
| 16 | 51 |
| 17 | 52 |
| 18 | 53 |
| 19 | 54 |
| 20 | 55 |
| 21 | 56 |
| 22 | 57 |
| 23 | 58 |
| 24 | 59 |
| 25 | 60 |
| 26 | 61 |
| 27 | 62 |
| 28 | 63 |
| 29 | 64 |
| 30 | 65 |
| 31 | 66 |
| 32 | 67 |
| 33 | 68 |
| 34 | 69 |
| 35 | 70 |
| 36 | 71 |
| 37 | 72 |
| 38 | 73 |
| 39 | 74 |
| 37-mer peptides of SEQ ID NO:2 | |
| 1 | 37 |
| 2 | 38 |
| 3 | 39 |
| 4 | 40 |
| 5 | 41 |
| 6 | 42 |
| 7 | 43 |
| 8 | 44 |
| 9 | 45 |
| 10 | 46 |
| 11 | 47 |
| 12 | 48 |
| 13 | 49 |
| 14 | 50 |
| 15 | 51 |
| 16 | 52 |
| 17 | 53 |
| 18 | 54 |
| 19 | 55 |
| 20 | 56 |
| 21 | 57 |
| 22 | 58 |
| 23 | 59 |
| 24 | 60 |
| 25 | 61 |
| 26 | 62 |
| 27 | 63 |
| 28 | 64 |
| 29 | 65 |
| 30 | 66 |
| 31 | 67 |
| 32 | 68 |
| 33 | 69 |
| 34 | 70 |
| 35 | 71 |
| 36 | 72 |
| 37 | 73 |
| 38 | 74 |
| 38-mer peptides of SEQ ID NO:2 | |
| 1 | 38 |
| 2 | 39 |
| 3 | 40 |
| 4 | 41 |
| 5 | 42 |
| 6 | 43 |
| 7 | 44 |
| 8 | 45 |
| 9 | 46 |
| 10 | 47 |
| 11 | 48 |
| 12 | 49 |
| 13 | 50 |
| 14 | 51 |
| 15 | 52 |
| 16 | 53 |
| 17 | 54 |
| 18 | 55 |
| 19 | 56 |
| 20 | 57 |
| 21 | 58 |
| 22 | 59 |
| 23 | 60 |
| 24 | 61 |
| 25 | 62 |
| 26 | 63 |
| 27 | 64 |
| 28 | 65 |
| 29 | 66 |
| 30 | 67 |
| 31 | 68 |
| 32 | 69 |
| 33 | 70 |
| 34 | 71 |
| 35 | 72 |
| 36 | 73 |
| 37 | 74 |
| 39-mer peptides of SEQ ID NO:2 | |
| 1 | 39 |
| 2 | 40 |
| 3 | 41 |
| 4 | 42 |
| 5 | 43 |
| 6 | 44 |
| 7 | 45 |

TABLE 1-continued

| N-terminal amino acid position | C-terminal amino acid position |
|---|---|
| 8 | 46 |
| 9 | 47 |
| 10 | 48 |
| 11 | 49 |
| 12 | 50 |
| 13 | 51 |
| 14 | 52 |
| 15 | 53 |
| 16 | 54 |
| 17 | 55 |
| 18 | 56 |
| 19 | 57 |
| 20 | 58 |
| 21 | 59 |
| 22 | 60 |
| 23 | 61 |
| 24 | 62 |
| 25 | 63 |
| 26 | 64 |
| 27 | 65 |
| 28 | 66 |
| 29 | 67 |
| 30 | 68 |
| 31 | 69 |
| 32 | 70 |
| 33 | 71 |
| 34 | 72 |
| 35 | 73 |
| 36 | 74 |
| 40-mer peptides of SEQ ID NO:2 | |
| 1 | 40 |
| 2 | 41 |
| 3 | 42 |
| 4 | 43 |
| 5 | 44 |
| 6 | 45 |
| 7 | 46 |
| 8 | 47 |
| 9 | 48 |
| 10 | 49 |
| 11 | 50 |
| 12 | 51 |
| 13 | 52 |
| 14 | 53 |
| 15 | 54 |
| 16 | 55 |
| 17 | 56 |
| 18 | 57 |
| 19 | 58 |
| 20 | 59 |
| 21 | 60 |
| 22 | 61 |
| 23 | 62 |
| 24 | 63 |
| 25 | 64 |
| 26 | 65 |
| 27 | 66 |
| 28 | 67 |
| 29 | 68 |
| 30 | 69 |
| 31 | 70 |
| 32 | 71 |
| 33 | 72 |
| 34 | 73 |
| 35 | 74 |
| 41-mer peptides of SEQ ID NO:2 | |
| 1 | 41 |
| 2 | 42 |
| 3 | 43 |
| 4 | 44 |
| 5 | 45 |
| 6 | 46 |
| 7 | 47 |
| 8 | 48 |
| 9 | 49 |
| 10 | 50 |
| 11 | 51 |
| 12 | 52 |
| 13 | 53 |
| 14 | 54 |
| 15 | 55 |
| 16 | 56 |
| 17 | 57 |
| 18 | 58 |
| 19 | 59 |
| 20 | 60 |
| 21 | 61 |
| 22 | 62 |
| 23 | 63 |
| 24 | 64 |
| 25 | 65 |
| 26 | 66 |
| 27 | 67 |
| 28 | 68 |
| 29 | 69 |
| 30 | 70 |
| 31 | 71 |
| 32 | 72 |
| 33 | 73 |
| 34 | 74 |
| 42-mer peptides of SEQ ID NO:2 | |
| 1 | 42 |
| 2 | 43 |
| 3 | 44 |
| 4 | 45 |
| 5 | 46 |
| 6 | 47 |
| 7 | 48 |
| 8 | 49 |
| 9 | 50 |
| 10 | 51 |
| 11 | 52 |
| 12 | 53 |
| 13 | 54 |
| 14 | 55 |
| 15 | 56 |
| 16 | 57 |
| 17 | 58 |
| 18 | 59 |
| 19 | 60 |
| 20 | 61 |
| 21 | 62 |
| 22 | 63 |
| 23 | 64 |
| 24 | 65 |
| 25 | 66 |
| 26 | 67 |
| 27 | 68 |
| 28 | 69 |
| 29 | 70 |
| 30 | 71 |
| 31 | 72 |
| 32 | 73 |
| 33 | 74 |
| 43-mer peptides of SEQ ID NO:2 | |
| 1 | 43 |
| 2 | 44 |
| 3 | 45 |
| 4 | 46 |
| 5 | 47 |
| 6 | 48 |
| 7 | 49 |
| 8 | 50 |
| 9 | 51 |
| 10 | 52 |
| 11 | 53 |
| 12 | 54 |
| 13 | 55 |

TABLE 1-continued

| N-terminal amino acid position | C-terminal amino acid position |
|---|---|
| 14 | 56 |
| 15 | 57 |
| 16 | 58 |
| 17 | 59 |
| 18 | 60 |
| 19 | 61 |
| 20 | 62 |
| 21 | 63 |
| 22 | 64 |
| 23 | 65 |
| 24 | 66 |
| 25 | 67 |
| 26 | 68 |
| 27 | 69 |
| 28 | 70 |
| 29 | 71 |
| 30 | 72 |
| 31 | 73 |
| 32 | 74 |
| 44-mer peptides of SEQ ID NO:2 | |
| 1 | 44 |
| 2 | 45 |
| 3 | 46 |
| 4 | 47 |
| 5 | 48 |
| 6 | 49 |
| 7 | 50 |
| 8 | 51 |
| 9 | 52 |
| 10 | 53 |
| 11 | 54 |
| 12 | 55 |
| 13 | 56 |
| 14 | 57 |
| 15 | 58 |
| 16 | 59 |
| 17 | 60 |
| 18 | 61 |
| 19 | 62 |
| 20 | 63 |
| 21 | 64 |
| 22 | 65 |
| 23 | 66 |
| 24 | 67 |
| 25 | 68 |
| 26 | 69 |
| 27 | 70 |
| 28 | 71 |
| 29 | 72 |
| 30 | 73 |
| 31 | 74 |
| 45-mer peptides of SEQ ID NO:2 | |
| 1 | 45 |
| 2 | 46 |
| 3 | 47 |
| 4 | 48 |
| 5 | 49 |
| 6 | 50 |
| 7 | 51 |
| 8 | 52 |
| 9 | 53 |
| 10 | 54 |
| 11 | 55 |
| 12 | 56 |
| 13 | 57 |
| 14 | 58 |
| 15 | 59 |
| 16 | 60 |
| 17 | 61 |
| 18 | 62 |
| 19 | 63 |
| 20 | 64 |
| 21 | 65 |
| 22 | 66 |

TABLE 1-continued

| N-terminal amino acid position | C-terminal amino acid position |
|---|---|
| 23 | 67 |
| 24 | 68 |
| 25 | 69 |
| 26 | 70 |
| 27 | 71 |
| 28 | 72 |
| 29 | 73 |
| 30 | 74 |
| 46-mer peptides of SEQ ID NO:2 | |
| 1 | 46 |
| 2 | 47 |
| 3 | 48 |
| 4 | 49 |
| 5 | 50 |
| 6 | 51 |
| 7 | 52 |
| 8 | 53 |
| 9 | 54 |
| 10 | 55 |
| 11 | 56 |
| 12 | 57 |
| 13 | 58 |
| 14 | 59 |
| 15 | 60 |
| 16 | 61 |
| 17 | 62 |
| 18 | 63 |
| 19 | 64 |
| 20 | 65 |
| 21 | 66 |
| 22 | 67 |
| 23 | 68 |
| 24 | 69 |
| 25 | 70 |
| 26 | 71 |
| 27 | 72 |
| 28 | 73 |
| 29 | 74 |
| 47-mer peptides of SEQ ID NO:2 | |
| 1 | 47 |
| 2 | 48 |
| 3 | 49 |
| 4 | 50 |
| 5 | 51 |
| 6 | 52 |
| 7 | 53 |
| 8 | 54 |
| 9 | 55 |
| 10 | 56 |
| 11 | 57 |
| 12 | 58 |
| 13 | 59 |
| 14 | 60 |
| 15 | 61 |
| 16 | 62 |
| 17 | 63 |
| 18 | 64 |
| 19 | 65 |
| 20 | 66 |
| 21 | 67 |
| 22 | 68 |
| 23 | 69 |
| 24 | 70 |
| 25 | 71 |
| 26 | 72 |
| 27 | 73 |
| 28 | 74 |
| 48-mer peptides of SEQ ID NO:2 | |
| 1 | 48 |
| 2 | 49 |
| 3 | 50 |
| 4 | 51 |
| 5 | 52 |

TABLE 1-continued

| N-terminal amino acid position | C-terminal amino acid position |
|---|---|
| 6 | 53 |
| 7 | 54 |
| 8 | 55 |
| 9 | 56 |
| 10 | 57 |
| 11 | 58 |
| 12 | 59 |
| 13 | 60 |
| 14 | 61 |
| 15 | 62 |
| 16 | 63 |
| 17 | 64 |
| 18 | 65 |
| 19 | 66 |
| 20 | 67 |
| 21 | 68 |
| 22 | 69 |
| 23 | 70 |
| 24 | 71 |
| 25 | 72 |
| 26 | 73 |
| 27 | 74 |
| 49-mer peptides of SEQ ID NO:2 | |
| 1 | 49 |
| 2 | 50 |
| 3 | 51 |
| 4 | 52 |
| 5 | 53 |
| 6 | 54 |
| 7 | 55 |
| 8 | 56 |
| 9 | 57 |
| 10 | 58 |
| 11 | 59 |
| 12 | 60 |
| 13 | 61 |
| 14 | 62 |
| 15 | 63 |
| 16 | 64 |
| 17 | 65 |
| 18 | 66 |
| 19 | 67 |
| 20 | 68 |
| 21 | 69 |
| 22 | 70 |
| 23 | 71 |
| 24 | 72 |
| 25 | 73 |
| 26 | 74 |
| 50-mer peptides of SEQ ID NO:2 | |
| 1 | 50 |
| 2 | 51 |
| 3 | 52 |
| 4 | 53 |
| 5 | 54 |
| 6 | 55 |
| 7 | 56 |
| 8 | 57 |
| 9 | 58 |
| 10 | 59 |
| 11 | 60 |
| 12 | 61 |
| 13 | 62 |
| 14 | 63 |
| 15 | 64 |
| 16 | 65 |
| 17 | 66 |
| 18 | 67 |
| 19 | 68 |
| 20 | 69 |
| 21 | 70 |
| 22 | 71 |
| 23 | 72 |
| 24 | 73 |

TABLE 1-continued

| N-terminal amino acid position | C-terminal amino acid position |
|---|---|
| 25 | 74 |
| 51-mer peptides of SEQ ID NO:2 | |
| 1 | 51 |
| 2 | 52 |
| 3 | 53 |
| 4 | 54 |
| 5 | 55 |
| 6 | 56 |
| 7 | 57 |
| 8 | 58 |
| 9 | 59 |
| 10 | 60 |
| 11 | 61 |
| 12 | 62 |
| 13 | 63 |
| 14 | 64 |
| 15 | 65 |
| 16 | 66 |
| 17 | 67 |
| 18 | 68 |
| 19 | 69 |
| 20 | 70 |
| 21 | 71 |
| 22 | 72 |
| 23 | 73 |
| 24 | 74 |
| 52-mer peptides of SEQ ID NO:2 | |
| 1 | 52 |
| 2 | 53 |
| 3 | 54 |
| 4 | 55 |
| 5 | 56 |
| 6 | 57 |
| 7 | 58 |
| 8 | 59 |
| 9 | 60 |
| 10 | 61 |
| 11 | 62 |
| 12 | 63 |
| 13 | 64 |
| 14 | 65 |
| 15 | 66 |
| 16 | 67 |
| 17 | 68 |
| 18 | 69 |
| 19 | 70 |
| 20 | 71 |
| 21 | 72 |
| 22 | 73 |
| 23 | 74 |
| 53-mer peptides of SEQ ID NO:2 | |
| 1 | 53 |
| 2 | 54 |
| 3 | 55 |
| 4 | 56 |
| 5 | 57 |
| 6 | 58 |
| 7 | 59 |
| 8 | 60 |
| 9 | 61 |
| 10 | 62 |
| 11 | 63 |
| 12 | 64 |
| 13 | 65 |
| 14 | 66 |
| 15 | 67 |
| 16 | 68 |
| 17 | 69 |
| 18 | 70 |
| 19 | 71 |
| 20 | 72 |
| 21 | 73 |
| 22 | 74 |

TABLE 1-continued

| N-terminal amino acid position | C-terminal amino acid position |
|---|---|
| 54-mer peptides of SEQ ID NO:2 | |
| 1 | 54 |
| 2 | 55 |
| 3 | 56 |
| 4 | 57 |
| 5 | 58 |
| 6 | 59 |
| 7 | 60 |
| 8 | 61 |
| 9 | 62 |
| 10 | 63 |
| 11 | 64 |
| 12 | 65 |
| 13 | 66 |
| 14 | 67 |
| 15 | 68 |
| 16 | 69 |
| 17 | 70 |
| 18 | 71 |
| 19 | 72 |
| 20 | 73 |
| 21 | 74 |
| 55-mer peptides of SEQ ID NO:2 | |
| 1 | 55 |
| 2 | 56 |
| 3 | 57 |
| 4 | 58 |
| 5 | 59 |
| 6 | 60 |
| 7 | 61 |
| 8 | 62 |
| 9 | 63 |
| 10 | 64 |
| 11 | 65 |
| 12 | 66 |
| 13 | 67 |
| 14 | 68 |
| 15 | 69 |
| 16 | 70 |
| 17 | 71 |
| 18 | 72 |
| 19 | 73 |
| 20 | 74 |
| 56-mer peptides of SEQ ID NO:2 | |
| 1 | 56 |
| 2 | 57 |
| 3 | 58 |
| 4 | 59 |
| 5 | 60 |
| 6 | 61 |
| 7 | 62 |
| 8 | 63 |
| 9 | 64 |
| 10 | 65 |
| 11 | 66 |
| 12 | 67 |
| 13 | 68 |
| 14 | 69 |
| 15 | 70 |
| 16 | 71 |
| 17 | 72 |
| 18 | 73 |
| 19 | 74 |
| 57-mer peptides of SEQ ID NO:2 | |
| 1 | 57 |
| 2 | 58 |
| 3 | 59 |
| 4 | 60 |
| 5 | 61 |
| 6 | 62 |
| 7 | 63 |
| 8 | 64 |
| 9 | 65 |
| 10 | 66 |
| 11 | 67 |
| 12 | 68 |
| 13 | 69 |
| 14 | 70 |
| 15 | 71 |
| 16 | 72 |
| 17 | 73 |
| 18 | 74 |
| 58-mer peptides of SEQ ID NO:2 | |
| 1 | 58 |
| 2 | 59 |
| 3 | 60 |
| 4 | 61 |
| 5 | 62 |
| 6 | 63 |
| 7 | 64 |
| 8 | 65 |
| 9 | 66 |
| 10 | 67 |
| 11 | 68 |
| 12 | 69 |
| 13 | 70 |
| 14 | 71 |
| 15 | 72 |
| 16 | 73 |
| 17 | 74 |
| 59-mer peptides of SEQ ID NO:2 | |
| 1 | 59 |
| 2 | 60 |
| 3 | 61 |
| 4 | 62 |
| 5 | 63 |
| 6 | 64 |
| 7 | 65 |
| 8 | 66 |
| 9 | 67 |
| 10 | 68 |
| 11 | 69 |
| 12 | 70 |
| 13 | 71 |
| 14 | 72 |
| 15 | 73 |
| 16 | 74 |
| 60-mer peptides of SEQ ID NO:2 | |
| 1 | 60 |
| 2 | 61 |
| 3 | 62 |
| 4 | 63 |
| 5 | 64 |
| 6 | 65 |
| 7 | 66 |
| 8 | 67 |
| 9 | 68 |
| 10 | 69 |
| 11 | 70 |
| 12 | 71 |
| 13 | 72 |
| 14 | 73 |
| 15 | 74 |
| 61-mer peptides of SEQ ID NO:2 | |
| 1 | 61 |
| 2 | 62 |
| 3 | 63 |
| 4 | 64 |
| 5 | 65 |
| 6 | 66 |
| 7 | 67 |
| 8 | 68 |
| 9 | 69 |
| 10 | 70 |

TABLE 1-continued

| N-terminal amino acid position | C-terminal amino acid position |
|---|---|
| 11 | 71 |
| 12 | 72 |
| 13 | 73 |
| 14 | 74 |
| 62-mer peptides of SEQ ID NO:2 | |
| 1 | 62 |
| 2 | 63 |
| 3 | 64 |
| 4 | 65 |
| 5 | 66 |
| 6 | 67 |
| 7 | 68 |
| 8 | 69 |
| 9 | 70 |
| 10 | 71 |
| 11 | 72 |
| 12 | 73 |
| 13 | 74 |
| 63-mer peptides of SEQ ID NO:2 | |
| 1 | 63 |
| 2 | 64 |
| 3 | 65 |
| 4 | 66 |
| 5 | 67 |
| 6 | 68 |
| 7 | 69 |
| 8 | 70 |
| 9 | 71 |
| 10 | 72 |
| 11 | 73 |
| 12 | 74 |
| 64-mer peptides of SEQ ID NO:2 | |
| 1 | 64 |
| 2 | 65 |
| 3 | 66 |
| 4 | 67 |
| 5 | 68 |
| 6 | 69 |
| 7 | 70 |
| 8 | 71 |
| 9 | 72 |
| 10 | 73 |
| 11 | 74 |
| 65-mer peptides of SEQ ID NO:2 | |
| 1 | 65 |
| 2 | 66 |
| 3 | 67 |
| 4 | 68 |
| 5 | 69 |
| 6 | 70 |
| 7 | 71 |
| 8 | 72 |
| 9 | 73 |
| 10 | 74 |
| 66-mer peptides of SEQ ID NO:2 | |
| 1 | 66 |
| 2 | 67 |
| 3 | 68 |
| 4 | 69 |
| 5 | 70 |
| 6 | 71 |
| 7 | 72 |
| 8 | 73 |
| 9 | 74 |
| 67-mer peptides of SEQ ID NO:2 | |
| 1 | 67 |
| 2 | 68 |
| 3 | 69 |
| 4 | 70 |
| 5 | 71 |
| 6 | 72 |
| 7 | 73 |
| 8 | 74 |
| 68-mer peptides of SEQ ID NO:2 | |
| 1 | 68 |
| 2 | 69 |
| 3 | 70 |
| 4 | 71 |
| 5 | 72 |
| 6 | 73 |
| 7 | 74 |
| 69-mer peptides of SEQ ID NO:2 | |
| 1 | 69 |
| 2 | 70 |
| 3 | 71 |
| 4 | 72 |
| 5 | 73 |
| 6 | 74 |
| 70-mer peptides of SEQ ID NO:2 | |
| 1 | 70 |
| 2 | 71 |
| 3 | 72 |
| 4 | 73 |
| 5 | 74 |
| 71-mer peptides of SEQ ID NO:2 | |
| 1 | 71 |
| 2 | 72 |
| 3 | 73 |
| 4 | 74 |
| 72-mer peptides of SEQ ID NO:2 | |
| 1 | 72 |
| 2 | 73 |
| 3 | 74 |
| 73-mer peptides of SEQ ID NO:2 | |
| 1 | 73 |
| 2 | 74 |

TABLE 2

| N-terminal amino acid position | C-terminal amino acid position |
|---|---|
| 5-mer peptides of SEQ ID NO:3 | |
| 1 | 5 |
| 2 | 6 |
| 3 | 7 |
| 4 | 8 |
| 5 | 9 |
| 6 | 10 |
| 7 | 11 |
| 8 | 12 |
| 9 | 13 |
| 10 | 14 |
| 11 | 15 |
| 12 | 16 |
| 13 | 17 |
| 14 | 18 |
| 15 | 19 |
| 16 | 20 |
| 17 | 21 |
| 18 | 22 |
| 19 | 23 |
| 20 | 24 |
| 21 | 25 |
| 22 | 26 |
| 23 | 27 |

TABLE 2-continued

| N-terminal amino acid position | C-terminal amino acid position |
|---|---|
| 24 | 28 |
| 25 | 29 |
| 26 | 30 |
| 27 | 31 |
| 28 | 32 |
| 29 | 33 |
| 30 | 34 |
| 31 | 35 |
| 32 | 36 |
| 33 | 37 |
| 34 | 38 |
| 35 | 39 |
| 36 | 40 |
| 37 | 41 |
| 38 | 42 |
| 39 | 43 |
| 40 | 44 |
| 41 | 45 |
| 42 | 46 |
| 43 | 47 |
| 44 | 48 |
| 45 | 49 |
| 46 | 50 |
| 47 | 51 |
| 48 | 52 |
| 49 | 53 |
| 50 | 54 |
| 51 | 55 |
| 52 | 56 |
| 53 | 57 |
| 54 | 58 |
| 55 | 59 |
| 56 | 60 |
| 57 | 61 |
| 58 | 62 |
| 59 | 63 |
| 60 | 64 |
| 61 | 65 |
| 62 | 66 |
| 63 | 67 |
| 64 | 68 |
| 65 | 69 |
| 66 | 70 |
| 67 | 71 |
| 68 | 72 |
| 69 | 73 |
| 70 | 74 |
| 71 | 75 |
| 72 | 76 |
| 73 | 77 |
| 74 | 78 |
| 75 | 79 |
| 76 | 80 |
| 77 | 81 |
| 78 | 82 |
| 79 | 83 |
| 80 | 84 |
| 81 | 85 |
| 82 | 86 |
| 83 | 87 |
| 84 | 88 |
| 85 | 89 |
| 6-mer peptides of SEQ ID NO:3 | |
| 1 | 6 |
| 2 | 7 |
| 3 | 8 |
| 4 | 9 |
| 5 | 10 |
| 6 | 11 |
| 7 | 12 |
| 8 | 13 |
| 9 | 14 |
| 10 | 15 |
| 11 | 16 |
| 12 | 17 |

TABLE 2-continued

| N-terminal amino acid position | C-terminal amino acid position |
|---|---|
| 13 | 18 |
| 14 | 19 |
| 15 | 20 |
| 16 | 21 |
| 17 | 22 |
| 18 | 23 |
| 19 | 24 |
| 20 | 25 |
| 21 | 26 |
| 22 | 27 |
| 23 | 28 |
| 24 | 29 |
| 25 | 30 |
| 26 | 31 |
| 27 | 32 |
| 28 | 33 |
| 29 | 34 |
| 30 | 35 |
| 31 | 36 |
| 32 | 37 |
| 33 | 38 |
| 34 | 39 |
| 35 | 40 |
| 36 | 41 |
| 37 | 42 |
| 38 | 43 |
| 39 | 44 |
| 40 | 45 |
| 41 | 46 |
| 42 | 47 |
| 43 | 48 |
| 44 | 49 |
| 45 | 50 |
| 46 | 51 |
| 47 | 52 |
| 48 | 53 |
| 49 | 54 |
| 50 | 55 |
| 51 | 56 |
| 52 | 57 |
| 53 | 58 |
| 54 | 59 |
| 55 | 60 |
| 56 | 61 |
| 57 | 62 |
| 58 | 63 |
| 59 | 64 |
| 60 | 65 |
| 61 | 66 |
| 62 | 67 |
| 63 | 68 |
| 64 | 69 |
| 65 | 70 |
| 66 | 71 |
| 67 | 72 |
| 68 | 73 |
| 69 | 74 |
| 70 | 75 |
| 71 | 76 |
| 72 | 77 |
| 73 | 78 |
| 74 | 79 |
| 75 | 80 |
| 76 | 81 |
| 77 | 82 |
| 78 | 83 |
| 79 | 84 |
| 80 | 85 |
| 81 | 86 |
| 82 | 87 |
| 83 | 88 |
| 84 | 89 |
| 7-mer peptides of SEQ ID NO:3 | |
| 1 | 7 |
| 2 | 8 |

TABLE 2-continued

| N-terminal amino acid position | C-terminal amino acid position |
|---|---|
| 3 | 9 |
| 4 | 10 |
| 5 | 11 |
| 6 | 12 |
| 7 | 13 |
| 8 | 14 |
| 9 | 15 |
| 10 | 16 |
| 11 | 17 |
| 12 | 18 |
| 13 | 19 |
| 14 | 20 |
| 15 | 21 |
| 16 | 22 |
| 17 | 23 |
| 18 | 24 |
| 19 | 25 |
| 20 | 26 |
| 21 | 27 |
| 22 | 28 |
| 23 | 29 |
| 24 | 30 |
| 25 | 31 |
| 26 | 32 |
| 27 | 33 |
| 28 | 34 |
| 29 | 35 |
| 30 | 36 |
| 31 | 37 |
| 32 | 38 |
| 33 | 39 |
| 34 | 40 |
| 35 | 41 |
| 36 | 42 |
| 37 | 43 |
| 38 | 44 |
| 39 | 45 |
| 40 | 46 |
| 41 | 47 |
| 42 | 48 |
| 43 | 49 |
| 44 | 50 |
| 45 | 51 |
| 46 | 52 |
| 47 | 53 |
| 48 | 54 |
| 49 | 55 |
| 50 | 56 |
| 51 | 57 |
| 52 | 58 |
| 53 | 59 |
| 54 | 60 |
| 55 | 61 |
| 56 | 62 |
| 57 | 63 |
| 58 | 64 |
| 59 | 65 |
| 60 | 66 |
| 61 | 67 |
| 62 | 68 |
| 63 | 69 |
| 64 | 70 |
| 65 | 71 |
| 66 | 72 |
| 67 | 73 |
| 68 | 74 |
| 69 | 75 |
| 70 | 76 |
| 71 | 77 |
| 72 | 78 |
| 73 | 79 |
| 74 | 80 |
| 75 | 81 |
| 76 | 82 |
| 77 | 83 |
| 78 | 84 |

TABLE 2-continued

| N-terminal amino acid position | C-terminal amino acid position |
|---|---|
| 79 | 85 |
| 80 | 86 |
| 81 | 87 |
| 82 | 88 |
| 83 | 89 |
| 8-mer peptides of SEQ ID NO:3 | |
| 1 | 8 |
| 2 | 9 |
| 3 | 10 |
| 4 | 11 |
| 5 | 12 |
| 6 | 13 |
| 7 | 14 |
| 8 | 15 |
| 9 | 16 |
| 10 | 17 |
| 11 | 18 |
| 12 | 19 |
| 13 | 20 |
| 14 | 21 |
| 15 | 22 |
| 16 | 23 |
| 17 | 24 |
| 18 | 25 |
| 19 | 26 |
| 20 | 27 |
| 21 | 28 |
| 22 | 29 |
| 23 | 30 |
| 24 | 31 |
| 25 | 32 |
| 26 | 33 |
| 27 | 34 |
| 28 | 35 |
| 29 | 36 |
| 30 | 37 |
| 31 | 38 |
| 32 | 39 |
| 33 | 40 |
| 34 | 41 |
| 35 | 42 |
| 36 | 43 |
| 37 | 44 |
| 38 | 45 |
| 39 | 46 |
| 40 | 47 |
| 41 | 48 |
| 42 | 49 |
| 43 | 50 |
| 44 | 51 |
| 45 | 52 |
| 46 | 53 |
| 47 | 54 |
| 48 | 55 |
| 49 | 56 |
| 50 | 57 |
| 51 | 58 |
| 52 | 59 |
| 53 | 60 |
| 54 | 61 |
| 55 | 62 |
| 56 | 63 |
| 57 | 64 |
| 58 | 65 |
| 59 | 66 |
| 60 | 67 |
| 61 | 68 |
| 62 | 69 |
| 63 | 70 |
| 64 | 71 |
| 65 | 72 |
| 66 | 73 |
| 67 | 74 |
| 68 | 75 |
| 69 | 76 |

TABLE 2-continued

| N-terminal amino acid position | C-terminal amino acid position |
|---|---|
| 70 | 77 |
| 71 | 78 |
| 72 | 79 |
| 73 | 80 |
| 74 | 81 |
| 75 | 82 |
| 76 | 83 |
| 77 | 84 |
| 78 | 85 |
| 79 | 86 |
| 80 | 87 |
| 81 | 88 |
| 82 | 89 |
| 9-mer peptides of SEQ ID NO:3 | |
| 1 | 9 |
| 2 | 10 |
| 3 | 11 |
| 4 | 12 |
| 5 | 13 |
| 6 | 14 |
| 7 | 15 |
| 8 | 16 |
| 9 | 17 |
| 10 | 18 |
| 11 | 19 |
| 12 | 20 |
| 13 | 21 |
| 14 | 22 |
| 15 | 23 |
| 16 | 24 |
| 17 | 25 |
| 18 | 26 |
| 19 | 27 |
| 20 | 28 |
| 21 | 29 |
| 22 | 30 |
| 23 | 31 |
| 24 | 32 |
| 25 | 33 |
| 26 | 34 |
| 27 | 35 |
| 28 | 36 |
| 29 | 37 |
| 30 | 38 |
| 31 | 39 |
| 32 | 40 |
| 33 | 41 |
| 34 | 42 |
| 35 | 43 |
| 36 | 44 |
| 37 | 45 |
| 38 | 46 |
| 39 | 47 |
| 40 | 48 |
| 41 | 49 |
| 42 | 50 |
| 43 | 51 |
| 44 | 52 |
| 45 | 53 |
| 46 | 54 |
| 47 | 55 |
| 48 | 56 |
| 49 | 57 |
| 50 | 58 |
| 51 | 59 |
| 52 | 60 |
| 53 | 61 |
| 54 | 62 |
| 55 | 63 |
| 56 | 64 |
| 57 | 65 |
| 58 | 66 |
| 59 | 67 |
| 60 | 68 |
| 61 | 69 |

TABLE 2-continued

| N-terminal amino acid position | C-terminal amino acid position |
|---|---|
| 62 | 70 |
| 63 | 71 |
| 64 | 72 |
| 65 | 73 |
| 66 | 74 |
| 67 | 75 |
| 68 | 76 |
| 69 | 77 |
| 70 | 78 |
| 71 | 79 |
| 72 | 80 |
| 73 | 81 |
| 74 | 82 |
| 75 | 83 |
| 76 | 84 |
| 77 | 85 |
| 78 | 86 |
| 79 | 87 |
| 80 | 88 |
| 81 | 89 |
| 10-mer peptides of SEQ ID NO:3 | |
| 1 | 10 |
| 2 | 11 |
| 3 | 12 |
| 4 | 13 |
| 5 | 14 |
| 6 | 15 |
| 7 | 16 |
| 8 | 17 |
| 9 | 18 |
| 10 | 19 |
| 11 | 20 |
| 12 | 21 |
| 13 | 22 |
| 14 | 23 |
| 15 | 24 |
| 16 | 25 |
| 17 | 26 |
| 18 | 27 |
| 19 | 28 |
| 20 | 29 |
| 21 | 30 |
| 22 | 31 |
| 23 | 32 |
| 24 | 33 |
| 25 | 34 |
| 26 | 35 |
| 27 | 36 |
| 28 | 37 |
| 29 | 38 |
| 30 | 39 |
| 31 | 40 |
| 32 | 41 |
| 33 | 42 |
| 34 | 43 |
| 35 | 44 |
| 36 | 45 |
| 37 | 46 |
| 38 | 47 |
| 39 | 48 |
| 40 | 49 |
| 41 | 50 |
| 42 | 51 |
| 43 | 52 |
| 44 | 53 |
| 45 | 54 |
| 46 | 55 |
| 47 | 56 |
| 48 | 57 |
| 49 | 58 |
| 50 | 59 |
| 51 | 60 |
| 52 | 61 |
| 53 | 62 |
| 54 | 63 |

TABLE 2-continued

| N-terminal amino acid position | C-terminal amino acid position |
|---|---|
| 55 | 64 |
| 56 | 65 |
| 57 | 66 |
| 58 | 67 |
| 59 | 68 |
| 60 | 69 |
| 61 | 70 |
| 62 | 71 |
| 63 | 72 |
| 64 | 73 |
| 65 | 74 |
| 66 | 75 |
| 67 | 76 |
| 68 | 77 |
| 69 | 78 |
| 70 | 79 |
| 71 | 80 |
| 72 | 81 |
| 73 | 82 |
| 74 | 83 |
| 75 | 84 |
| 76 | 85 |
| 77 | 86 |
| 78 | 87 |
| 79 | 88 |
| 80 | 89 |
| 11-mer peptides of SEQ ID NO:3 | |
| 1 | 11 |
| 2 | 12 |
| 3 | 13 |
| 4 | 14 |
| 5 | 15 |
| 6 | 16 |
| 7 | 17 |
| 8 | 18 |
| 9 | 19 |
| 10 | 20 |
| 11 | 21 |
| 12 | 22 |
| 13 | 23 |
| 14 | 24 |
| 15 | 25 |
| 16 | 26 |
| 17 | 27 |
| 18 | 28 |
| 19 | 29 |
| 20 | 30 |
| 21 | 31 |
| 22 | 32 |
| 23 | 33 |
| 24 | 34 |
| 25 | 35 |
| 26 | 36 |
| 27 | 37 |
| 28 | 38 |
| 29 | 39 |
| 30 | 40 |
| 31 | 41 |
| 32 | 42 |
| 33 | 43 |
| 34 | 44 |
| 35 | 45 |
| 36 | 46 |
| 37 | 47 |
| 38 | 48 |
| 39 | 49 |
| 40 | 50 |
| 41 | 51 |
| 42 | 52 |
| 43 | 53 |
| 44 | 54 |
| 45 | 55 |
| 46 | 56 |
| 47 | 57 |
| 48 | 58 |

TABLE 2-continued

| N-terminal amino acid position | C-terminal amino acid position |
|---|---|
| 49 | 59 |
| 50 | 60 |
| 51 | 61 |
| 52 | 62 |
| 53 | 63 |
| 54 | 64 |
| 55 | 65 |
| 56 | 66 |
| 57 | 67 |
| 58 | 68 |
| 59 | 69 |
| 60 | 70 |
| 61 | 71 |
| 62 | 72 |
| 63 | 73 |
| 64 | 74 |
| 65 | 75 |
| 66 | 76 |
| 67 | 77 |
| 68 | 78 |
| 69 | 79 |
| 70 | 80 |
| 71 | 81 |
| 72 | 82 |
| 73 | 83 |
| 74 | 84 |
| 75 | 85 |
| 76 | 86 |
| 77 | 87 |
| 78 | 88 |
| 79 | 89 |
| 12-mer peptides of SEQ ID NO:3 | |
| 1 | 12 |
| 2 | 13 |
| 3 | 14 |
| 4 | 15 |
| 5 | 16 |
| 6 | 17 |
| 7 | 18 |
| 8 | 19 |
| 9 | 20 |
| 10 | 21 |
| 11 | 22 |
| 12 | 23 |
| 13 | 24 |
| 14 | 25 |
| 15 | 26 |
| 16 | 27 |
| 17 | 28 |
| 18 | 29 |
| 19 | 30 |
| 20 | 31 |
| 21 | 32 |
| 22 | 33 |
| 23 | 34 |
| 24 | 35 |
| 25 | 36 |
| 26 | 37 |
| 27 | 38 |
| 28 | 39 |
| 29 | 40 |
| 30 | 41 |
| 31 | 42 |
| 32 | 43 |
| 33 | 44 |
| 34 | 45 |
| 35 | 46 |
| 36 | 47 |
| 37 | 48 |
| 38 | 49 |
| 39 | 50 |
| 40 | 51 |
| 41 | 52 |
| 42 | 53 |
| 43 | 54 |

TABLE 2-continued

| N-terminal amino acid position | C-terminal amino acid position |
|---|---|
| 44 | 55 |
| 45 | 56 |
| 46 | 57 |
| 47 | 58 |
| 48 | 59 |
| 49 | 60 |
| 50 | 61 |
| 51 | 62 |
| 52 | 63 |
| 53 | 64 |
| 54 | 65 |
| 55 | 66 |
| 56 | 67 |
| 57 | 68 |
| 58 | 69 |
| 59 | 70 |
| 60 | 71 |
| 61 | 72 |
| 62 | 73 |
| 63 | 74 |
| 64 | 75 |
| 65 | 76 |
| 66 | 77 |
| 67 | 78 |
| 68 | 79 |
| 69 | 80 |
| 70 | 81 |
| 71 | 82 |
| 72 | 83 |
| 73 | 84 |
| 74 | 85 |
| 75 | 86 |
| 76 | 87 |
| 77 | 88 |
| 78 | 89 |
| 13-mer peptides of SEQ ID NO:3 | |
| 1 | 13 |
| 2 | 14 |
| 3 | 15 |
| 4 | 16 |
| 5 | 17 |
| 6 | 18 |
| 7 | 19 |
| 8 | 20 |
| 9 | 21 |
| 10 | 22 |
| 11 | 23 |
| 12 | 24 |
| 13 | 25 |
| 14 | 26 |
| 15 | 27 |
| 16 | 28 |
| 17 | 29 |
| 18 | 30 |
| 19 | 31 |
| 20 | 32 |
| 21 | 33 |
| 22 | 34 |
| 23 | 35 |
| 24 | 36 |
| 25 | 37 |
| 26 | 38 |
| 27 | 39 |
| 28 | 40 |
| 29 | 41 |
| 30 | 42 |
| 31 | 43 |
| 32 | 44 |
| 33 | 45 |
| 34 | 46 |
| 35 | 47 |
| 36 | 48 |
| 37 | 49 |
| 38 | 50 |
| 39 | 51 |
| 40 | 52 |
| 41 | 53 |
| 42 | 54 |
| 43 | 55 |
| 44 | 56 |
| 45 | 57 |
| 46 | 58 |
| 47 | 59 |
| 48 | 60 |
| 49 | 61 |
| 50 | 62 |
| 51 | 63 |
| 52 | 64 |
| 53 | 65 |
| 54 | 66 |
| 55 | 67 |
| 56 | 68 |
| 57 | 69 |
| 58 | 70 |
| 59 | 71 |
| 60 | 72 |
| 61 | 73 |
| 62 | 74 |
| 63 | 75 |
| 64 | 76 |
| 65 | 77 |
| 66 | 78 |
| 67 | 79 |
| 68 | 80 |
| 69 | 81 |
| 70 | 82 |
| 71 | 83 |
| 72 | 84 |
| 73 | 85 |
| 74 | 86 |
| 75 | 87 |
| 76 | 88 |
| 77 | 89 |
| 14-mer peptides of SEQ ID NO:3 | |
| 1 | 14 |
| 2 | 15 |
| 3 | 16 |
| 4 | 17 |
| 5 | 18 |
| 6 | 19 |
| 7 | 20 |
| 8 | 21 |
| 9 | 22 |
| 10 | 23 |
| 11 | 24 |
| 12 | 25 |
| 13 | 26 |
| 14 | 27 |
| 15 | 28 |
| 16 | 29 |
| 17 | 30 |
| 18 | 31 |
| 19 | 32 |
| 20 | 33 |
| 21 | 34 |
| 22 | 35 |
| 23 | 36 |
| 24 | 37 |
| 25 | 38 |
| 26 | 39 |
| 27 | 40 |
| 28 | 41 |
| 29 | 42 |
| 30 | 43 |
| 31 | 44 |
| 32 | 45 |
| 33 | 46 |
| 34 | 47 |
| 35 | 48 |
| 36 | 49 |

TABLE 2-continued

| N-terminal amino acid position | C-terminal amino acid position |
|---|---|
| 37 | 50 |
| 38 | 51 |
| 39 | 52 |
| 40 | 53 |
| 41 | 54 |
| 42 | 55 |
| 43 | 56 |
| 44 | 57 |
| 45 | 58 |
| 46 | 59 |
| 47 | 60 |
| 48 | 61 |
| 49 | 62 |
| 50 | 63 |
| 51 | 64 |
| 52 | 65 |
| 53 | 66 |
| 54 | 67 |
| 55 | 68 |
| 56 | 69 |
| 57 | 70 |
| 58 | 71 |
| 59 | 72 |
| 60 | 73 |
| 61 | 74 |
| 62 | 75 |
| 63 | 76 |
| 64 | 77 |
| 65 | 78 |
| 66 | 79 |
| 67 | 80 |
| 68 | 81 |
| 69 | 82 |
| 70 | 83 |
| 71 | 84 |
| 72 | 85 |
| 73 | 86 |
| 74 | 87 |
| 75 | 88 |
| 76 | 89 |
| 15-mer peptides of SEQ ID NO:3 | |
| 1 | 15 |
| 2 | 16 |
| 3 | 17 |
| 4 | 18 |
| 5 | 19 |
| 6 | 20 |
| 7 | 21 |
| 8 | 22 |
| 9 | 23 |
| 10 | 24 |
| 11 | 25 |
| 12 | 26 |
| 13 | 27 |
| 14 | 28 |
| 15 | 29 |
| 16 | 30 |
| 17 | 31 |
| 18 | 32 |
| 19 | 33 |
| 20 | 34 |
| 21 | 35 |
| 22 | 36 |
| 23 | 37 |
| 24 | 38 |
| 25 | 39 |
| 26 | 40 |
| 27 | 41 |
| 28 | 42 |
| 29 | 43 |
| 30 | 44 |
| 31 | 45 |
| 32 | 46 |
| 33 | 47 |
| 34 | 48 |

TABLE 2-continued

| N-terminal amino acid position | C-terminal amino acid position |
|---|---|
| 35 | 49 |
| 36 | 50 |
| 37 | 51 |
| 38 | 52 |
| 39 | 53 |
| 40 | 54 |
| 41 | 55 |
| 42 | 56 |
| 43 | 57 |
| 44 | 58 |
| 45 | 59 |
| 46 | 60 |
| 47 | 61 |
| 48 | 62 |
| 49 | 63 |
| 50 | 64 |
| 51 | 65 |
| 52 | 66 |
| 53 | 67 |
| 54 | 68 |
| 55 | 69 |
| 56 | 70 |
| 57 | 71 |
| 58 | 72 |
| 59 | 73 |
| 60 | 74 |
| 61 | 75 |
| 62 | 76 |
| 63 | 77 |
| 64 | 78 |
| 65 | 79 |
| 66 | 80 |
| 67 | 81 |
| 68 | 82 |
| 69 | 83 |
| 70 | 84 |
| 71 | 85 |
| 72 | 86 |
| 73 | 87 |
| 74 | 88 |
| 75 | 89 |
| 16-mer peptides of SEQ ID NO:3 | |
| 1 | 16 |
| 2 | 17 |
| 3 | 18 |
| 4 | 19 |
| 5 | 20 |
| 6 | 21 |
| 7 | 22 |
| 8 | 23 |
| 9 | 24 |
| 10 | 25 |
| 11 | 26 |
| 12 | 27 |
| 13 | 28 |
| 14 | 29 |
| 15 | 30 |
| 16 | 31 |
| 17 | 32 |
| 18 | 33 |
| 19 | 34 |
| 20 | 35 |
| 21 | 36 |
| 22 | 37 |
| 23 | 38 |
| 24 | 39 |
| 25 | 40 |
| 26 | 41 |
| 27 | 42 |
| 28 | 43 |
| 29 | 44 |
| 30 | 45 |
| 31 | 46 |
| 32 | 47 |
| 33 | 48 |

TABLE 2-continued

| N-terminal amino acid position | C-terminal amino acid position |
|---|---|
| 34 | 49 |
| 35 | 50 |
| 36 | 51 |
| 37 | 52 |
| 38 | 53 |
| 39 | 54 |
| 40 | 55 |
| 41 | 56 |
| 42 | 57 |
| 43 | 58 |
| 44 | 59 |
| 45 | 60 |
| 46 | 61 |
| 47 | 62 |
| 48 | 63 |
| 49 | 64 |
| 50 | 65 |
| 51 | 66 |
| 52 | 67 |
| 53 | 68 |
| 54 | 69 |
| 55 | 70 |
| 56 | 71 |
| 57 | 72 |
| 58 | 73 |
| 59 | 74 |
| 60 | 75 |
| 61 | 76 |
| 62 | 77 |
| 63 | 78 |
| 64 | 79 |
| 65 | 80 |
| 66 | 81 |
| 67 | 82 |
| 68 | 83 |
| 69 | 84 |
| 70 | 85 |
| 71 | 86 |
| 72 | 87 |
| 73 | 88 |
| 74 | 89 |
| 17-mer peptides of SEQ ID NO:3 | |
| 1 | 17 |
| 2 | 18 |
| 3 | 19 |
| 4 | 20 |
| 5 | 21 |
| 6 | 22 |
| 7 | 23 |
| 8 | 24 |
| 9 | 25 |
| 10 | 26 |
| 11 | 27 |
| 12 | 28 |
| 13 | 29 |
| 14 | 30 |
| 15 | 31 |
| 16 | 32 |
| 17 | 33 |
| 18 | 34 |
| 19 | 35 |
| 20 | 36 |
| 21 | 37 |
| 22 | 38 |
| 23 | 39 |
| 24 | 40 |
| 25 | 41 |
| 26 | 42 |
| 27 | 43 |
| 28 | 44 |
| 29 | 45 |
| 30 | 46 |
| 31 | 47 |
| 32 | 48 |
| 33 | 49 |

TABLE 2-continued

| N-terminal amino acid position | C-terminal amino acid position |
|---|---|
| 34 | 50 |
| 35 | 51 |
| 36 | 52 |
| 37 | 53 |
| 38 | 54 |
| 39 | 55 |
| 40 | 56 |
| 41 | 57 |
| 42 | 58 |
| 43 | 59 |
| 44 | 60 |
| 45 | 61 |
| 46 | 62 |
| 47 | 63 |
| 48 | 64 |
| 49 | 65 |
| 50 | 66 |
| 51 | 67 |
| 52 | 68 |
| 53 | 69 |
| 54 | 70 |
| 55 | 71 |
| 56 | 72 |
| 57 | 73 |
| 58 | 74 |
| 59 | 75 |
| 60 | 76 |
| 61 | 77 |
| 62 | 78 |
| 63 | 79 |
| 64 | 80 |
| 65 | 81 |
| 66 | 82 |
| 67 | 83 |
| 68 | 84 |
| 69 | 85 |
| 70 | 86 |
| 71 | 87 |
| 72 | 88 |
| 73 | 89 |
| 18-mer peptides of SEQ ID NO:3 | |
| 1 | 18 |
| 2 | 19 |
| 3 | 20 |
| 4 | 21 |
| 5 | 22 |
| 6 | 23 |
| 7 | 24 |
| 8 | 25 |
| 9 | 26 |
| 10 | 27 |
| 11 | 28 |
| 12 | 29 |
| 13 | 30 |
| 14 | 31 |
| 15 | 32 |
| 16 | 33 |
| 17 | 34 |
| 18 | 35 |
| 19 | 36 |
| 20 | 37 |
| 21 | 38 |
| 22 | 39 |
| 23 | 40 |
| 24 | 41 |
| 25 | 42 |
| 26 | 43 |
| 27 | 44 |
| 28 | 45 |
| 29 | 46 |
| 30 | 47 |
| 31 | 48 |
| 32 | 49 |
| 33 | 50 |
| 34 | 51 |

TABLE 2-continued

| N-terminal amino acid position | C-terminal amino acid position |
|---|---|
| 35 | 52 |
| 36 | 53 |
| 37 | 54 |
| 38 | 55 |
| 39 | 56 |
| 40 | 57 |
| 41 | 58 |
| 42 | 59 |
| 43 | 60 |
| 44 | 61 |
| 45 | 62 |
| 46 | 63 |
| 47 | 64 |
| 48 | 65 |
| 49 | 66 |
| 50 | 67 |
| 51 | 68 |
| 52 | 69 |
| 53 | 70 |
| 54 | 71 |
| 55 | 72 |
| 56 | 73 |
| 57 | 74 |
| 58 | 75 |
| 59 | 76 |
| 60 | 77 |
| 61 | 78 |
| 62 | 79 |
| 63 | 80 |
| 64 | 81 |
| 65 | 82 |
| 66 | 83 |
| 67 | 84 |
| 68 | 85 |
| 69 | 86 |
| 70 | 87 |
| 71 | 88 |
| 72 | 89 |
| 19-mer peptides of SEQ ID NO:3 | |
| 1 | 19 |
| 2 | 20 |
| 3 | 21 |
| 4 | 22 |
| 5 | 23 |
| 6 | 24 |
| 7 | 25 |
| 8 | 26 |
| 9 | 27 |
| 10 | 28 |
| 11 | 29 |
| 12 | 30 |
| 13 | 31 |
| 14 | 32 |
| 15 | 33 |
| 16 | 34 |
| 17 | 35 |
| 18 | 36 |
| 19 | 37 |
| 20 | 38 |
| 21 | 39 |
| 22 | 40 |
| 23 | 41 |
| 24 | 42 |
| 25 | 43 |
| 26 | 44 |
| 27 | 45 |
| 28 | 46 |
| 29 | 47 |
| 30 | 48 |
| 31 | 49 |
| 32 | 50 |
| 33 | 51 |
| 34 | 52 |
| 35 | 53 |
| 36 | 54 |
| 37 | 55 |
| 38 | 56 |
| 39 | 57 |
| 40 | 58 |
| 41 | 59 |
| 42 | 60 |
| 43 | 61 |
| 44 | 62 |
| 45 | 63 |
| 46 | 64 |
| 47 | 65 |
| 48 | 66 |
| 49 | 67 |
| 50 | 68 |
| 51 | 69 |
| 52 | 70 |
| 53 | 71 |
| 54 | 72 |
| 55 | 73 |
| 56 | 74 |
| 57 | 75 |
| 58 | 76 |
| 59 | 77 |
| 60 | 78 |
| 61 | 79 |
| 62 | 80 |
| 63 | 81 |
| 64 | 82 |
| 65 | 83 |
| 66 | 84 |
| 67 | 85 |
| 68 | 86 |
| 69 | 87 |
| 70 | 88 |
| 71 | 89 |
| 20-mer peptides of SEQ ID NO:3 | |
| 1 | 20 |
| 2 | 21 |
| 3 | 22 |
| 4 | 23 |
| 5 | 24 |
| 6 | 25 |
| 7 | 26 |
| 8 | 27 |
| 9 | 28 |
| 10 | 29 |
| 11 | 30 |
| 12 | 31 |
| 13 | 32 |
| 14 | 33 |
| 15 | 34 |
| 16 | 35 |
| 17 | 36 |
| 18 | 37 |
| 19 | 38 |
| 20 | 39 |
| 21 | 40 |
| 22 | 41 |
| 23 | 42 |
| 24 | 43 |
| 25 | 44 |
| 26 | 45 |
| 27 | 46 |
| 28 | 47 |
| 29 | 48 |
| 30 | 49 |
| 31 | 50 |
| 32 | 51 |
| 33 | 52 |
| 34 | 53 |
| 35 | 54 |
| 36 | 55 |
| 37 | 56 |
| 38 | 57 |
| 39 | 58 |

TABLE 2-continued

| N-terminal amino acid position | C-terminal amino acid position |
|---|---|
| 40 | 59 |
| 41 | 60 |
| 42 | 61 |
| 43 | 62 |
| 44 | 63 |
| 45 | 64 |
| 46 | 65 |
| 47 | 66 |
| 48 | 67 |
| 49 | 68 |
| 50 | 69 |
| 51 | 70 |
| 52 | 71 |
| 53 | 72 |
| 54 | 73 |
| 55 | 74 |
| 56 | 75 |
| 57 | 76 |
| 58 | 77 |
| 59 | 78 |
| 60 | 79 |
| 61 | 80 |
| 62 | 81 |
| 63 | 82 |
| 64 | 83 |
| 65 | 84 |
| 66 | 85 |
| 67 | 86 |
| 68 | 87 |
| 69 | 88 |
| 70 | 89 |
| 21-mer peptides of SEQ ID NO:3 | |
| 1 | 21 |
| 2 | 22 |
| 3 | 23 |
| 4 | 24 |
| 5 | 25 |
| 6 | 26 |
| 7 | 27 |
| 8 | 28 |
| 9 | 29 |
| 10 | 30 |
| 11 | 31 |
| 12 | 32 |
| 13 | 33 |
| 14 | 34 |
| 15 | 35 |
| 16 | 36 |
| 17 | 37 |
| 18 | 38 |
| 19 | 39 |
| 20 | 40 |
| 21 | 41 |
| 22 | 42 |
| 23 | 43 |
| 24 | 44 |
| 25 | 45 |
| 26 | 46 |
| 27 | 47 |
| 28 | 48 |
| 29 | 49 |
| 30 | 50 |
| 31 | 51 |
| 32 | 52 |
| 33 | 53 |
| 34 | 54 |
| 35 | 55 |
| 36 | 56 |
| 37 | 57 |
| 38 | 58 |
| 39 | 59 |
| 40 | 60 |
| 41 | 61 |
| 42 | 62 |
| 43 | 63 |
| 44 | 64 |
| 45 | 65 |
| 46 | 66 |
| 47 | 67 |
| 48 | 68 |
| 49 | 69 |
| 50 | 70 |
| 51 | 71 |
| 52 | 72 |
| 53 | 73 |
| 54 | 74 |
| 55 | 75 |
| 56 | 76 |
| 57 | 77 |
| 58 | 78 |
| 59 | 79 |
| 60 | 80 |
| 61 | 81 |
| 62 | 82 |
| 63 | 83 |
| 64 | 84 |
| 65 | 85 |
| 66 | 86 |
| 67 | 87 |
| 68 | 88 |
| 69 | 89 |
| 22-mer peptides of SEQ ID NO:3 | |
| 1 | 22 |
| 2 | 23 |
| 3 | 24 |
| 4 | 25 |
| 5 | 26 |
| 6 | 27 |
| 7 | 28 |
| 8 | 29 |
| 9 | 30 |
| 10 | 31 |
| 11 | 32 |
| 12 | 33 |
| 13 | 34 |
| 14 | 35 |
| 15 | 36 |
| 16 | 37 |
| 17 | 38 |
| 18 | 39 |
| 19 | 40 |
| 20 | 41 |
| 21 | 42 |
| 22 | 43 |
| 23 | 44 |
| 24 | 45 |
| 25 | 46 |
| 26 | 47 |
| 27 | 48 |
| 28 | 49 |
| 29 | 50 |
| 30 | 51 |
| 31 | 52 |
| 32 | 53 |
| 33 | 54 |
| 34 | 55 |
| 35 | 56 |
| 36 | 57 |
| 37 | 58 |
| 38 | 59 |
| 39 | 60 |
| 40 | 61 |
| 41 | 62 |
| 42 | 63 |
| 43 | 64 |
| 44 | 65 |
| 45 | 66 |
| 46 | 67 |
| 47 | 68 |
| 48 | 69 |

TABLE 2-continued

| N-terminal amino acid position | C-terminal amino acid position |
|---|---|
| 49 | 70 |
| 50 | 71 |
| 51 | 72 |
| 52 | 73 |
| 53 | 74 |
| 54 | 75 |
| 55 | 76 |
| 56 | 77 |
| 57 | 78 |
| 58 | 79 |
| 59 | 80 |
| 60 | 81 |
| 61 | 82 |
| 62 | 83 |
| 63 | 84 |
| 64 | 85 |
| 65 | 86 |
| 66 | 87 |
| 67 | 88 |
| 68 | 89 |
| 23-mer peptides of SEQ ID NO:3 | |
| 1 | 23 |
| 2 | 24 |
| 3 | 25 |
| 4 | 26 |
| 5 | 27 |
| 6 | 28 |
| 7 | 29 |
| 8 | 30 |
| 9 | 31 |
| 10 | 32 |
| 11 | 33 |
| 12 | 34 |
| 13 | 35 |
| 14 | 36 |
| 15 | 37 |
| 16 | 38 |
| 17 | 39 |
| 18 | 40 |
| 19 | 41 |
| 20 | 42 |
| 21 | 43 |
| 22 | 44 |
| 23 | 45 |
| 24 | 46 |
| 25 | 47 |
| 26 | 48 |
| 27 | 49 |
| 28 | 50 |
| 29 | 51 |
| 30 | 52 |
| 31 | 53 |
| 32 | 54 |
| 33 | 55 |
| 34 | 56 |
| 35 | 57 |
| 36 | 58 |
| 37 | 59 |
| 38 | 60 |
| 39 | 61 |
| 40 | 62 |
| 41 | 63 |
| 42 | 64 |
| 43 | 65 |
| 44 | 66 |
| 45 | 67 |
| 46 | 68 |
| 47 | 69 |
| 48 | 70 |
| 49 | 71 |
| 50 | 72 |
| 51 | 73 |
| 52 | 74 |
| 53 | 75 |
| 54 | 76 |

TABLE 2-continued

| N-terminal amino acid position | C-terminal amino acid position |
|---|---|
| 55 | 77 |
| 56 | 78 |
| 57 | 79 |
| 58 | 80 |
| 59 | 81 |
| 60 | 82 |
| 61 | 83 |
| 62 | 84 |
| 63 | 85 |
| 64 | 86 |
| 65 | 87 |
| 66 | 88 |
| 67 | 89 |
| 24-mer peptides of SEQ ID NO:3 | |
| 1 | 24 |
| 2 | 25 |
| 3 | 26 |
| 4 | 27 |
| 5 | 28 |
| 6 | 29 |
| 7 | 30 |
| 8 | 31 |
| 9 | 32 |
| 10 | 33 |
| 11 | 34 |
| 12 | 35 |
| 13 | 36 |
| 14 | 37 |
| 15 | 38 |
| 16 | 39 |
| 17 | 40 |
| 18 | 41 |
| 19 | 42 |
| 20 | 43 |
| 21 | 44 |
| 22 | 45 |
| 23 | 46 |
| 24 | 47 |
| 25 | 48 |
| 26 | 49 |
| 27 | 50 |
| 28 | 51 |
| 29 | 52 |
| 30 | 53 |
| 31 | 54 |
| 32 | 55 |
| 33 | 56 |
| 34 | 57 |
| 35 | 58 |
| 36 | 59 |
| 37 | 60 |
| 38 | 61 |
| 39 | 62 |
| 40 | 63 |
| 41 | 64 |
| 42 | 65 |
| 43 | 66 |
| 44 | 67 |
| 45 | 68 |
| 46 | 69 |
| 47 | 70 |
| 48 | 71 |
| 49 | 72 |
| 50 | 73 |
| 51 | 74 |
| 52 | 75 |
| 53 | 76 |
| 54 | 77 |
| 55 | 78 |
| 56 | 79 |
| 57 | 80 |
| 58 | 81 |
| 59 | 82 |
| 60 | 83 |
| 61 | 84 |

TABLE 2-continued

| N-terminal amino acid position | C-terminal amino acid position |
|---|---|
| 62 | 85 |
| 63 | 86 |
| 64 | 87 |
| 65 | 88 |
| 66 | 89 |
| 25-mer peptides of SEQ ID NO:3 | |
| 1 | 25 |
| 2 | 26 |
| 3 | 27 |
| 4 | 28 |
| 5 | 29 |
| 6 | 30 |
| 7 | 31 |
| 8 | 32 |
| 9 | 33 |
| 10 | 34 |
| 11 | 35 |
| 12 | 36 |
| 13 | 37 |
| 14 | 38 |
| 15 | 39 |
| 16 | 40 |
| 17 | 41 |
| 18 | 42 |
| 19 | 43 |
| 20 | 44 |
| 21 | 45 |
| 22 | 46 |
| 23 | 47 |
| 24 | 48 |
| 25 | 49 |
| 26 | 50 |
| 27 | 51 |
| 28 | 52 |
| 29 | 53 |
| 30 | 54 |
| 31 | 55 |
| 32 | 56 |
| 33 | 57 |
| 34 | 58 |
| 35 | 59 |
| 36 | 60 |
| 37 | 61 |
| 38 | 62 |
| 39 | 63 |
| 40 | 64 |
| 41 | 65 |
| 42 | 66 |
| 43 | 67 |
| 44 | 68 |
| 45 | 69 |
| 46 | 70 |
| 47 | 71 |
| 48 | 72 |
| 49 | 73 |
| 50 | 74 |
| 51 | 75 |
| 52 | 76 |
| 53 | 77 |
| 54 | 78 |
| 55 | 79 |
| 56 | 80 |
| 57 | 81 |
| 58 | 82 |
| 59 | 83 |
| 60 | 84 |
| 61 | 85 |
| 62 | 86 |
| 63 | 87 |
| 64 | 88 |
| 65 | 89 |
| 26-mer peptides of SEQ ID NO:3 | |
| 1 | 26 |
| 2 | 27 |

TABLE 2-continued

| N-terminal amino acid position | C-terminal amino acid position |
|---|---|
| 3 | 28 |
| 4 | 29 |
| 5 | 30 |
| 6 | 31 |
| 7 | 32 |
| 8 | 33 |
| 9 | 34 |
| 10 | 35 |
| 11 | 36 |
| 12 | 37 |
| 13 | 38 |
| 14 | 39 |
| 15 | 40 |
| 16 | 41 |
| 17 | 42 |
| 18 | 43 |
| 19 | 44 |
| 20 | 45 |
| 21 | 46 |
| 22 | 47 |
| 23 | 48 |
| 24 | 49 |
| 25 | 50 |
| 26 | 51 |
| 27 | 52 |
| 28 | 53 |
| 29 | 54 |
| 30 | 55 |
| 31 | 56 |
| 32 | 57 |
| 33 | 58 |
| 34 | 59 |
| 35 | 60 |
| 36 | 61 |
| 37 | 62 |
| 38 | 63 |
| 39 | 64 |
| 40 | 65 |
| 41 | 66 |
| 42 | 67 |
| 43 | 68 |
| 44 | 69 |
| 45 | 70 |
| 46 | 71 |
| 47 | 72 |
| 48 | 73 |
| 49 | 74 |
| 50 | 75 |
| 51 | 76 |
| 52 | 77 |
| 53 | 78 |
| 54 | 79 |
| 55 | 80 |
| 56 | 81 |
| 57 | 82 |
| 58 | 83 |
| 59 | 84 |
| 60 | 85 |
| 61 | 86 |
| 62 | 87 |
| 63 | 88 |
| 64 | 89 |
| 27-mer peptides of SEQ ID NO:3 | |
| 1 | 27 |
| 2 | 28 |
| 3 | 29 |
| 4 | 30 |
| 5 | 31 |
| 6 | 32 |
| 7 | 33 |
| 8 | 34 |
| 9 | 35 |
| 10 | 36 |
| 11 | 37 |
| 12 | 38 |

TABLE 2-continued

| N-terminal amino acid position | C-terminal amino acid position |
|---|---|
| 13 | 39 |
| 14 | 40 |
| 15 | 41 |
| 16 | 42 |
| 17 | 43 |
| 18 | 44 |
| 19 | 45 |
| 20 | 46 |
| 21 | 47 |
| 22 | 48 |
| 23 | 49 |
| 24 | 50 |
| 25 | 51 |
| 26 | 52 |
| 27 | 53 |
| 28 | 54 |
| 29 | 55 |
| 30 | 56 |
| 31 | 57 |
| 32 | 58 |
| 33 | 59 |
| 34 | 60 |
| 35 | 61 |
| 36 | 62 |
| 37 | 63 |
| 38 | 64 |
| 39 | 65 |
| 40 | 66 |
| 41 | 67 |
| 42 | 68 |
| 43 | 69 |
| 44 | 70 |
| 45 | 71 |
| 46 | 72 |
| 47 | 73 |
| 48 | 74 |
| 49 | 75 |
| 50 | 76 |
| 51 | 77 |
| 52 | 78 |
| 53 | 79 |
| 54 | 80 |
| 55 | 81 |
| 56 | 82 |
| 57 | 83 |
| 58 | 84 |
| 59 | 85 |
| 60 | 86 |
| 61 | 87 |
| 62 | 88 |
| 63 | 89 |
| 28-mer peptides of SEQ ID NO:3 | |
| 1 | 28 |
| 2 | 29 |
| 3 | 30 |
| 4 | 31 |
| 5 | 32 |
| 6 | 33 |
| 7 | 34 |
| 8 | 35 |
| 9 | 36 |
| 10 | 37 |
| 11 | 38 |
| 12 | 39 |
| 13 | 40 |
| 14 | 41 |
| 15 | 42 |
| 16 | 43 |
| 17 | 44 |
| 18 | 45 |
| 19 | 46 |
| 20 | 47 |
| 21 | 48 |
| 22 | 49 |
| 23 | 50 |

TABLE 2-continued

| N-terminal amino acid position | C-terminal amino acid position |
|---|---|
| 24 | 51 |
| 25 | 52 |
| 26 | 53 |
| 27 | 54 |
| 28 | 55 |
| 29 | 56 |
| 30 | 57 |
| 31 | 58 |
| 32 | 59 |
| 33 | 60 |
| 34 | 61 |
| 35 | 62 |
| 36 | 63 |
| 37 | 64 |
| 38 | 65 |
| 39 | 66 |
| 40 | 67 |
| 41 | 68 |
| 42 | 69 |
| 43 | 70 |
| 44 | 71 |
| 45 | 72 |
| 46 | 73 |
| 47 | 74 |
| 48 | 75 |
| 49 | 76 |
| 50 | 77 |
| 51 | 78 |
| 52 | 79 |
| 53 | 80 |
| 54 | 81 |
| 55 | 82 |
| 56 | 83 |
| 57 | 84 |
| 58 | 85 |
| 59 | 86 |
| 60 | 87 |
| 61 | 88 |
| 62 | 89 |
| 29-mer peptides of SEQ ID NO:3 | |
| 1 | 29 |
| 2 | 30 |
| 3 | 31 |
| 4 | 32 |
| 5 | 33 |
| 6 | 34 |
| 7 | 35 |
| 8 | 36 |
| 9 | 37 |
| 10 | 38 |
| 11 | 39 |
| 12 | 40 |
| 13 | 41 |
| 14 | 42 |
| 15 | 43 |
| 16 | 44 |
| 17 | 45 |
| 18 | 46 |
| 19 | 47 |
| 20 | 48 |
| 21 | 49 |
| 22 | 50 |
| 23 | 51 |
| 24 | 52 |
| 25 | 53 |
| 26 | 54 |
| 27 | 55 |
| 28 | 56 |
| 29 | 57 |
| 30 | 58 |
| 31 | 59 |
| 32 | 60 |
| 33 | 61 |
| 34 | 62 |
| 35 | 63 |

TABLE 2-continued

| N-terminal amino acid position | C-terminal amino acid position |
|---|---|
| 36 | 64 |
| 37 | 65 |
| 38 | 66 |
| 39 | 67 |
| 40 | 68 |
| 41 | 69 |
| 42 | 70 |
| 43 | 71 |
| 44 | 72 |
| 45 | 73 |
| 46 | 74 |
| 47 | 75 |
| 48 | 76 |
| 49 | 77 |
| 50 | 78 |
| 51 | 79 |
| 52 | 80 |
| 53 | 81 |
| 54 | 82 |
| 55 | 83 |
| 56 | 84 |
| 57 | 85 |
| 58 | 86 |
| 59 | 87 |
| 60 | 88 |
| 61 | 89 |
| 30-mer peptides of SEQ ID NO:3 | |
| 1 | 30 |
| 2 | 31 |
| 3 | 32 |
| 4 | 33 |
| 5 | 34 |
| 6 | 35 |
| 7 | 36 |
| 8 | 37 |
| 9 | 38 |
| 10 | 39 |
| 11 | 40 |
| 12 | 41 |
| 13 | 42 |
| 14 | 43 |
| 15 | 44 |
| 16 | 45 |
| 17 | 46 |
| 18 | 47 |
| 19 | 48 |
| 20 | 49 |
| 21 | 50 |
| 22 | 51 |
| 23 | 52 |
| 24 | 53 |
| 25 | 54 |
| 26 | 55 |
| 27 | 56 |
| 28 | 57 |
| 29 | 58 |
| 30 | 59 |
| 31 | 60 |
| 32 | 61 |
| 33 | 62 |
| 34 | 63 |
| 35 | 64 |
| 36 | 65 |
| 37 | 66 |
| 38 | 67 |
| 39 | 68 |
| 40 | 69 |
| 41 | 70 |
| 42 | 71 |
| 43 | 72 |
| 44 | 73 |
| 45 | 74 |
| 46 | 75 |
| 47 | 76 |
| 48 | 77 |
| 49 | 78 |
| 50 | 79 |
| 51 | 80 |
| 52 | 81 |
| 53 | 82 |
| 54 | 83 |
| 55 | 84 |
| 56 | 85 |
| 57 | 86 |
| 58 | 87 |
| 59 | 88 |
| 60 | 89 |
| 31-mer peptides of SEQ ID NO:3 | |
| 1 | 31 |
| 2 | 32 |
| 3 | 33 |
| 4 | 34 |
| 5 | 35 |
| 6 | 36 |
| 7 | 37 |
| 8 | 38 |
| 9 | 39 |
| 10 | 40 |
| 11 | 41 |
| 12 | 42 |
| 13 | 43 |
| 14 | 44 |
| 15 | 45 |
| 16 | 46 |
| 17 | 47 |
| 18 | 48 |
| 19 | 49 |
| 20 | 50 |
| 21 | 51 |
| 22 | 52 |
| 23 | 53 |
| 24 | 54 |
| 25 | 55 |
| 26 | 56 |
| 27 | 57 |
| 28 | 58 |
| 29 | 59 |
| 30 | 60 |
| 31 | 61 |
| 32 | 62 |
| 33 | 63 |
| 34 | 64 |
| 35 | 65 |
| 36 | 66 |
| 37 | 67 |
| 38 | 68 |
| 39 | 69 |
| 40 | 70 |
| 41 | 71 |
| 42 | 72 |
| 43 | 73 |
| 44 | 74 |
| 45 | 75 |
| 46 | 76 |
| 47 | 77 |
| 48 | 78 |
| 49 | 79 |
| 50 | 80 |
| 51 | 81 |
| 52 | 82 |
| 53 | 83 |
| 54 | 84 |
| 55 | 85 |
| 56 | 86 |
| 57 | 87 |
| 58 | 88 |
| 59 | 89 |

TABLE 2-continued

| N-terminal amino acid position | C-terminal amino acid position |
|---|---|
| 32-mer peptides of SEQ ID NO:3 | |
| 1 | 32 |
| 2 | 33 |
| 3 | 34 |
| 4 | 35 |
| 5 | 36 |
| 6 | 37 |
| 7 | 38 |
| 8 | 39 |
| 9 | 40 |
| 10 | 41 |
| 11 | 42 |
| 12 | 43 |
| 13 | 44 |
| 14 | 45 |
| 15 | 46 |
| 16 | 47 |
| 17 | 48 |
| 18 | 49 |
| 19 | 50 |
| 20 | 51 |
| 21 | 52 |
| 22 | 53 |
| 23 | 54 |
| 24 | 55 |
| 25 | 56 |
| 26 | 57 |
| 27 | 58 |
| 28 | 59 |
| 29 | 60 |
| 30 | 61 |
| 31 | 62 |
| 32 | 63 |
| 33 | 64 |
| 34 | 65 |
| 35 | 66 |
| 36 | 67 |
| 37 | 68 |
| 38 | 69 |
| 39 | 70 |
| 40 | 71 |
| 41 | 72 |
| 42 | 73 |
| 43 | 74 |
| 44 | 75 |
| 45 | 76 |
| 46 | 77 |
| 47 | 78 |
| 48 | 79 |
| 49 | 80 |
| 50 | 81 |
| 51 | 82 |
| 52 | 83 |
| 53 | 84 |
| 54 | 85 |
| 55 | 86 |
| 56 | 87 |
| 57 | 88 |
| 58 | 89 |
| 33-mer peptides of SEQ ID NO:3 | |
| 1 | 33 |
| 2 | 34 |
| 3 | 35 |
| 4 | 36 |
| 5 | 37 |
| 6 | 38 |
| 7 | 39 |
| 8 | 40 |
| 9 | 41 |
| 10 | 42 |
| 11 | 43 |
| 12 | 44 |
| 13 | 45 |
| 14 | 46 |
| 15 | 47 |
| 16 | 48 |
| 17 | 49 |
| 18 | 50 |
| 19 | 51 |
| 20 | 52 |
| 21 | 53 |
| 22 | 54 |
| 23 | 55 |
| 24 | 56 |
| 25 | 57 |
| 26 | 58 |
| 27 | 59 |
| 28 | 60 |
| 29 | 61 |
| 30 | 62 |
| 31 | 63 |
| 32 | 64 |
| 33 | 65 |
| 34 | 66 |
| 35 | 67 |
| 36 | 68 |
| 37 | 69 |
| 38 | 70 |
| 39 | 71 |
| 40 | 72 |
| 41 | 73 |
| 42 | 74 |
| 43 | 75 |
| 44 | 76 |
| 45 | 77 |
| 46 | 78 |
| 47 | 79 |
| 48 | 80 |
| 49 | 81 |
| 50 | 82 |
| 51 | 83 |
| 52 | 84 |
| 53 | 85 |
| 54 | 86 |
| 55 | 87 |
| 56 | 88 |
| 57 | 89 |
| 34-mer peptides of SEQ ID NO:3 | |
| 1 | 34 |
| 2 | 35 |
| 3 | 36 |
| 4 | 37 |
| 5 | 38 |
| 6 | 39 |
| 7 | 40 |
| 8 | 41 |
| 9 | 42 |
| 10 | 43 |
| 11 | 44 |
| 12 | 45 |
| 13 | 46 |
| 14 | 47 |
| 15 | 48 |
| 16 | 49 |
| 17 | 50 |
| 18 | 51 |
| 19 | 52 |
| 20 | 53 |
| 21 | 54 |
| 22 | 55 |
| 23 | 56 |
| 24 | 57 |
| 25 | 58 |
| 26 | 59 |
| 27 | 60 |
| 28 | 61 |
| 29 | 62 |
| 30 | 63 |
| 31 | 64 |

TABLE 2-continued

| N-terminal amino acid position | C-terminal amino acid position |
|---|---|
| 32 | 65 |
| 33 | 66 |
| 34 | 67 |
| 35 | 68 |
| 36 | 69 |
| 37 | 70 |
| 38 | 71 |
| 39 | 72 |
| 40 | 73 |
| 41 | 74 |
| 42 | 75 |
| 43 | 76 |
| 44 | 77 |
| 45 | 78 |
| 46 | 79 |
| 47 | 80 |
| 48 | 81 |
| 49 | 82 |
| 50 | 83 |
| 51 | 84 |
| 52 | 85 |
| 53 | 86 |
| 54 | 87 |
| 55 | 88 |
| 56 | 89 |
| 35-mer peptides of SEQ ID NO:3 | |
| 1 | 35 |
| 2 | 36 |
| 3 | 37 |
| 4 | 38 |
| 5 | 39 |
| 6 | 40 |
| 7 | 41 |
| 8 | 42 |
| 9 | 43 |
| 10 | 44 |
| 11 | 45 |
| 12 | 46 |
| 13 | 47 |
| 14 | 48 |
| 15 | 49 |
| 16 | 50 |
| 17 | 51 |
| 18 | 52 |
| 19 | 53 |
| 20 | 54 |
| 21 | 55 |
| 22 | 56 |
| 23 | 57 |
| 24 | 58 |
| 25 | 59 |
| 26 | 60 |
| 27 | 61 |
| 28 | 62 |
| 29 | 63 |
| 30 | 64 |
| 31 | 65 |
| 32 | 66 |
| 33 | 67 |
| 34 | 68 |
| 35 | 69 |
| 36 | 70 |
| 37 | 71 |
| 38 | 72 |
| 39 | 73 |
| 40 | 74 |
| 41 | 75 |
| 42 | 76 |
| 43 | 77 |
| 44 | 78 |
| 45 | 79 |
| 46 | 80 |
| 47 | 81 |
| 48 | 82 |
| 49 | 83 |
| 50 | 84 |
| 51 | 85 |
| 52 | 86 |
| 53 | 87 |
| 54 | 88 |
| 55 | 89 |
| 36-mer peptides of SEQ ID NO:3 | |
| 1 | 36 |
| 2 | 37 |
| 3 | 38 |
| 4 | 39 |
| 5 | 40 |
| 6 | 41 |
| 7 | 42 |
| 8 | 43 |
| 9 | 44 |
| 10 | 45 |
| 11 | 46 |
| 12 | 47 |
| 13 | 48 |
| 14 | 49 |
| 15 | 50 |
| 16 | 51 |
| 17 | 52 |
| 18 | 53 |
| 19 | 54 |
| 20 | 55 |
| 21 | 56 |
| 22 | 57 |
| 23 | 58 |
| 24 | 59 |
| 25 | 60 |
| 26 | 61 |
| 27 | 62 |
| 28 | 63 |
| 29 | 64 |
| 30 | 65 |
| 31 | 66 |
| 32 | 67 |
| 33 | 68 |
| 34 | 69 |
| 35 | 70 |
| 36 | 71 |
| 37 | 72 |
| 38 | 73 |
| 39 | 74 |
| 40 | 75 |
| 41 | 76 |
| 42 | 77 |
| 43 | 78 |
| 44 | 79 |
| 45 | 80 |
| 46 | 81 |
| 47 | 82 |
| 48 | 83 |
| 49 | 84 |
| 50 | 85 |
| 51 | 86 |
| 52 | 87 |
| 53 | 88 |
| 54 | 89 |
| 37-mer peptides of SEQ ID NO:3 | |
| 1 | 37 |
| 2 | 38 |
| 3 | 39 |
| 4 | 40 |
| 5 | 41 |
| 6 | 42 |
| 7 | 43 |
| 8 | 44 |
| 9 | 45 |
| 10 | 46 |
| 11 | 47 |
| 12 | 48 |

TABLE 2-continued

| N-terminal amino acid position | C-terminal amino acid position |
|---|---|
| 13 | 49 |
| 14 | 50 |
| 15 | 51 |
| 16 | 52 |
| 17 | 53 |
| 18 | 54 |
| 19 | 55 |
| 20 | 56 |
| 21 | 57 |
| 22 | 58 |
| 23 | 59 |
| 24 | 60 |
| 25 | 61 |
| 26 | 62 |
| 27 | 63 |
| 28 | 64 |
| 29 | 65 |
| 30 | 66 |
| 31 | 67 |
| 32 | 68 |
| 33 | 69 |
| 34 | 70 |
| 35 | 71 |
| 36 | 72 |
| 37 | 73 |
| 38 | 74 |
| 39 | 75 |
| 40 | 76 |
| 41 | 77 |
| 42 | 78 |
| 43 | 79 |
| 44 | 80 |
| 45 | 81 |
| 46 | 82 |
| 47 | 83 |
| 48 | 84 |
| 49 | 85 |
| 50 | 86 |
| 51 | 87 |
| 52 | 88 |
| 53 | 89 |
| 38-mer peptides of SEQ ID NO:3 | |
| 1 | 38 |
| 2 | 39 |
| 3 | 40 |
| 4 | 41 |
| 5 | 42 |
| 6 | 43 |
| 7 | 44 |
| 8 | 45 |
| 9 | 46 |
| 10 | 47 |
| 11 | 48 |
| 12 | 49 |
| 13 | 50 |
| 14 | 51 |
| 15 | 52 |
| 16 | 53 |
| 17 | 54 |
| 18 | 55 |
| 19 | 56 |
| 20 | 57 |
| 21 | 58 |
| 22 | 59 |
| 23 | 60 |
| 24 | 61 |
| 25 | 62 |
| 26 | 63 |
| 27 | 64 |
| 28 | 65 |
| 29 | 66 |
| 30 | 67 |
| 31 | 68 |
| 32 | 69 |
| 33 | 70 |
| 34 | 71 |
| 35 | 72 |
| 36 | 73 |
| 37 | 74 |
| 38 | 75 |
| 39 | 76 |
| 40 | 77 |
| 41 | 78 |
| 42 | 79 |
| 43 | 80 |
| 44 | 81 |
| 45 | 82 |
| 46 | 83 |
| 47 | 84 |
| 48 | 85 |
| 49 | 86 |
| 50 | 87 |
| 51 | 88 |
| 52 | 89 |
| 39-mer peptides of SEQ ID NO:3 | |
| 1 | 39 |
| 2 | 40 |
| 3 | 41 |
| 4 | 42 |
| 5 | 43 |
| 6 | 44 |
| 7 | 45 |
| 8 | 46 |
| 9 | 47 |
| 10 | 48 |
| 11 | 49 |
| 12 | 50 |
| 13 | 51 |
| 14 | 52 |
| 15 | 53 |
| 16 | 54 |
| 17 | 55 |
| 18 | 56 |
| 19 | 57 |
| 20 | 58 |
| 21 | 59 |
| 22 | 60 |
| 23 | 61 |
| 24 | 62 |
| 25 | 63 |
| 26 | 64 |
| 27 | 65 |
| 28 | 66 |
| 29 | 67 |
| 30 | 68 |
| 31 | 69 |
| 32 | 70 |
| 33 | 71 |
| 34 | 72 |
| 35 | 73 |
| 36 | 74 |
| 37 | 75 |
| 38 | 76 |
| 39 | 77 |
| 40 | 78 |
| 41 | 79 |
| 42 | 80 |
| 43 | 81 |
| 44 | 82 |
| 45 | 83 |
| 46 | 84 |
| 47 | 85 |
| 48 | 86 |
| 49 | 87 |
| 50 | 88 |
| 51 | 89 |
| 40-mer peptides of SEQ ID NO:3 | |
| 1 | 40 |
| 2 | 41 |

TABLE 2-continued

| N-terminal amino acid position | C-terminal amino acid position |
|---|---|
| 3 | 42 |
| 4 | 43 |
| 5 | 44 |
| 6 | 45 |
| 7 | 46 |
| 8 | 47 |
| 9 | 48 |
| 10 | 49 |
| 11 | 50 |
| 12 | 51 |
| 13 | 52 |
| 14 | 53 |
| 15 | 54 |
| 16 | 55 |
| 17 | 56 |
| 18 | 57 |
| 19 | 58 |
| 20 | 59 |
| 21 | 60 |
| 22 | 61 |
| 23 | 62 |
| 24 | 63 |
| 25 | 64 |
| 26 | 65 |
| 27 | 66 |
| 28 | 67 |
| 29 | 68 |
| 30 | 69 |
| 31 | 70 |
| 32 | 71 |
| 33 | 72 |
| 34 | 73 |
| 35 | 74 |
| 36 | 75 |
| 37 | 76 |
| 38 | 77 |
| 39 | 78 |
| 40 | 79 |
| 41 | 80 |
| 42 | 81 |
| 43 | 82 |
| 44 | 83 |
| 45 | 84 |
| 46 | 85 |
| 47 | 86 |
| 48 | 87 |
| 49 | 88 |
| 50 | 89 |
| 41-mer peptides of SEQ ID NO:3 | |
| 1 | 41 |
| 2 | 42 |
| 3 | 43 |
| 4 | 44 |
| 5 | 45 |
| 6 | 46 |
| 7 | 47 |
| 8 | 48 |
| 9 | 49 |
| 10 | 50 |
| 11 | 51 |
| 12 | 52 |
| 13 | 53 |
| 14 | 54 |
| 15 | 55 |
| 16 | 56 |
| 17 | 57 |
| 18 | 58 |
| 19 | 59 |
| 20 | 60 |
| 21 | 61 |
| 22 | 62 |
| 23 | 63 |
| 24 | 64 |
| 25 | 65 |
| 26 | 66 |
| 27 | 67 |
| 28 | 68 |
| 29 | 69 |
| 30 | 70 |
| 31 | 71 |
| 32 | 72 |
| 33 | 73 |
| 34 | 74 |
| 35 | 75 |
| 36 | 76 |
| 37 | 77 |
| 38 | 78 |
| 39 | 79 |
| 40 | 80 |
| 41 | 81 |
| 42 | 82 |
| 43 | 83 |
| 44 | 84 |
| 45 | 85 |
| 46 | 86 |
| 47 | 87 |
| 48 | 88 |
| 49 | 89 |
| 42-mer peptides of SEQ ID NO:3 | |
| 1 | 42 |
| 2 | 43 |
| 3 | 44 |
| 4 | 45 |
| 5 | 46 |
| 6 | 47 |
| 7 | 48 |
| 8 | 49 |
| 9 | 50 |
| 10 | 51 |
| 11 | 52 |
| 12 | 53 |
| 13 | 54 |
| 14 | 55 |
| 15 | 56 |
| 16 | 57 |
| 17 | 58 |
| 18 | 59 |
| 19 | 60 |
| 20 | 61 |
| 21 | 62 |
| 22 | 63 |
| 23 | 64 |
| 24 | 65 |
| 25 | 66 |
| 26 | 67 |
| 27 | 68 |
| 28 | 69 |
| 29 | 70 |
| 30 | 71 |
| 31 | 72 |
| 32 | 73 |
| 33 | 74 |
| 34 | 75 |
| 35 | 76 |
| 36 | 77 |
| 37 | 78 |
| 38 | 79 |
| 39 | 80 |
| 40 | 81 |
| 41 | 82 |
| 42 | 83 |
| 43 | 84 |
| 44 | 85 |
| 45 | 86 |
| 46 | 87 |
| 47 | 88 |
| 48 | 89 |

TABLE 2-continued

| N-terminal amino acid position | C-terminal amino acid position |
|---|---|
| 43-mer peptides of SEQ ID NO:3 | |
| 1 | 43 |
| 2 | 44 |
| 3 | 45 |
| 4 | 46 |
| 5 | 47 |
| 6 | 48 |
| 7 | 49 |
| 8 | 50 |
| 9 | 51 |
| 10 | 52 |
| 11 | 53 |
| 12 | 54 |
| 13 | 55 |
| 14 | 56 |
| 15 | 57 |
| 16 | 58 |
| 17 | 59 |
| 18 | 60 |
| 19 | 61 |
| 20 | 62 |
| 21 | 63 |
| 22 | 64 |
| 23 | 65 |
| 24 | 66 |
| 25 | 67 |
| 26 | 68 |
| 27 | 69 |
| 28 | 70 |
| 29 | 71 |
| 30 | 72 |
| 31 | 73 |
| 32 | 74 |
| 33 | 75 |
| 34 | 76 |
| 35 | 77 |
| 36 | 78 |
| 37 | 79 |
| 38 | 80 |
| 39 | 81 |
| 40 | 82 |
| 41 | 83 |
| 42 | 84 |
| 43 | 85 |
| 44 | 86 |
| 45 | 87 |
| 46 | 88 |
| 47 | 89 |
| 44-mer peptides of SEQ ID NO:3 | |
| 1 | 44 |
| 2 | 45 |
| 3 | 46 |
| 4 | 47 |
| 5 | 48 |
| 6 | 49 |
| 7 | 50 |
| 8 | 51 |
| 9 | 52 |
| 10 | 53 |
| 11 | 54 |
| 12 | 55 |
| 13 | 56 |
| 14 | 57 |
| 15 | 58 |
| 16 | 59 |
| 17 | 60 |
| 18 | 61 |
| 19 | 62 |
| 20 | 63 |
| 21 | 64 |
| 22 | 65 |
| 23 | 66 |
| 24 | 67 |
| 25 | 68 |
| 26 | 69 |
| 27 | 70 |
| 28 | 71 |
| 29 | 72 |
| 30 | 73 |
| 31 | 74 |
| 32 | 75 |
| 33 | 76 |
| 34 | 77 |
| 35 | 78 |
| 36 | 79 |
| 37 | 80 |
| 38 | 81 |
| 39 | 82 |
| 40 | 83 |
| 41 | 84 |
| 42 | 85 |
| 43 | 86 |
| 44 | 87 |
| 45 | 88 |
| 46 | 89 |
| 45-mer peptides of SEQ ID NO:3 | |
| 1 | 45 |
| 2 | 46 |
| 3 | 47 |
| 4 | 48 |
| 5 | 49 |
| 6 | 50 |
| 7 | 51 |
| 8 | 52 |
| 9 | 53 |
| 10 | 54 |
| 11 | 55 |
| 12 | 56 |
| 13 | 57 |
| 14 | 58 |
| 15 | 59 |
| 16 | 60 |
| 17 | 61 |
| 18 | 62 |
| 19 | 63 |
| 20 | 64 |
| 21 | 65 |
| 22 | 66 |
| 23 | 67 |
| 24 | 68 |
| 25 | 69 |
| 26 | 70 |
| 27 | 71 |
| 28 | 72 |
| 29 | 73 |
| 30 | 74 |
| 31 | 75 |
| 32 | 76 |
| 33 | 77 |
| 34 | 78 |
| 35 | 79 |
| 36 | 80 |
| 37 | 81 |
| 38 | 82 |
| 39 | 83 |
| 40 | 84 |
| 41 | 85 |
| 42 | 86 |
| 43 | 87 |
| 44 | 88 |
| 45 | 89 |
| 46-mer peptides of SEQ ID NO:3 | |
| 1 | 46 |
| 2 | 47 |
| 3 | 48 |
| 4 | 49 |
| 5 | 50 |
| 6 | 51 |

TABLE 2-continued

| N-terminal amino acid position | C-terminal amino acid position |
|---|---|
| 7 | 52 |
| 8 | 53 |
| 9 | 54 |
| 10 | 55 |
| 11 | 56 |
| 12 | 57 |
| 13 | 58 |
| 14 | 59 |
| 15 | 60 |
| 16 | 61 |
| 17 | 62 |
| 18 | 63 |
| 19 | 64 |
| 20 | 65 |
| 21 | 66 |
| 22 | 67 |
| 23 | 68 |
| 24 | 69 |
| 25 | 70 |
| 26 | 71 |
| 27 | 72 |
| 28 | 73 |
| 29 | 74 |
| 30 | 75 |
| 31 | 76 |
| 32 | 77 |
| 33 | 78 |
| 34 | 79 |
| 35 | 80 |
| 36 | 81 |
| 37 | 82 |
| 38 | 83 |
| 39 | 84 |
| 40 | 85 |
| 41 | 86 |
| 42 | 87 |
| 43 | 88 |
| 44 | 89 |
| 47-mer peptides of SEQ ID NO:3 | |
| 1 | 47 |
| 2 | 48 |
| 3 | 49 |
| 4 | 50 |
| 5 | 51 |
| 6 | 52 |
| 7 | 53 |
| 8 | 54 |
| 9 | 55 |
| 10 | 56 |
| 11 | 57 |
| 12 | 58 |
| 13 | 59 |
| 14 | 60 |
| 15 | 61 |
| 16 | 62 |
| 17 | 63 |
| 18 | 64 |
| 19 | 65 |
| 20 | 66 |
| 21 | 67 |
| 22 | 68 |
| 23 | 69 |
| 24 | 70 |
| 25 | 71 |
| 26 | 72 |
| 27 | 73 |
| 28 | 74 |
| 29 | 75 |
| 30 | 76 |
| 31 | 77 |
| 32 | 78 |
| 33 | 79 |
| 34 | 80 |
| 35 | 81 |
| 36 | 82 |
| 37 | 83 |
| 38 | 84 |
| 39 | 85 |
| 40 | 86 |
| 41 | 87 |
| 42 | 88 |
| 43 | 89 |
| 48-mer peptides of SEQ ID NO:3 | |
| 1 | 48 |
| 2 | 49 |
| 3 | 50 |
| 4 | 51 |
| 5 | 52 |
| 6 | 53 |
| 7 | 54 |
| 8 | 55 |
| 9 | 56 |
| 10 | 57 |
| 11 | 58 |
| 12 | 59 |
| 13 | 60 |
| 14 | 61 |
| 15 | 62 |
| 16 | 63 |
| 17 | 64 |
| 18 | 65 |
| 19 | 66 |
| 20 | 67 |
| 21 | 68 |
| 22 | 69 |
| 23 | 70 |
| 24 | 71 |
| 25 | 72 |
| 26 | 73 |
| 27 | 74 |
| 28 | 75 |
| 29 | 76 |
| 30 | 77 |
| 31 | 78 |
| 32 | 79 |
| 33 | 80 |
| 34 | 81 |
| 35 | 82 |
| 36 | 83 |
| 37 | 84 |
| 38 | 85 |
| 39 | 86 |
| 40 | 87 |
| 41 | 88 |
| 42 | 89 |
| 49-mer peptides of SEQ ID NO:3 | |
| 1 | 49 |
| 2 | 50 |
| 3 | 51 |
| 4 | 52 |
| 5 | 53 |
| 6 | 54 |
| 7 | 55 |
| 8 | 56 |
| 9 | 57 |
| 10 | 58 |
| 11 | 59 |
| 12 | 60 |
| 13 | 61 |
| 14 | 62 |
| 15 | 63 |
| 16 | 64 |
| 17 | 65 |
| 18 | 66 |
| 19 | 67 |
| 20 | 68 |
| 21 | 69 |
| 22 | 70 |
| 23 | 71 |

TABLE 2-continued

| N-terminal amino acid position | C-terminal amino acid position |
|---|---|
| 24 | 72 |
| 25 | 73 |
| 26 | 74 |
| 27 | 75 |
| 28 | 76 |
| 29 | 77 |
| 30 | 78 |
| 31 | 79 |
| 32 | 80 |
| 33 | 81 |
| 34 | 82 |
| 35 | 83 |
| 36 | 84 |
| 37 | 85 |
| 38 | 86 |
| 39 | 87 |
| 40 | 88 |
| 41 | 89 |
| 50-mer peptides of SEQ ID NO:3 | |
| 1 | 50 |
| 2 | 51 |
| 3 | 52 |
| 4 | 53 |
| 5 | 54 |
| 6 | 55 |
| 7 | 56 |
| 8 | 57 |
| 9 | 58 |
| 10 | 59 |
| 11 | 60 |
| 12 | 61 |
| 13 | 62 |
| 14 | 63 |
| 15 | 64 |
| 16 | 65 |
| 17 | 66 |
| 18 | 67 |
| 19 | 68 |
| 20 | 69 |
| 21 | 70 |
| 22 | 71 |
| 23 | 72 |
| 24 | 73 |
| 25 | 74 |
| 26 | 75 |
| 27 | 76 |
| 28 | 77 |
| 29 | 78 |
| 30 | 79 |
| 31 | 80 |
| 32 | 81 |
| 33 | 82 |
| 34 | 83 |
| 35 | 84 |
| 36 | 85 |
| 37 | 86 |
| 38 | 87 |
| 39 | 88 |
| 40 | 89 |
| 51-mer peptides of SEQ ID NO:3 | |
| 1 | 51 |
| 2 | 52 |
| 3 | 53 |
| 4 | 54 |
| 5 | 55 |
| 6 | 56 |
| 7 | 57 |
| 8 | 58 |
| 9 | 59 |
| 10 | 60 |
| 11 | 61 |
| 12 | 62 |
| 13 | 63 |
| 14 | 64 |
| 15 | 65 |
| 16 | 66 |
| 17 | 67 |
| 18 | 68 |
| 19 | 69 |
| 20 | 70 |
| 21 | 71 |
| 22 | 72 |
| 23 | 73 |
| 24 | 74 |
| 25 | 75 |
| 26 | 76 |
| 27 | 77 |
| 28 | 78 |
| 29 | 79 |
| 30 | 80 |
| 31 | 81 |
| 32 | 82 |
| 33 | 83 |
| 34 | 84 |
| 35 | 85 |
| 36 | 86 |
| 37 | 87 |
| 38 | 88 |
| 39 | 89 |
| 52-mer peptides of SEQ ID NO:3 | |
| 1 | 52 |
| 2 | 53 |
| 3 | 54 |
| 4 | 55 |
| 5 | 56 |
| 6 | 57 |
| 7 | 58 |
| 8 | 59 |
| 9 | 60 |
| 10 | 61 |
| 11 | 62 |
| 12 | 63 |
| 13 | 64 |
| 14 | 65 |
| 15 | 66 |
| 16 | 67 |
| 17 | 68 |
| 18 | 69 |
| 19 | 70 |
| 20 | 71 |
| 21 | 72 |
| 22 | 73 |
| 23 | 74 |
| 24 | 75 |
| 25 | 76 |
| 26 | 77 |
| 27 | 78 |
| 28 | 79 |
| 29 | 80 |
| 30 | 81 |
| 31 | 82 |
| 32 | 83 |
| 33 | 84 |
| 34 | 85 |
| 35 | 86 |
| 36 | 87 |
| 37 | 88 |
| 38 | 89 |
| 53-mer peptides of SEQ ID NO:3 | |
| 1 | 53 |
| 2 | 54 |
| 3 | 55 |
| 4 | 56 |
| 5 | 57 |
| 6 | 58 |
| 7 | 59 |
| 8 | 60 |
| 9 | 61 |

TABLE 2-continued

| N-terminal amino acid position | C-terminal amino acid position |
|---|---|
| 10 | 62 |
| 11 | 63 |
| 12 | 64 |
| 13 | 65 |
| 14 | 66 |
| 15 | 67 |
| 16 | 68 |
| 17 | 69 |
| 18 | 70 |
| 19 | 71 |
| 20 | 72 |
| 21 | 73 |
| 22 | 74 |
| 23 | 75 |
| 24 | 76 |
| 25 | 77 |
| 26 | 78 |
| 27 | 79 |
| 28 | 80 |
| 29 | 81 |
| 30 | 82 |
| 31 | 83 |
| 32 | 84 |
| 33 | 85 |
| 34 | 86 |
| 35 | 87 |
| 36 | 88 |
| 37 | 89 |

54-mer peptides of SEQ ID NO:3

| N-terminal amino acid position | C-terminal amino acid position |
|---|---|
| 1 | 54 |
| 2 | 55 |
| 3 | 56 |
| 4 | 57 |
| 5 | 58 |
| 6 | 59 |
| 7 | 60 |
| 8 | 61 |
| 9 | 62 |
| 10 | 63 |
| 11 | 64 |
| 12 | 65 |
| 13 | 66 |
| 14 | 67 |
| 15 | 68 |
| 16 | 69 |
| 17 | 70 |
| 18 | 71 |
| 19 | 72 |
| 20 | 73 |
| 21 | 74 |
| 22 | 75 |
| 23 | 76 |
| 24 | 77 |
| 25 | 78 |
| 26 | 79 |
| 27 | 80 |
| 28 | 81 |
| 29 | 82 |
| 30 | 83 |
| 31 | 84 |
| 32 | 85 |
| 33 | 86 |
| 34 | 87 |
| 35 | 88 |
| 36 | 89 |

55-mer peptides of SEQ ID NO:3

| N-terminal amino acid position | C-terminal amino acid position |
|---|---|
| 1 | 55 |
| 2 | 56 |
| 3 | 57 |
| 4 | 58 |
| 5 | 59 |
| 6 | 60 |
| 7 | 61 |
| 8 | 62 |
| 9 | 63 |
| 10 | 64 |
| 11 | 65 |
| 12 | 66 |
| 13 | 67 |
| 14 | 68 |
| 15 | 69 |
| 16 | 70 |
| 17 | 71 |
| 18 | 72 |
| 19 | 73 |
| 20 | 74 |
| 21 | 75 |
| 22 | 76 |
| 23 | 77 |
| 24 | 78 |
| 25 | 79 |
| 26 | 80 |
| 27 | 81 |
| 28 | 82 |
| 29 | 83 |
| 30 | 84 |
| 31 | 85 |
| 32 | 86 |
| 33 | 87 |
| 34 | 88 |
| 35 | 89 |

56-mer peptides of SEQ ID NO:3

| N-terminal amino acid position | C-terminal amino acid position |
|---|---|
| 1 | 56 |
| 2 | 57 |
| 3 | 58 |
| 4 | 59 |
| 5 | 60 |
| 6 | 61 |
| 7 | 62 |
| 8 | 63 |
| 9 | 64 |
| 10 | 65 |
| 11 | 66 |
| 12 | 67 |
| 13 | 68 |
| 14 | 69 |
| 15 | 70 |
| 16 | 71 |
| 17 | 72 |
| 18 | 73 |
| 19 | 74 |
| 20 | 75 |
| 21 | 76 |
| 22 | 77 |
| 23 | 78 |
| 24 | 79 |
| 25 | 80 |
| 26 | 81 |
| 27 | 82 |
| 28 | 83 |
| 29 | 84 |
| 30 | 85 |
| 31 | 86 |
| 32 | 87 |
| 33 | 88 |
| 34 | 89 |

57-mer peptides of SEQ ID NO:3

| N-terminal amino acid position | C-terminal amino acid position |
|---|---|
| 1 | 57 |
| 2 | 58 |
| 3 | 59 |
| 4 | 60 |
| 5 | 61 |
| 6 | 62 |
| 7 | 63 |
| 8 | 64 |
| 9 | 65 |
| 10 | 66 |
| 11 | 67 |

TABLE 2-continued

| N-terminal amino acid position | C-terminal amino acid position |
|---|---|
| 12 | 68 |
| 13 | 69 |
| 14 | 70 |
| 15 | 71 |
| 16 | 72 |
| 17 | 73 |
| 18 | 74 |
| 19 | 75 |
| 20 | 76 |
| 21 | 77 |
| 22 | 78 |
| 23 | 79 |
| 24 | 80 |
| 25 | 81 |
| 26 | 82 |
| 27 | 83 |
| 28 | 84 |
| 29 | 85 |
| 30 | 86 |
| 31 | 87 |
| 32 | 88 |
| 33 | 89 |
| 58-mer peptides of SEQ ID NO:3 | |
| 1 | 58 |
| 2 | 59 |
| 3 | 60 |
| 4 | 61 |
| 5 | 62 |
| 6 | 63 |
| 7 | 64 |
| 8 | 65 |
| 9 | 66 |
| 10 | 67 |
| 11 | 68 |
| 12 | 69 |
| 13 | 70 |
| 14 | 71 |
| 15 | 72 |
| 16 | 73 |
| 17 | 74 |
| 18 | 75 |
| 19 | 76 |
| 20 | 77 |
| 21 | 78 |
| 22 | 79 |
| 23 | 80 |
| 24 | 81 |
| 25 | 82 |
| 26 | 83 |
| 27 | 84 |
| 28 | 85 |
| 29 | 86 |
| 30 | 87 |
| 31 | 88 |
| 32 | 89 |
| 59-mer peptides of SEQ ID NO:3 | |
| 1 | 59 |
| 2 | 60 |
| 3 | 61 |
| 4 | 62 |
| 5 | 63 |
| 6 | 64 |
| 7 | 65 |
| 8 | 66 |
| 9 | 67 |
| 10 | 68 |
| 11 | 69 |
| 12 | 70 |
| 13 | 71 |
| 14 | 72 |
| 15 | 73 |
| 16 | 74 |
| 17 | 75 |
| 18 | 76 |
| 19 | 77 |
| 20 | 78 |
| 21 | 79 |
| 22 | 80 |
| 23 | 81 |
| 24 | 82 |
| 25 | 83 |
| 26 | 84 |
| 27 | 85 |
| 28 | 86 |
| 29 | 87 |
| 30 | 88 |
| 31 | 89 |
| 60-mer peptides of SEQ ID NO:3 | |
| 1 | 60 |
| 2 | 61 |
| 3 | 62 |
| 4 | 63 |
| 5 | 64 |
| 6 | 65 |
| 7 | 66 |
| 8 | 67 |
| 9 | 68 |
| 10 | 69 |
| 11 | 70 |
| 12 | 71 |
| 13 | 72 |
| 14 | 73 |
| 15 | 74 |
| 16 | 75 |
| 17 | 76 |
| 18 | 77 |
| 19 | 78 |
| 20 | 79 |
| 21 | 80 |
| 22 | 81 |
| 23 | 82 |
| 24 | 83 |
| 25 | 84 |
| 26 | 85 |
| 27 | 86 |
| 28 | 87 |
| 29 | 88 |
| 30 | 89 |
| 5-mer peptides of SEQ ID NO:4 | |
| 1 | 5 |
| 2 | 6 |
| 3 | 7 |
| 4 | 8 |
| 5 | 9 |
| 6 | 10 |
| 7 | 11 |
| 8 | 12 |
| 9 | 13 |
| 10 | 14 |
| 6-mer peptides of SEQ ID NO:4 | |
| 1 | 6 |
| 2 | 7 |
| 3 | 8 |
| 4 | 9 |
| 5 | 10 |
| 6 | 11 |
| 7 | 12 |
| 8 | 13 |
| 9 | 14 |
| 7-mer peptides of SEQ ID NO:4 | |
| 1 | 7 |
| 2 | 8 |
| 3 | 9 |
| 4 | 10 |
| 5 | 11 |
| 6 | 12 |

TABLE 2-continued

| N-terminal amino acid position | C-terminal amino acid position |
|---|---|
| 7 | 13 |
| 8 | 14 |
| 8-mer peptides of SEQ ID NO:4 | |
| 1 | 8 |
| 2 | 9 |
| 3 | 10 |
| 4 | 11 |
| 5 | 12 |
| 6 | 13 |
| 7 | 14 |
| 61-mer peptides of SEQ ID NO:3 | |
| 1 | 61 |
| 2 | 62 |
| 3 | 63 |
| 4 | 64 |
| 5 | 65 |
| 6 | 66 |
| 7 | 67 |
| 8 | 68 |
| 9 | 69 |
| 10 | 70 |
| 11 | 71 |
| 12 | 72 |
| 13 | 73 |
| 14 | 74 |
| 15 | 75 |
| 16 | 76 |
| 17 | 77 |
| 18 | 78 |
| 19 | 79 |
| 20 | 80 |
| 21 | 81 |
| 22 | 82 |
| 23 | 83 |
| 24 | 84 |
| 25 | 85 |
| 26 | 86 |
| 27 | 87 |
| 28 | 88 |
| 29 | 89 |
| 62-mer peptides of SEQ ID NO:3 | |
| 1 | 62 |
| 2 | 63 |
| 3 | 64 |
| 4 | 65 |
| 5 | 66 |
| 6 | 67 |
| 7 | 68 |
| 8 | 69 |
| 9 | 70 |
| 10 | 71 |
| 11 | 72 |
| 12 | 73 |
| 13 | 74 |
| 14 | 75 |
| 15 | 76 |
| 16 | 77 |
| 17 | 78 |
| 18 | 79 |
| 19 | 80 |
| 20 | 81 |
| 21 | 82 |
| 22 | 83 |
| 23 | 84 |
| 24 | 85 |
| 25 | 86 |
| 26 | 87 |
| 27 | 88 |
| 28 | 89 |
| 63-mer peptides of SEQ ID NO:3 | |
| 1 | 63 |
| 2 | 64 |

TABLE 2-continued

| N-terminal amino acid position | C-terminal amino acid position |
|---|---|
| 3 | 65 |
| 4 | 66 |
| 5 | 67 |
| 6 | 68 |
| 7 | 69 |
| 8 | 70 |
| 9 | 71 |
| 10 | 72 |
| 11 | 73 |
| 12 | 74 |
| 13 | 75 |
| 14 | 76 |
| 15 | 77 |
| 16 | 78 |
| 17 | 79 |
| 18 | 80 |
| 19 | 81 |
| 20 | 82 |
| 21 | 83 |
| 22 | 84 |
| 23 | 85 |
| 24 | 86 |
| 25 | 87 |
| 26 | 88 |
| 27 | 89 |
| 64-mer peptides of SEQ ID NO:3 | |
| 1 | 64 |
| 2 | 65 |
| 3 | 66 |
| 4 | 67 |
| 5 | 68 |
| 6 | 69 |
| 7 | 70 |
| 8 | 71 |
| 9 | 72 |
| 10 | 73 |
| 11 | 74 |
| 12 | 75 |
| 13 | 76 |
| 14 | 77 |
| 15 | 78 |
| 16 | 79 |
| 17 | 80 |
| 18 | 81 |
| 19 | 82 |
| 20 | 83 |
| 21 | 84 |
| 22 | 85 |
| 23 | 86 |
| 24 | 87 |
| 25 | 88 |
| 26 | 89 |
| 9-mer peptides of SEQ ID NO:4 | |
| 1 | 9 |
| 2 | 10 |
| 3 | 11 |
| 4 | 12 |
| 5 | 13 |
| 6 | 14 |
| 10-mer peptides of SEQ ID NO:4 | |
| 1 | 10 |
| 2 | 11 |
| 3 | 12 |
| 4 | 13 |
| 5 | 14 |
| 11-mer peptides of SEQ ID NO:4 | |
| 1 | 11 |
| 2 | 12 |
| 3 | 13 |
| 4 | 14 |

TABLE 2-continued

| N-terminal amino acid position | C-terminal amino acid position |
|---|---|
| 12-mer peptides of SEQ ID NO:4 | |
| 1 | 12 |
| 2 | 13 |
| 3 | 14 |
| 13-mer peptides of SEQ ID NO:4 | |
| 1 | 13 |
| 2 | 14 |
| 65-mer peptides of SEQ ID NO:3 | |
| 1 | 65 |
| 2 | 66 |
| 3 | 67 |
| 4 | 68 |
| 5 | 69 |
| 6 | 70 |
| 7 | 71 |
| 8 | 72 |
| 9 | 73 |
| 10 | 74 |
| 11 | 75 |
| 12 | 76 |
| 13 | 77 |
| 14 | 78 |
| 15 | 79 |
| 16 | 80 |
| 17 | 81 |
| 18 | 82 |
| 19 | 83 |
| 20 | 84 |
| 21 | 85 |
| 22 | 86 |
| 23 | 87 |
| 24 | 88 |
| 25 | 89 |
| 66-mer peptides of SEQ ID NO:3 | |
| 1 | 66 |
| 2 | 67 |
| 3 | 68 |
| 4 | 69 |
| 5 | 70 |
| 6 | 71 |
| 7 | 72 |
| 8 | 73 |
| 9 | 74 |
| 10 | 75 |
| 11 | 76 |
| 12 | 77 |
| 13 | 78 |
| 14 | 79 |
| 15 | 80 |
| 16 | 81 |
| 17 | 82 |
| 18 | 83 |
| 19 | 84 |
| 20 | 85 |
| 21 | 86 |
| 22 | 87 |
| 23 | 88 |
| 24 | 89 |
| 67-mer peptides of SEQ ID NO:3 | |
| 1 | 67 |
| 2 | 68 |
| 3 | 69 |
| 4 | 70 |
| 5 | 71 |
| 6 | 72 |
| 7 | 73 |
| 8 | 74 |
| 9 | 75 |
| 10 | 76 |
| 11 | 77 |
| 12 | 78 |
| 13 | 79 |
| 14 | 80 |
| 15 | 81 |
| 16 | 82 |
| 17 | 83 |
| 18 | 84 |
| 19 | 85 |
| 20 | 86 |
| 21 | 87 |
| 22 | 88 |
| 23 | 89 |
| 68-mer peptides of SEQ ID NO:3 | |
| 1 | 68 |
| 2 | 69 |
| 3 | 70 |
| 4 | 71 |
| 5 | 72 |
| 6 | 73 |
| 7 | 74 |
| 8 | 75 |
| 9 | 76 |
| 10 | 77 |
| 11 | 78 |
| 12 | 79 |
| 13 | 80 |
| 14 | 81 |
| 15 | 82 |
| 16 | 83 |
| 17 | 84 |
| 18 | 85 |
| 19 | 86 |
| 20 | 87 |
| 21 | 88 |
| 22 | 89 |
| 69-mer peptides of SEQ ID NO:3 | |
| 1 | 69 |
| 2 | 70 |
| 3 | 71 |
| 4 | 72 |
| 5 | 73 |
| 6 | 74 |
| 7 | 75 |
| 8 | 76 |
| 9 | 77 |
| 10 | 78 |
| 11 | 79 |
| 12 | 80 |
| 13 | 81 |
| 14 | 82 |
| 15 | 83 |
| 16 | 84 |
| 17 | 85 |
| 18 | 86 |
| 19 | 87 |
| 20 | 88 |
| 21 | 89 |
| 70-mer peptides of SEQ ID NO:3 | |
| 1 | 70 |
| 2 | 71 |
| 3 | 72 |
| 4 | 73 |
| 5 | 74 |
| 6 | 75 |
| 7 | 76 |
| 8 | 77 |
| 9 | 78 |
| 10 | 79 |
| 11 | 80 |
| 12 | 81 |
| 13 | 82 |
| 14 | 83 |
| 15 | 84 |
| 16 | 85 |

TABLE 2-continued

| N-terminal amino acid position | C-terminal amino acid position |
|---|---|
| 17 | 86 |
| 18 | 87 |
| 19 | 88 |
| 20 | 89 |
| 71-mer peptides of SEQ ID NO:3 | |
| 1 | 71 |
| 2 | 72 |
| 3 | 73 |
| 4 | 74 |
| 5 | 75 |
| 6 | 76 |
| 7 | 77 |
| 8 | 78 |
| 9 | 79 |
| 10 | 80 |
| 11 | 81 |
| 12 | 82 |
| 13 | 83 |
| 14 | 84 |
| 15 | 85 |
| 16 | 86 |
| 17 | 87 |
| 18 | 88 |
| 19 | 89 |
| 72-mer peptides of SEQ ID NO:3 | |
| 1 | 72 |
| 2 | 73 |
| 3 | 74 |
| 4 | 75 |
| 5 | 76 |
| 6 | 77 |
| 7 | 78 |
| 8 | 79 |
| 9 | 80 |
| 10 | 81 |
| 11 | 82 |
| 12 | 83 |
| 13 | 84 |
| 14 | 85 |
| 15 | 86 |
| 16 | 87 |
| 17 | 88 |
| 18 | 89 |
| 73-mer peptides of SEQ ID NO:3 | |
| 1 | 73 |
| 2 | 74 |
| 3 | 75 |
| 4 | 76 |
| 5 | 77 |
| 6 | 78 |
| 7 | 79 |
| 8 | 80 |
| 9 | 81 |
| 10 | 82 |
| 11 | 83 |
| 12 | 84 |
| 13 | 85 |
| 14 | 86 |
| 15 | 87 |
| 16 | 88 |
| 17 | 89 |
| 74-mer peptides of SEQ ID NO:3 | |
| 1 | 74 |
| 2 | 75 |
| 3 | 76 |
| 4 | 77 |
| 5 | 78 |
| 6 | 79 |
| 7 | 80 |
| 8 | 81 |
| 9 | 82 |
| 10 | 83 |
| 11 | 84 |
| 12 | 85 |
| 13 | 86 |
| 14 | 87 |
| 15 | 88 |
| 16 | 89 |
| 75-mer peptides of SEQ ID NO:3 | |
| 1 | 75 |
| 2 | 76 |
| 3 | 77 |
| 4 | 78 |
| 5 | 79 |
| 6 | 80 |
| 7 | 81 |
| 8 | 82 |
| 9 | 83 |
| 10 | 84 |
| 11 | 85 |
| 12 | 86 |
| 13 | 87 |
| 14 | 88 |
| 15 | 89 |
| 76-mer peptides of SEQ ID NO:3 | |
| 1 | 76 |
| 2 | 77 |
| 3 | 78 |
| 4 | 79 |
| 5 | 80 |
| 6 | 81 |
| 7 | 82 |
| 8 | 83 |
| 9 | 84 |
| 10 | 85 |
| 11 | 86 |
| 12 | 87 |
| 13 | 88 |
| 14 | 89 |
| 77-mer peptides of SEQ ID NO:3 | |
| 1 | 77 |
| 2 | 70 |
| 3 | 71 |
| 4 | 72 |
| 5 | 73 |
| 6 | 74 |
| 7 | 75 |
| 8 | 76 |
| 9 | 77 |
| 10 | 78 |
| 11 | 79 |
| 12 | 80 |
| 13 | 81 |
| 14 | 82 |
| 15 | 83 |
| 16 | 84 |
| 17 | 85 |
| 18 | 86 |
| 19 | 87 |
| 20 | 88 |
| 21 | 89 |
| 78-mer peptides of SEQ ID NO:3 | |
| 1 | 78 |
| 2 | 71 |
| 3 | 72 |
| 4 | 73 |
| 5 | 74 |
| 6 | 75 |
| 7 | 76 |
| 8 | 77 |
| 9 | 78 |
| 10 | 79 |
| 11 | 80 |
| 12 | 81 |

TABLE 2-continued

| N-terminal amino acid position | C-terminal amino acid position |
|---|---|
| 13 | 82 |
| 14 | 83 |
| 15 | 84 |
| 16 | 85 |
| 17 | 86 |
| 18 | 87 |
| 19 | 88 |
| 20 | 89 |
| 79-mer peptides of SEQ ID NO:3 | |
| 1 | 79 |
| 2 | 72 |
| 3 | 73 |
| 4 | 74 |
| 5 | 75 |
| 6 | 76 |
| 7 | 77 |
| 8 | 78 |
| 9 | 79 |
| 10 | 80 |
| 11 | 81 |
| 12 | 82 |
| 13 | 83 |
| 14 | 84 |
| 15 | 85 |
| 16 | 86 |
| 17 | 87 |
| 18 | 88 |
| 19 | 89 |
| 80-mer peptides of SEQ ID NO:3 | |
| 1 | 80 |
| 2 | 73 |
| 3 | 74 |
| 4 | 75 |
| 5 | 76 |
| 6 | 77 |
| 7 | 78 |
| 8 | 79 |
| 9 | 80 |
| 10 | 81 |
| 11 | 82 |
| 12 | 83 |
| 13 | 84 |
| 14 | 85 |
| 15 | 86 |
| 16 | 87 |
| 17 | 88 |
| 18 | 89 |
| 81-mer peptides of SEQ ID NO:3 | |
| 1 | 81 |
| 2 | 82 |
| 3 | 83 |
| 4 | 84 |
| 5 | 85 |
| 6 | 86 |
| 7 | 87 |
| 8 | 88 |
| 9 | 89 |
| 82-mer peptides of SEQ ID NO:3 | |
| 1 | 82 |
| 2 | 83 |
| 3 | 84 |
| 4 | 85 |
| 5 | 86 |
| 6 | 87 |
| 7 | 88 |
| 8 | 89 |
| 83-mer peptides of SEQ ID NO:3 | |
| 1 | 83 |
| 2 | 84 |
| 3 | 85 |
| 4 | 86 |
| 5 | 87 |
| 6 | 88 |
| 7 | 89 |
| 84-mer peptides of SEQ ID NO:3 | |
| 1 | 84 |
| 2 | 85 |
| 3 | 86 |
| 4 | 87 |
| 5 | 88 |
| 6 | 89 |
| 85-mer peptides of SEQ ID NO:3 | |
| 1 | 85 |
| 2 | 86 |
| 3 | 87 |
| 4 | 88 |
| 5 | 89 |
| 86-mer peptides of SEQ ID NO:3 | |
| 1 | 86 |
| 2 | 87 |
| 3 | 88 |
| 4 | 89 |
| 87-mer peptides of SEQ ID NO:3 | |
| 1 | 87 |
| 2 | 88 |
| 3 | 89 |
| 88-mer peptides of SEQ ID NO:3 | |
| 1 | 88 |
| 2 | 89 |

TABLE 3

| Name of enzyme | No. of cleavages | Positions of cleavage sites within SEQ ID No: 2 (cleavage site is C terminal to amino acid number) |
|---|---|---|
| Asparaginyl endopeptidase | 4 | 16 25 39 52 |
| Cyanogen bromide | 3 | 18 59 62 |
| Chymotrypsin-high specificity (C-term to [FYW], not before P) | 8 | 3 6 8 15 38 54 63 65 |
| Chymotrypsin-low specificity (C-term to [FYWML], not before P) | 18 | 3 4 6 8 15 18 22 35 38 41 54 59 60 61 62 63 65 70 |
| Glutamyl endopeptidase | 2 | 30 45 |
| Lysyl endopeptidase | 5 | 11 12 21 57 69 |
| (2-nitro-5-thiocyanobenzoic acid) | 2 | 67 71 |
| Pepsin (pH = 1.3) | 23 | 2 3 3 4 5 6 7 8 15 21 22 35 37 38 40 41 53 54 61 62 63 64 65 |
| Pepsin (pH > 2) | 19 | 2 3 3 4 15 21 22 35 37 38 40 41 53 54 61 62 63 64 65 |
| Proteinase K | 34 | 1 2 3 4 6 8 9 14 15 20 22 25 27 28 29 32 34 35 36 38 39 41 42 48 49 52 54 55 60 61 63 65 71 74 |
| Staphylococcal peptidase I | 2 | 30 45 |
| Thermolysin | 26 | 1 2 3 8 13 14 19 21 27 28 33 34 35 37 41 47 48 54 58 59 60 61 62 64 70 73 |
| Trypsin | 5 | 11 12 21 57 |

TABLE 4

Supe. 2/3 Negative Controls

| 1 Ab | Normal 1 | Normal 2 | Normal 3 | Normal 4 | Normal 5 |
|---|---|---|---|---|---|
| 1/100 | 0.576 | 0.26 | 0.394 | 0.386 | 0.482 |
| 1/300 | 0.277 | 0.22 | 0.219 | 0.267 | 0.37 |
| 1/1000 | 0.143 | 0.147 | 0.142 | 0.132 | 0.134 |

| 1/100 | 1/300 | 1/1000 |
|---|---|---|
| *N = 5 | *N = 5 | *N = 5 |
| Mean: 0.4196 | Mean: 0.2706 | Mean: 0.1396 |
| *Highest: 0.576 | *Highest: 037 | *Highest: 0.147 |
| *Lowest: 0.26 | *Lowest: 0.219 | *Lowest: 0.132 |
| Variance = 0.316 | Variance = 0.151 | Variance = 0.015 |
| Standard Dev. = 0.079 | S.D. = 0.03775 | S.D. = 0.00375 |
| 2 Stand. Dev. = 0.158 | 2 S.D. = 0.0755 | 2 S.D. = 0.0075 |
| 3 Stand. Dev. = 0.237 | 3 S.D. = 0.11325 | 3 S.D. = 0.01125 |
| 2× Mean: 0.8392 | 2× Mean: 0.5412 | 2× Mean: 0.2792 |
| 2 S.D. + Mean: 0.5776 | 2 S.D. + Mean: 0.3461 | 2 S.D. + Mean: 0.1471 |
| 3 S.D. + Mean: 0.6566 | 3 S.D. + Mean: 0.38385 | 3 S.D. + Mean: 0.15085 |

Supe 2/3

| 1 Ab | #179 | #178 | #80439 | #80255 | #99-01291 |
|---|---|---|---|---|---|
| 1/100 | 0.731 | 1.162 | 1.37 | 1.252 | 0.468 |
| 1/300 | 0.438 | 0.675 | 0.995 | 0.63 | 0.34 |
| 1/1000 | 0.22 | 0.382 | 0.396 | 0.282 | 0.147 |

TABLE 5

Negative Controls

| 1 Ab | Mollie | CN76AC | CN115A Jun. 11, 1998 | CN125C | CN35B |
|---|---|---|---|---|---|
| 1/100 | 1.738 | 2.074 | 2.096 | 2.494 | 1.815 |
| 1/300 | 1.091 | 1.499 | 1.284 | 1.63 | 1.055 |

| 1 Ab | Dixie | CN54B | CN105C | Presley | CN74H |
|---|---|---|---|---|---|
| 1/100 | 1.823 | 2.429 | 2.127 | 1.532 | 1.703 |
| 1/300 | 1.336 | 1.698 | 1.496 | 0.947 | 1.114 |

| 1/100 | 1/300 |
|---|---|
| *N = 10 | *N = 10 |
| Mean: 1.9831 | Mean: 1.315 |
| *Highest: 2.494 | *Highest: 1.698 |
| *Lowest: 1.532 | *Lowest: 0.947 |
| Variance = 0.962 | Variance = 0.751 |
| Standard Dev. = 0.2405 | S.D. = 0.18775 |
| 2 Stand. Dev. = 0.481 | 2 S.D. = 0.3755 |
| 3 Stand. Dev. = 0.7215 | 3 S.D. = 0.56325 |
| 2× Mean: 3.9662 | 2× Mean: 2.63 |
| 2 S.D. + Mean: 2.4641 | 2 S.D. + Mean: 1.6905 |
| 3 S.D. + Mean: 2.7046 | 3 S.D. + Mean: 1.87825 |

TABLE 5-continued

Negative Controls

Supe 2/3

| 1 Ab | Indexx 1 | Indexx 2 | Indexx 3 | Indexx 4 | Indexx 5 |
|---|---|---|---|---|---|
| 1/100 | 2.409 | 2.029 | 2.061 | 2.821 | 2.11 |
| 1/300 | 1.618 | 1.565 | 1.278 | 2.422 | 1.24 |

| 1 Ab | Indexx 6 | Indexx 7 | Indexx 8 | Indexx 9 | Indexx 10 |
|---|---|---|---|---|---|
| 1/100 | 2.51 | 2.012 | 1.883 | 1.743 | 2.268 |
| 1/300 | 1.985 | 1.24 | 1.11 | 1.041 | 1.596 |

| 1 Ab | Indexx 11 | Indexx 12 | Indexx 13 | Indexx 14 | Indexx 15 |
|---|---|---|---|---|---|
| 1/100 | 2.685 | 2.669 | 2.788 | 1.999 | 3.18 |
| 1/300 | 1.79 | 2.052 | 1.992 | 1.385 | 2.919 |

| 1 Ab | Indexx 16 | Indexx 17 | Indexx 18 | Indexx 19 | Indexx 20 |
|---|---|---|---|---|---|
| 1/100 | 3.023 | 2.471 | 2.443 | 2.466 | 3.184 |
| 1/300 | 2.544 | 1.907 | 2.155 | 1.788 | 2.821 |

We claim:

1. An isolated, recombinant, or purified polypeptide:
   a) comprising SEQ ID NO: 3;
   b) consisting of between 16 and 88 contiguous amino acids of SEQ ID NO: 3;
   c) comprising a heterologous polypeptide fused, in frame, to a polypeptide comprising SEQ ID NO: 3;
   d) comprising a heterologous polypeptide fused, in frame, to a polypeptide consisting of at least 16 consecutive amino acids of SEQ ID NO: 3 or;
   e) comprising a multimeric construction comprising SEQ ID NO: 3 or a multimeric construction containing a polypeptide fragment of SEQ ID NO: 3 consisting of at least 16 consecutive amino acids of SEQ ID NO: 3;
   wherein said isolated, recombinant or purified polypeptide elicits an immune response.

2. The isolated, recombinant or purified polypeptide according to claim 1, wherein said polypeptide comprises SEQ ID NO: 3.

3. The isolated, recombinant or purified polypeptide according to claim 1, wherein said polypeptide consists of at least 16 contiguous amino acids of SEQ ID NO: 3.

4. The isolated, recombinant or purified polypeptide according to claim 3, wherein said polypeptide consists of 16 to 88 consecutive amino acids of SEQ ID NO: 3.

5. The isolated, recombinant or purified polypeptide according to claim 1, wherein said polypeptide comprises a heterologous polypeptide fused, in frame, to a polypeptide consisting of at least 16 consecutive amino acids of SEQ ID NO: 3.

6. The isolated, recombinant or purified polypeptide according to claim 1, wherein said polypeptide comprises a heterologous polypeptide fused, in frame, to a polypeptide comprising SEQ ID NO: 3.

7. The isolated, recombinant or purified polypeptide according to claim 1, wherein said polypeptide comprises a multimeric construction comprising SEQ ID NO: 3.

8. The isolated, recombinant or purified polypeptide according to claim 5, wherein said polypeptide comprises a heterologous polypeptide fused, in frame, to a polypeptide consisting of 16 to 88 consecutive amino acids of SEQ ID NO: 3.

9. The isolated, recombinant or purified polypeptide according to claim 1, wherein said polypeptide comprises a multimeric construction that contains a polypeptide fragment consisting of at least 16 consecutive amino acids of SEQ ID NO: 3.

10. The isolated, recombinant or purified polypeptide according to claim 9, wherein said polypeptide comprises a multimeric construction that contains a polypeptide fragment consisting of 16-88 consecutive amino acids of SEQ ID NO: 3.

11. A composition comprising a component and:
    a) an isolated polypeptide comprising SEQ ID NO: 3;
    b) an isolated polypeptide consisting of between 16 and 88 contiguous amino acids of SEQ ID NO: 3;
    c) an isolated polypeptide comprising a heterologous polypeptide fused, in frame, to a polypeptide comprising SEQ ID NO: 3;
    d) an isolated polypeptide comprising a heterologous polypeptide fused, in frame, to a polypeptide consisting of at least 16 consecutive amino acids of SEQ ID NO: 3; or
    e) an isolated polypeptide comprising a multimeric construction comprising SEQ ID NO: 3 or a multimeric construction containing a polypeptide fragment of SEQ ID NO: 3 consisting of at least 16 consecutive amino acids of SEQ ID NO: 3;
    wherein said isolated, recombinant or purified polypeptide elicits an immune response.

12. The composition according to claim 11, wherein said component is a solid support.

13. The composition according to claim 12, wherein said solid support is selected from the group consisting of microtiter wells, magnetic beads, non-magnetic beads, agarose beads, glass, cellulose, plastics, polyethylene, polypropylene, polyester, nitrocellulose, nylon, and polysulfone.

14. The composition according to claim 11, wherein said component is a pharmaceutically acceptable excipient.

15. The composition according to claim 12, wherein said solid support provides an array of polypeptides and said array of polypeptides is selected from the group consisting of:
    a) an isolated polypeptide comprising SEQ ID NO: 3;
    b) an isolated polypeptide consisting of between 16 and 88 contiguous amino acids of SEQ ID NO: 3;
    c) an isolated polypeptide comprising a heterologous polypeptide fused, in frame, to a polypeptide comprising SEQ ID NO: 3;
    d) an isolated polypeptide comprising a heterologous polypeptide fused, in frame, to a polypeptide consisting of at least 16 consecutive amino acids of SEQ ID NO: 3; and
    e) an isolated polypeptide comprising a multimeric construction comprising SEQ ID NO: 3 or a multimeric construction containing a polypeptide fragment of SEQ ID NO: 3 consisting of at least 16 consecutive amino acids of SEQ ID NO: 3; and f) combinations of said polypeptides.

16. The composition of claim 15, further comprising an additional antigen of interest.

17. The composition of claim 11, further comprising an additional antigen of interest.

18. The composition of claim 11, wherein said isolated polypeptide comprises SEQ ID NO: 3.

19. The composition of claim 11, wherein said isolated polypeptide consists of at least 16 contiguous amino acids of SEQ ID NO: 3.

20. The composition of claim 19, wherein said isolated polypeptide consists of 16 to 88 consecutive amino acids of SEQ ID NO: 3.

21. The composition of claim 11, wherein said isolated polypeptide comprises a heterologous polypeptide fused, in frame, to a polypeptide consisting of at least 16 consecutive amino acids of SEQ ID NO: 3.

22. The composition of claim 11, wherein said isolated polypeptide comprises a heterologous polypeptide fused, in frame, to a polypeptide comprising SEQ ID NO: 3.

23. The composition of claim 11, wherein said isolated polypeptide comprises a multimeric construction comprising SEQ ID NO: 3.

24. The composition of claim 21, wherein said isolated polypeptide comprises a heterologous polypeptide fused, in frame, to a polypeptide consisting of 16 to 88 consecutive amino acids of SEQ ID NO: 3.

25. The composition of claim 11, wherein said isolated polypeptide comprises a multimeric construction that contains a polypeptide fragment consisting of at least 16 consecutive amino acids of SEQ ID NO: 3.

26. The composition of claim 25, wherein said isolated polypeptide comprises a multimeric construction that contains a polypeptide fragment consisting of 16-88 consecutive amino acids of SEQ ID NO: 3.

27. A method of inducing an immune response comprising administering to an individual a polypeptide:
a) comprising SEQ ID NO: 3;
b) consisting of between 16 and 88 contiguous amino acids of SEQ ID NO: 3;
c) comprising a heterologous polypeptide fused, in frame, to a polypeptide comprising SEQ ID NO: 3;
d) comprising a heterologous polypeptide fused, in frame, to a polypeptide consisting of at least 16 consecutive amino acids of SEQ ID NO: 3; or
e) comprising a multimeric construction comprising SEQ ID NO: 3 or a multimeric construction containing a polypeptide fragment of SEQ ID NO: 3 consisting of at least 16 consecutive amino acids of SEQ ID NO: 3.

28. The method according to claim 27, wherein said method also comprises administering an additional antigen of interest.

29. The method according to claim 27, wherein said polypeptide comprises SEQ ID NO: 3.

30. The method according to claim 27, wherein said polypeptide consists of at least 16 contiguous amino acids of SEQ ID NO: 3.

31. The method according to claim 20, wherein said polypeptide consists of 16 to 88 consecutive amino acids of SEQ ID NO: 3.

32. The method according to claim 27, wherein said polypeptide comprises a heterologous polypeptide fused, in frame, to a polypeptide consisting of at least 16 consecutive amino acids of SEQ ID NO: 3.

33. The method according to claim 27, wherein said polypeptide comprises a heterologous polypeptide fused, in frame, to a polypeptide comprising SEQ ID NO: 3.

34. The method according to claim 27, wherein said polypeptide comprises a multimeric construction comprising SEQ ID NO: 3.

35. The method according to claim 27, wherein said polypeptide comprises a heterologous polypeptide fused, in frame, to a polypeptide consisting of 16 to 88 consecutive amino acids of SEQ ID NO: 3.

36. The method according to claim 27, wherein said polypeptide comprises a multimeric construction that contains a polypeptide fragment consisting of at least 16 consecutive amino acids of SEQ ID NO: 3.

37. The method according to claim 36, wherein said isolated polypeptide comprises a multimeric construction that contains a polypeptide fragment consisting of 16-88 consecutive amino acids of SEQ ID NO: 3.

38. In a method of detecting the presence of antibodies that specifically bind to *Anaplasma phagocytophilum* or antigens thereof, the improvement comprising the use of a polypeptide:
a) comprising SEQ ID NO: 3;
b) consisting of between 16 and 88 contiguous amino acids of SEQ ID NO: 3;
c) comprising a heterologous polypeptide fused, in frame, to a polypeptide comprising SEQ ID NO: 3;
d) comprising a heterologous polypeptide fused, in frame, to a polypeptide consisting of at least 16 consecutive amino acids of SEQ ID NO: 3; or
e) comprising a multimeric construction comprising SEQ ID NO: 3 or a multimeric construction containing a polypeptide fragment of SEQ ID NO: 3 consisting of at least 16 consecutive amino acids of SEQ ID NO: 3.

39. In the method according to claim 38, the improvement comprising the use of a polypeptide comprising SEQ ID NO: 3.

40. In the method according to claim 38, the improvement comprising the use of a polypeptide consisting of at least 16 contiguous amino acids of SEQ ID NO: 3.

41. In the method according to claim 40, the improvement comprising the use of a polypeptide consisting of 16 to 88 consecutive amino acids of SEQ ID NO: 3.

42. In the method according to claim 38, the improvement comprising the use of a polypeptide comprising a heterologous polypeptide fused, in frame, to a polypeptide consisting of at least 16 consecutive amino acids of SEQ ID NO: 3.

43. In the method according to claim 38, the improvement comprising the use of a polypeptide that comprises a heterologous polypeptide fused, in frame, to a polypeptide comprising SEQ ID NO: 3.

44. In the method according to claim 38, the improvement comprising the use of a polypeptide that comprises a multimeric construction comprising SEQ ID NO: 3.

45. In the method according to claim 42, the improvement comprising the use of a polypeptide that comprises a heterologous polypeptide fused, in frame, to a polypeptide consisting of 16 to 88 consecutive amino acids of SEQ ID NO: 3.

46. In the method according to claim 38, the improvement comprising the use of a polypeptide that comprises a multimeric construction that contains a polypeptide fragment consisting of at least 16 consecutive amino acids of SEQ ID NO: 3.

47. In the method according to claim 46, the improvement comprising the use of a polypeptide that comprises a multimeric construction that contains a polypeptide fragment consisting of 16-88 consecutive amino acids of SEQ ID NO: 3.

* * * * *

UNITED STATES PATENT AND TRADEMARK OFFICE
CERTIFICATE OF CORRECTION

PATENT NO. : 7,304,139 B2 Page 1 of 1
APPLICATION NO. : 10/696019
DATED : December 4, 2007
INVENTOR(S) : Arthur Rick Alleman and Anthony F. Barbet It is certified that error appears in the above-identified patent and that said Letters Patent is hereby corrected as shown below:

Column 5,
Line 22, "(cytptoxic T-lymphocyte)" should read --(cytotoxic T-lymphocyte)--.

Column 15,
Line 42, "0.1 mg/mil" should read --0.1 mg/ml--.

Signed and Sealed this

Tenth Day of June, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 742
<212> TYPE: DNA
<213> ORGANISM: Anaplasma phagocytophilum
<220> FEATURE:
<221> NAME/KEY: misc_feature
<222> LOCATION: (29)..(250)
<223> OTHER INFORMATION: Coding sequence of processed MSP5 polypeptide

```
<220> FEATURE:
<221> NAME/KEY: misc_feature
<222> LOCATION: (29)..(610)
<223> OTHER INFORMATION: 5' and 3' ends of cloned MSP5 insert

<400> SEQUENCE: 1
aaataaggag gaataaacca tggcccttac tgtgtttctg gggtattcgt atgttaacaa    60
aaagggaata ttcagtgaca tgggtgctaa attaagtagt actgacactg tggttgaaca   120
agcgccgata ttggcttctt ttactgatct gataaatcaa gaaggtcagg ttgttagtag   180
cactgatttt gctgggaagc acatgttgct tatgttcggc ttttcttcat gcaagcacat   240
atgtcctgcg gaacttggta tggtatcgca acttttaaac aagttgggtg agactgctga   300
taaacttcaa gctgttttca taactattga tcccaaaaat gacactgttg aaaggttaaa   360
tgagtatcac aaagcctttg atagtcgaat tcagatgctg actggggatg aggaagttat   420
tcgcaatgta gtgaataatt ataaggtata cgtaggtgag tctgatagtg aaggagatat   480
taatcactca tcgttttgt acttggttga tgccgacgga agatatgtag gcatttttgc   540
tcctgatttt gatgaatacg aaagtcaagt aggtagactt tttgatttcg ttaataagta   600
ccctacttct aagggcgaat tcgaagctta cgtagaacaa aaactcatct cagaagagga   660
tctgaatagc gccgtcgacc atcatcatca tcatcattga gtttaaacgg tctccagctt   720
ggctgttttg gcggatgaga ga                                            742

<210> SEQ ID NO 2
<211> LENGTH: 74
<212> TYPE: PRT
<213> ORGANISM: Anaplasma phagocytophilum

<400> SEQUENCE: 2

Thr Val Phe Leu Gly Tyr Ser Tyr Val Asn Lys Lys Gly Ile Phe Ser
1               5                  10                   15

Asp Met Gly Ala Lys Leu Ser Ser Thr Asp Thr Val Val Glu Gln Ala
            20                  25                  30

Pro Ile Leu Ala Ser Phe Thr Asp Leu Ile Asn Gln Glu Gly Gln Val
        35                  40                  45

Val Ser Ser Thr Asp Phe Ala Gly Lys His Met Leu Leu Met Phe Gly
    50                  55                  60

Phe Ser Ser Cys Lys His Ile Cys Pro Ala
65                  70

<210> SEQ ID NO 3
<211> LENGTH: 89
<212> TYPE: PRT
<213> ORGANISM: Anaplasma phagocytophilum

<400> SEQUENCE: 3

Met Lys Thr Phe Lys Thr Val Ser Asn Leu Leu Leu Val Ala Thr
1               5                  10                   15

Val Phe Leu Gly Tyr Ser Tyr Val Asn Lys Lys Gly Ile Phe Ser Asp
            20                  25                  30

Met Gly Ala Lys Leu Ser Ser Thr Asp Thr Val Val Glu Gln Ala Pro
        35                  40                  45

Ile Leu Ala Ser Phe Thr Asp Leu Ile Asn Gln Glu Gly Gln Val Val
    50                  55                  60

Ser Ser Thr Asp Phe Ala Gly Lys His Met Leu Leu Met Phe Gly Phe
65                  70                  75                  80
```

```
Ser Ser Cys Lys His Ile Cys Pro Ala
                85

<210> SEQ ID NO 4
<211> LENGTH: 15
<212> TYPE: PRT
<213> ORGANISM: Anaplasma phagocytophilum
<220> FEATURE:
<221> NAME/KEY: MISC_FEATURE
<222> LOCATION: (1)..(15)
<223> OTHER INFORMATION: MSP5 signal peptide

<400> SEQUENCE: 4

Met Lys Thr Phe Lys Thr Val Ser Asn Leu Leu Leu Val Ala
1               5                   10                  15
```